(12) United States Patent
Morel et al.

(10) Patent No.: US 10,647,739 B2
(45) Date of Patent: May 12, 2020

(54) FLAVONOIDS O-A-GLUCOSYLATED ON THE B CYCLE, METHOD FOR THE PRODUCTION THEREOF AND USES

(71) Applicants: Institut National de la Recherche Agronomique, Paris (FR); Institut National des Sciences Appliquees de Toulouse, Toulouse (FR); Centre National de la Recherche Scientifique, Paris (FR)

(72) Inventors: Sandrine Morel, Auzeville-Tolosane (FR); Isabelle Andre, Toulouse (FR); Yoan Brison, Toulouse (FR); Emmanuelle Cambon, Montpellier (FR); Yannick Malbert, Saint-Alban (FR); Denis Pompon, Pechabou (FR); Magali Remaud-Simeon, Ramonville (FR); Philippe Urban, Ramonville-saint-Agne (FR)

(73) Assignees: INSTITUT NATIONAL DE LA RECHERCHE AGRONOMIQUE, Paris (FR); INSTITUTE NATIONAL DES SCIENCES APPLIQUEES DE TOULOUSE, Toulouse (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 441 days.

(21) Appl. No.: 15/128,673

(22) PCT Filed: Mar. 24, 2015

(86) PCT No.: PCT/EP2015/056307
§ 371 (c)(1),
(2) Date: Sep. 23, 2016

(87) PCT Pub. No.: WO2015/144371
PCT Pub. Date: Oct. 1, 2015

(65) Prior Publication Data
US 2017/0107242 A1    Apr. 20, 2017

(30) Foreign Application Priority Data

Mar. 24, 2014 (FR) .................................. 14 52461
Jul. 3, 2014 (FR) .................................. 14 56417

(51) Int. Cl.
| | |
|---|---|
| *C07H 15/203* | (2006.01) |
| *A61K 8/60* | (2006.01) |
| *C12P 19/46* | (2006.01) |
| *C07H 17/07* | (2006.01) |
| *C12P 19/60* | (2006.01) |
| *C07D 311/30* | (2006.01) |
| *C07D 311/32* | (2006.01) |
| *C07H 1/00* | (2006.01) |
| *A61Q 19/00* | (2006.01) |
| *A01N 43/16* | (2006.01) |
| *A61K 31/7048* | (2006.01) |
| *A61Q 19/02* | (2006.01) |

(52) U.S. Cl.
CPC .......... *C07H 15/203* (2013.01); *A01N 43/16* (2013.01); *A61K 8/602* (2013.01); *A61K 31/7048* (2013.01); *A61Q 19/00* (2013.01); *A61Q 19/02* (2013.01); *C07D 311/30* (2013.01); *C07D 311/32* (2013.01); *C07H 1/00* (2013.01); *C07H 17/07* (2013.01); *C12P 19/46* (2013.01); *C12P 19/60* (2013.01); *C12Y 204/01004* (2013.01); *C12Y 204/01005* (2013.01); *C12Y 204/0114* (2013.01); *A61K 2800/522* (2013.01)

(58) Field of Classification Search
None
See application file for complete search history.

(56) References Cited

FOREIGN PATENT DOCUMENTS

| | | |
|---|---|---|
| EP | 2 145 615 | 1/2010 |
| JP | 1999-0225840 | 8/1999 |
| KR | 20060063703 | 6/2006 |

OTHER PUBLICATIONS

Bertrand et al., *Leuconostoc mesenteroides glucansurase synthesis of flavonoid glucosides by acceptor reactions in aqueous-organic solvents*, 341 Carbohydrate Research 855-863 (2006).
Brison et al., *Functional and Structural Characterization of α-(1→2)Branching Sucrase Derived from DSR-E Glucansucrase*, 287(11) The Journal of Biological Chemistry 7915-7924 (Mar. 9, 2012).
Champion et al., *Applying Pairwise Combinations of Amino Acid Mutations for Sorting Out Highly Efficient Glucosylation Tools for Chemo-Enzymatic Synthesis of Bacterial Oligsaccharides*, 134 J. Am. Chem. 18677-18688 (2012).
(Continued)

*Primary Examiner* — Paul J Holland
(74) *Attorney, Agent, or Firm* — Buchanan Ingersoll & Rooney PC

(57) ABSTRACT

The invention relates to a method for producing derivatives of O-α-glucosylated flavonoid, comprising at least one step of incubating a glucansucrase with a flavonoid and at least one sucrose, the flavonoid being a flavonoid which is monohydroxylated or hydroxylated in a non-vicinal manner on the B cycle. The invention also relates to novel O-α-glucosylated flavonoid derivatives, and to the use thereof.

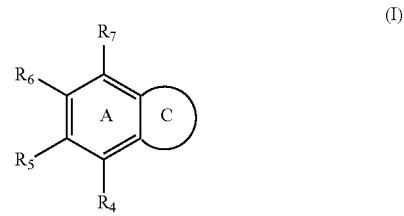

(I)

12 Claims, 32 Drawing Sheets
Specification includes a Sequence Listing.

(56) References Cited

OTHER PUBLICATIONS

Esaki et al., *Preparation and Taste of Certain Glycosides of Flavanones and of Dihydrochalcones*, 58(8) Biosci. Biotech. Biochem. 1479-1485 (1994).

Moon et al., *Synthesis and characterization of novel quercetin-α-glucopyranosides using glucansucrase from Leuconostoc mesenteroides*, 40 Enzyme and Microbial Technology 1124-1129 (2007).

Moon et al., *Synthesis, Structure Analyses, and Characterization of Novel Epigallocatechin Gallate (EGCG) Glycosides using the Glucansucrase from Leuconostoc mesenteroides B-1299CB*, 54 J. Agric. Food Chem. 1230-1237 (2006).

Tramice et al., *Direct enzymatic glucosylation of naringin in grapefruit juice α-D-glucosidase from the marine mollusc Aplysia fasciata*, 3 Biotechnol. J. 545-554 (2008).

Werner et al., *Expression of a Dianthus flavonoid glucosyltransferase in Saccharomyces cerevisiae for whole-cell biocatalysis*, 142 Journal of Biotechnology 233-241 (2009).

International Search Report dated Jun. 26, 2016, in corresponding International Patent Publication No. PCT/EP2015/056307.

SEQUENCE LISTING

<160> NUMBER OF SEQ ID NOS: 13

<210> SEQ ID NO 1
<211> LENGTH: 628
<212> TYPE: PRT
<213> ORGANISM: Neisseria polysaccharea
<220> FEATURE:
<221> NAME/KEY: VARIANT
<222> LOCATION: (226)..(226)
<223> OTHER INFORMATION: Xaa is chosen among A, C, E, F, G, H, I, K, M, N, P, Q, S, T, V and Y

<400> SEQUENCE: 1

```
Ser Pro Asn Ser Gln Tyr Leu Lys Thr Arg Ile Leu Asp Ile Tyr Thr
1               5                   10                  15

Pro Glu Gln Arg Ala Gly Ile Glu Lys Ser Glu Asp Trp Arg Gln Phe
            20                  25                  30

Ser Arg Arg Met Asp Thr His Phe Pro Lys Leu Met Asn Glu Leu Asp
        35                  40                  45

Ser Val Tyr Gly Asn Asn Glu Ala Leu Leu Pro Met Leu Glu Met Leu
    50                  55                  60

Leu Ala Gln Ala Trp Gln Ser Tyr Ser Gln Arg Asn Ser Ser Leu Lys
65                  70                  75                  80

Asp Ile Asp Ile Ala Arg Glu Asn Asn Pro Asp Trp Ile Leu Ser Asn
                85                  90                  95

Lys Gln Val Gly Gly Val Cys Tyr Val Asp Leu Phe Ala Gly Asp Leu
            100                 105                 110

Lys Gly Leu Lys Asp Lys Ile Pro Tyr Phe Gln Glu Leu Gly Leu Thr
        115                 120                 125

Tyr Leu His Leu Met Pro Leu Phe Lys Cys Pro Glu Gly Lys Ser Asp
    130                 135                 140

Gly Gly Tyr Ala Val Ser Ser Tyr Arg Asp Val Asn Pro Ala Leu Gly
145                 150                 155                 160

Thr Ile Gly Asp Leu Arg Glu Val Ile Ala Ala Leu His Glu Ala Gly
                165                 170                 175

Ile Ser Ala Val Val Asp Phe Ile Phe Asn His Thr Ser Asn Glu His
            180                 185                 190

Glu Trp Ala Gln Arg Cys Ala Ala Gly Asp Pro Leu Phe Asp Asn Phe
        195                 200                 205

Tyr Tyr Ile Phe Pro Asp Arg Arg Met Pro Asp Gln Tyr Asp Arg Thr
    210                 215                 220

Leu Xaa Glu Ile Phe Pro Asp Gln His Pro Gly Gly Phe Ser Gln Leu
225                 230                 235                 240

Glu Asp Gly Arg Trp Val Trp Thr Thr Phe Asn Ser Phe Gln Trp Asp
                245                 250                 255

Leu Asn Tyr Ser Asn Pro Trp Val Phe Arg Ala Met Ala Gly Glu Met
            260                 265                 270

Leu Phe Leu Ala Asn Leu Gly Val Asp Ile Leu Arg Met Asp Ala Val
        275                 280                 285

Ala Phe Ile Trp Lys Gln Met Gly Thr Ser Cys Glu Asn Leu Pro Gln
    290                 295                 300

Ala His Ala Leu Ile Arg Ala Phe Asn Ala Val Met Arg Ile Ala Ala
305                 310                 315                 320

Pro Ala Val Phe Phe Lys Ser Glu Ala Ile Val His Pro Asp Gln Val
                325                 330                 335

Val Gln Tyr Ile Gly Gln Asp Glu Cys Gln Ile Gly Tyr Asn Pro Leu
```

```
                340             345             350
    Gln Met Ala Leu Leu Trp Asn Thr Leu Ala Thr Arg Glu Val Asn Leu
                355                 360                 365

Leu His Gln Ala Leu Thr Tyr Arg His Asn Leu Pro Glu His Thr Ala
            370                 375                 380

Trp Val Asn Tyr Val Arg Ser His Asp Asp Ile Gly Trp Thr Phe Ala
385                 390                 395                 400

Asp Glu Asp Ala Ala Tyr Leu Gly Ile Ser Gly Tyr Asp His Arg Gln
                405                 410                 415

Phe Leu Asn Arg Phe Phe Val Asn Arg Phe Asp Gly Ser Phe Ala Arg
                420                 425                 430

Gly Val Pro Phe Gln Tyr Asn Pro Ser Thr Gly Asp Cys Arg Val Ser
                435                 440                 445

Gly Thr Ala Ala Ala Leu Val Gly Leu Ala Gln Asp Asp Pro His Ala
                450                 455                 460

Val Asp Arg Ile Lys Leu Leu Tyr Ser Ile Ala Leu Ser Thr Gly Gly
465                 470                 475                 480

Leu Pro Leu Ile Tyr Leu Gly Asp Glu Val Gly Thr Leu Asn Asp Asp
                485                 490                 495

Asp Trp Ser Gln Asp Ser Asn Lys Ser Asp Ser Arg Trp Ala His
                500                 505                 510

Arg Pro Arg Tyr Asn Glu Ala Leu Tyr Ala Gln Arg Asn Asp Pro Ser
                515                 520                 525

Thr Ala Ala Gly Gln Ile Tyr Gln Asp Leu Arg His Met Ile Ala Val
                530                 535                 540

Arg Gln Ser Asn Pro Arg Phe Asp Gly Gly Arg Leu Val Thr Phe Asn
545                 550                 555                 560

Thr Asn Asn Lys His Ile Ile Gly Tyr Ile Arg Asn Asn Ala Leu Leu
                565                 570                 575

Ala Phe Gly Asn Phe Ser Glu Tyr Pro Gln Thr Val Thr Ala His Thr
                580                 585                 590

Leu Gln Ala Met Pro Phe Lys Ala His Asp Leu Ile Gly Gly Lys Thr
                595                 600                 605

Val Ser Leu Asn Gln Asp Leu Thr Leu Gln Pro Tyr Gln Val Met Trp
                610                 615                 620

Leu Glu Ile Ala
625
```

<210> SEQ ID NO 2
<211> LENGTH: 628
<212> TYPE: PRT
<213> ORGANISM: Neisseria polysaccharea
<220> FEATURE:
<221> NAME/KEY: VARIANT
<222> LOCATION: (228)..(228)
<223> OTHER INFORMATION: Xaa is chosen among A, C, D, F, G, H, K, L, M, N, P, S, V and Y

<400> SEQUENCE: 2

```
    Ser Pro Asn Ser Gln Tyr Leu Lys Thr Arg Ile Leu Asp Ile Tyr Thr
1               5                   10                  15

Pro Glu Gln Arg Ala Gly Ile Glu Lys Ser Glu Asp Trp Arg Gln Phe
                20                  25                  30

Ser Arg Arg Met Asp Thr His Phe Pro Lys Leu Met Asn Glu Leu Asp
                35                  40                  45

Ser Val Tyr Gly Asn Asn Glu Ala Leu Leu Pro Met Leu Glu Met Leu
```

```
                50                  55                  60
Leu Ala Gln Ala Trp Gln Ser Tyr Ser Gln Arg Asn Ser Ser Leu Lys
65                  70                  75                  80

Asp Ile Asp Ile Ala Arg Glu Asn Asn Pro Asp Trp Ile Leu Ser Asn
                85                  90                  95

Lys Gln Val Gly Val Cys Tyr Val Asp Leu Phe Ala Gly Asp Leu
            100                 105                 110

Lys Gly Leu Lys Asp Lys Ile Pro Tyr Phe Gln Glu Leu Gly Leu Thr
            115                 120                 125

Tyr Leu His Leu Met Pro Leu Phe Lys Cys Pro Glu Gly Lys Ser Asp
            130                 135                 140

Gly Gly Tyr Ala Val Ser Ser Tyr Arg Asp Val Asn Pro Ala Leu Gly
145                 150                 155                 160

Thr Ile Gly Asp Leu Arg Glu Val Ile Ala Ala Leu His Glu Ala Gly
                165                 170                 175

Ile Ser Ala Val Val Asp Phe Ile Phe Asn His Thr Ser Asn Glu His
            180                 185                 190

Glu Trp Ala Gln Arg Cys Ala Ala Gly Asp Pro Leu Phe Asp Asn Phe
            195                 200                 205

Tyr Tyr Ile Phe Pro Asp Arg Arg Met Pro Asp Gln Tyr Asp Arg Thr
210                 215                 220

Leu Arg Glu Xaa Phe Pro Asp Gln His Pro Gly Gly Phe Ser Gln Leu
225                 230                 235                 240

Glu Asp Gly Arg Trp Val Trp Thr Thr Phe Asn Ser Phe Gln Trp Asp
                245                 250                 255

Leu Asn Tyr Ser Asn Pro Trp Val Phe Arg Ala Met Ala Gly Glu Met
            260                 265                 270

Leu Phe Leu Ala Asn Leu Gly Val Asp Ile Leu Arg Met Asp Ala Val
            275                 280                 285

Ala Phe Ile Trp Lys Gln Met Gly Thr Ser Cys Glu Asn Leu Pro Gln
            290                 295                 300

Ala His Ala Leu Ile Arg Ala Phe Asn Ala Val Met Arg Ile Ala Ala
305                 310                 315                 320

Pro Ala Val Phe Phe Lys Ser Glu Ala Ile Val His Pro Asp Gln Val
                325                 330                 335

Val Gln Tyr Ile Gly Gln Asp Glu Cys Gln Ile Gly Tyr Asn Pro Leu
            340                 345                 350

Gln Met Ala Leu Leu Trp Asn Thr Leu Ala Thr Arg Glu Val Asn Leu
            355                 360                 365

Leu His Gln Ala Leu Thr Tyr Arg His Asn Leu Pro Glu His Thr Ala
            370                 375                 380

Trp Val Asn Tyr Val Arg Ser His Asp Asp Ile Gly Trp Thr Phe Ala
385                 390                 395                 400

Asp Glu Asp Ala Ala Tyr Leu Gly Ile Ser Gly Tyr Asp His Arg Gln
                405                 410                 415

Phe Leu Asn Arg Phe Phe Val Asn Arg Phe Asp Gly Ser Phe Ala Arg
            420                 425                 430

Gly Val Pro Phe Gln Tyr Asn Pro Ser Thr Gly Asp Cys Arg Val Ser
            435                 440                 445

Gly Thr Ala Ala Ala Leu Val Gly Leu Ala Gln Asp Asp Pro His Ala
            450                 455                 460

Val Asp Arg Ile Lys Leu Leu Tyr Ser Ile Ala Leu Ser Thr Gly Gly
465                 470                 475                 480
```

```
Leu Pro Leu Ile Tyr Leu Gly Asp Glu Val Gly Thr Leu Asn Asp Asp
            485                 490                 495

Asp Trp Ser Gln Asp Ser Asn Lys Ser Asp Asp Ser Arg Trp Ala His
        500                 505                 510

Arg Pro Arg Tyr Asn Glu Ala Leu Tyr Ala Gln Arg Asn Asp Pro Ser
    515                 520                 525

Thr Ala Ala Gly Gln Ile Tyr Gln Asp Leu Arg His Met Ile Ala Val
530                 535                 540

Arg Gln Ser Asn Pro Arg Phe Asp Gly Gly Arg Leu Val Thr Phe Asn
545                 550                 555                 560

Thr Asn Asn Lys His Ile Ile Gly Tyr Ile Arg Asn Asn Ala Leu Leu
                565                 570                 575

Ala Phe Gly Asn Phe Ser Glu Tyr Pro Gln Thr Val Thr Ala His Thr
            580                 585                 590

Leu Gln Ala Met Pro Phe Lys Ala His Asp Leu Ile Gly Gly Lys Thr
        595                 600                 605

Val Ser Leu Asn Gln Asp Leu Thr Leu Gln Pro Tyr Gln Val Met Trp
    610                 615                 620

Leu Glu Ile Ala
625

<210> SEQ ID NO 3
<211> LENGTH: 628
<212> TYPE: PRT
<213> ORGANISM: Neisseria polysaccharea
<220> FEATURE:
<221> NAME/KEY: VARIANT
<222> LOCATION: (229)..(229)
<223> OTHER INFORMATION: Xaa is chosen among A, C, G, I, K, M, N and W

<400> SEQUENCE: 3

Ser Pro Asn Ser Gln Tyr Leu Lys Thr Arg Ile Leu Asp Ile Tyr Thr
1               5                   10                  15

Pro Glu Gln Arg Ala Gly Ile Glu Lys Ser Glu Asp Trp Arg Gln Phe
            20                  25                  30

Ser Arg Arg Met Asp Thr His Phe Pro Lys Leu Met Asn Glu Leu Asp
        35                  40                  45

Ser Val Tyr Gly Asn Asn Glu Ala Leu Leu Pro Met Leu Glu Met Leu
    50                  55                  60

Leu Ala Gln Ala Trp Gln Ser Tyr Ser Gln Arg Asn Ser Ser Leu Lys
65                  70                  75                  80

Asp Ile Asp Ile Ala Arg Glu Asn Asn Pro Asp Trp Ile Leu Ser Asn
                85                  90                  95

Lys Gln Val Gly Val Cys Tyr Val Asp Leu Phe Ala Gly Asp Leu
            100                 105                 110

Lys Gly Leu Lys Asp Lys Ile Pro Tyr Phe Gln Glu Leu Gly Leu Thr
        115                 120                 125

Tyr Leu His Leu Met Pro Leu Phe Lys Cys Pro Glu Gly Lys Ser Asp
    130                 135                 140

Gly Gly Tyr Ala Val Ser Ser Tyr Arg Asp Val Asn Pro Ala Leu Gly
145                 150                 155                 160

Thr Ile Gly Asp Leu Arg Glu Val Ile Ala Ala Leu His Glu Ala Gly
                165                 170                 175

Ile Ser Ala Val Val Asp Phe Ile Phe Asn His Thr Ser Asn Glu His
            180                 185                 190
```

-continued

```
Glu Trp Ala Gln Arg Cys Ala Ala Gly Asp Pro Leu Phe Asp Asn Phe
            195                 200                 205

Tyr Tyr Ile Phe Pro Asp Arg Arg Met Pro Asp Gln Tyr Asp Arg Thr
        210                 215                 220

Leu Arg Glu Ile Xaa Pro Asp Gln His Pro Gly Gly Phe Ser Gln Leu
225                 230                 235                 240

Glu Asp Gly Arg Trp Val Trp Thr Thr Phe Asn Ser Phe Gln Trp Asp
                245                 250                 255

Leu Asn Tyr Ser Asn Pro Trp Val Phe Arg Ala Met Ala Gly Glu Met
            260                 265                 270

Leu Phe Leu Ala Asn Leu Gly Val Asp Ile Leu Arg Met Asp Ala Val
        275                 280                 285

Ala Phe Ile Trp Lys Gln Met Gly Thr Ser Cys Glu Asn Leu Pro Gln
290                 295                 300

Ala His Ala Leu Ile Arg Ala Phe Asn Ala Val Met Arg Ile Ala Ala
305                 310                 315                 320

Pro Ala Val Phe Phe Lys Ser Glu Ala Ile Val His Pro Asp Gln Val
                325                 330                 335

Val Gln Tyr Ile Gly Gln Asp Glu Cys Gln Ile Gly Tyr Asn Pro Leu
            340                 345                 350

Gln Met Ala Leu Leu Trp Asn Thr Leu Ala Thr Arg Glu Val Asn Leu
        355                 360                 365

Leu His Gln Ala Leu Thr Tyr Arg His Asn Leu Pro Glu His Thr Ala
370                 375                 380

Trp Val Asn Tyr Val Arg Ser His Asp Asp Ile Gly Trp Thr Phe Ala
385                 390                 395                 400

Asp Glu Asp Ala Ala Tyr Leu Gly Ile Ser Gly Tyr Asp His Arg Gln
                405                 410                 415

Phe Leu Asn Arg Phe Phe Val Asn Arg Phe Asp Gly Ser Phe Ala Arg
            420                 425                 430

Gly Val Pro Phe Gln Tyr Asn Pro Ser Thr Gly Asp Cys Arg Val Ser
        435                 440                 445

Gly Thr Ala Ala Ala Leu Val Gly Leu Ala Gln Asp Asp Pro His Ala
450                 455                 460

Val Asp Arg Ile Lys Leu Leu Tyr Ser Ile Ala Leu Ser Thr Gly Gly
465                 470                 475                 480

Leu Pro Leu Ile Tyr Leu Gly Asp Glu Val Gly Thr Leu Asn Asp Asp
                485                 490                 495

Asp Trp Ser Gln Asp Ser Asn Lys Ser Asp Asp Ser Arg Trp Ala His
            500                 505                 510

Arg Pro Arg Tyr Asn Glu Ala Leu Tyr Ala Gln Arg Asn Asp Pro Ser
        515                 520                 525

Thr Ala Gly Gln Ile Tyr Gln Asp Leu Arg His Met Ile Ala Val
530                 535                 540

Arg Gln Ser Asn Pro Arg Phe Asp Gly Arg Leu Val Thr Phe Asn
545                 550                 555                 560

Thr Asn Asn Lys His Ile Ile Gly Tyr Ile Arg Asn Asn Ala Leu Leu
                565                 570                 575

Ala Phe Gly Asn Phe Ser Glu Tyr Pro Gln Thr Val Thr Ala His Thr
            580                 585                 590

Leu Gln Ala Met Pro Phe Lys Ala His Asp Leu Ile Gly Gly Lys Thr
        595                 600                 605

Val Ser Leu Asn Gln Asp Leu Thr Leu Gln Pro Tyr Gln Val Met Trp
```

610                 615                 620

Leu Glu Ile Ala
625

<210> SEQ ID NO 4
<211> LENGTH: 628
<212> TYPE: PRT
<213> ORGANISM: Neisseria polysaccharea
<220> FEATURE:
<221> NAME/KEY: VARIANT
<222> LOCATION: (289)..(289)
<223> OTHER INFORMATION: Xaa is chosen among C, I, N, P, V and W

<400> SEQUENCE: 4

Ser Pro Asn Ser Gln Tyr Leu Lys Thr Arg Ile Leu Asp Ile Tyr Thr
1               5                   10                  15

Pro Glu Gln Arg Ala Gly Ile Glu Lys Ser Glu Asp Trp Arg Gln Phe
            20                  25                  30

Ser Arg Arg Met Asp Thr His Phe Pro Lys Leu Met Asn Glu Leu Asp
        35                  40                  45

Ser Val Tyr Gly Asn Asn Glu Ala Leu Leu Pro Met Leu Glu Met Leu
    50                  55                  60

Leu Ala Gln Ala Trp Gln Ser Tyr Ser Gln Arg Asn Ser Ser Leu Lys
65                  70                  75                  80

Asp Ile Asp Ile Ala Arg Glu Asn Asn Pro Asp Trp Ile Leu Ser Asn
                85                  90                  95

Lys Gln Val Gly Gly Val Cys Tyr Val Asp Leu Phe Ala Gly Asp Leu
            100                 105                 110

Lys Gly Leu Lys Asp Lys Ile Pro Tyr Phe Gln Glu Leu Gly Leu Thr
        115                 120                 125

Tyr Leu His Leu Met Pro Leu Phe Lys Cys Pro Glu Gly Lys Ser Asp
    130                 135                 140

Gly Gly Tyr Ala Val Ser Ser Tyr Arg Asp Val Asn Pro Ala Leu Gly
145                 150                 155                 160

Thr Ile Gly Asp Leu Arg Glu Val Ile Ala Ala Leu His Glu Ala Gly
                165                 170                 175

Ile Ser Ala Val Val Asp Phe Ile Phe Asn His Thr Ser Asn Glu His
            180                 185                 190

Glu Trp Ala Gln Arg Cys Ala Ala Gly Asp Pro Leu Phe Asp Asn Phe
        195                 200                 205

Tyr Tyr Ile Phe Pro Asp Arg Arg Met Pro Asp Gln Tyr Asp Arg Thr
    210                 215                 220

Leu Arg Glu Ile Phe Pro Asp Gln His Pro Gly Gly Phe Ser Gln Leu
225                 230                 235                 240

Glu Asp Gly Arg Trp Val Trp Thr Thr Phe Asn Ser Phe Gln Trp Asp
                245                 250                 255

Leu Asn Tyr Ser Asn Pro Trp Val Phe Arg Ala Met Ala Gly Glu Met
            260                 265                 270

Leu Phe Leu Ala Asn Leu Gly Val Asp Ile Leu Arg Met Asp Ala Val
        275                 280                 285

Xaa Phe Ile Trp Lys Gln Met Gly Thr Ser Cys Glu Asn Leu Pro Gln
    290                 295                 300

Ala His Ala Leu Ile Arg Ala Phe Asn Ala Val Met Arg Ile Ala Ala
305                 310                 315                 320

Pro Ala Val Phe Phe Lys Ser Glu Ala Ile Val His Pro Asp Gln Val
                325                 330                 335

Val Gln Tyr Ile Gly Gln Asp Glu Cys Gln Ile Gly Tyr Asn Pro Leu
            340                 345                 350

Gln Met Ala Leu Leu Trp Asn Thr Leu Ala Thr Arg Glu Val Asn Leu
        355                 360                 365

Leu His Gln Ala Leu Thr Tyr Arg His Asn Leu Pro Glu His Thr Ala
370                 375                 380

Trp Val Asn Tyr Val Arg Ser His Asp Asp Ile Gly Trp Thr Phe Ala
385                 390                 395                 400

Asp Glu Asp Ala Ala Tyr Leu Gly Ile Ser Gly Tyr Asp His Arg Gln
                405                 410                 415

Phe Leu Asn Arg Phe Phe Val Asn Arg Phe Asp Gly Ser Phe Ala Arg
            420                 425                 430

Gly Val Pro Phe Gln Tyr Asn Pro Ser Thr Gly Asp Cys Arg Val Ser
        435                 440                 445

Gly Thr Ala Ala Ala Leu Val Gly Leu Ala Gln Asp Asp Pro His Ala
450                 455                 460

Val Asp Arg Ile Lys Leu Leu Tyr Ser Ile Ala Leu Ser Thr Gly Gly
465                 470                 475                 480

Leu Pro Leu Ile Tyr Leu Gly Asp Glu Val Gly Thr Leu Asn Asp Asp
                485                 490                 495

Asp Trp Ser Gln Asp Ser Asn Lys Ser Asp Asp Ser Arg Trp Ala His
            500                 505                 510

Arg Pro Arg Tyr Asn Glu Ala Leu Tyr Ala Gln Arg Asn Asp Pro Ser
        515                 520                 525

Thr Ala Ala Gly Gln Ile Tyr Gln Asp Leu Arg His Met Ile Ala Val
530                 535                 540

Arg Gln Ser Asn Pro Arg Phe Asp Gly Gly Arg Leu Val Thr Phe Asn
545                 550                 555                 560

Thr Asn Asn Lys His Ile Ile Gly Tyr Ile Arg Asn Asn Ala Leu Leu
                565                 570                 575

Ala Phe Gly Asn Phe Ser Glu Tyr Pro Gln Thr Val Thr Ala His Thr
            580                 585                 590

Leu Gln Ala Met Pro Phe Lys Ala His Asp Leu Ile Gly Gly Lys Thr
        595                 600                 605

Val Ser Leu Asn Gln Asp Leu Thr Leu Gln Pro Tyr Gln Val Met Trp
610                 615                 620

Leu Glu Ile Ala
625

<210> SEQ ID NO 5
<211> LENGTH: 628
<212> TYPE: PRT
<213> ORGANISM: Neisseria polysaccharea
<220> FEATURE:
<221> NAME/KEY: VARIANT
<222> LOCATION: (290)..(290)
<223> OTHER INFORMATION: Xaa is chosen among A, C, D, G, I, K, L, M, R,
    V and W

<400> SEQUENCE: 5

Ser Pro Asn Ser Gln Tyr Leu Lys Thr Arg Ile Leu Asp Ile Tyr Thr
1               5                   10                  15

Pro Glu Gln Arg Ala Gly Ile Glu Lys Ser Glu Asp Trp Arg Gln Phe
            20                  25                  30

Ser Arg Arg Met Asp Thr His Pro Lys Leu Met Asn Glu Leu Asp
        35                  40                  45

```
Ser Val Tyr Gly Asn Asn Glu Ala Leu Leu Pro Met Leu Glu Met Leu
    50                  55                  60

Leu Ala Gln Ala Trp Gln Ser Tyr Ser Gln Arg Asn Ser Ser Leu Lys
65                  70                  75                  80

Asp Ile Asp Ile Ala Arg Glu Asn Asn Pro Asp Trp Ile Leu Ser Asn
                    85                  90                  95

Lys Gln Val Gly Gly Val Cys Tyr Val Asp Leu Phe Ala Gly Asp Leu
                100                 105                 110

Lys Gly Leu Lys Asp Lys Ile Pro Tyr Phe Gln Glu Leu Gly Leu Thr
            115                 120                 125

Tyr Leu His Leu Met Pro Leu Phe Lys Cys Pro Glu Gly Lys Ser Asp
    130                 135                 140

Gly Gly Tyr Ala Val Ser Ser Tyr Arg Asp Val Asn Pro Ala Leu Gly
145                 150                 155                 160

Thr Ile Gly Asp Leu Arg Glu Val Ile Ala Ala Leu His Glu Ala Gly
                165                 170                 175

Ile Ser Ala Val Val Asp Phe Ile Phe Asn His Thr Ser Asn Glu His
                180                 185                 190

Glu Trp Ala Gln Arg Cys Ala Ala Gly Asp Pro Leu Phe Asp Asn Phe
            195                 200                 205

Tyr Tyr Ile Phe Pro Asp Arg Arg Met Pro Asp Gln Tyr Asp Arg Thr
    210                 215                 220

Leu Arg Glu Ile Phe Pro Asp Gln His Pro Gly Gly Phe Ser Gln Leu
225                 230                 235                 240

Glu Asp Gly Arg Trp Val Trp Thr Thr Phe Asn Ser Phe Gln Trp Asp
                245                 250                 255

Leu Asn Tyr Ser Asn Pro Trp Val Phe Arg Ala Met Ala Gly Glu Met
                260                 265                 270

Leu Phe Leu Ala Asn Leu Gly Val Asp Ile Leu Arg Met Asp Ala Val
            275                 280                 285

Ala Xaa Ile Trp Lys Gln Met Gly Thr Ser Cys Glu Asn Leu Pro Gln
    290                 295                 300

Ala His Ala Leu Ile Arg Ala Phe Asn Ala Val Met Arg Ile Ala Ala
305                 310                 315                 320

Pro Ala Val Phe Phe Lys Ser Glu Ala Ile Val His Pro Asp Gln Val
                325                 330                 335

Val Gln Tyr Ile Gly Gln Asp Glu Cys Gln Ile Gly Tyr Asn Pro Leu
            340                 345                 350

Gln Met Ala Leu Leu Trp Asn Thr Leu Ala Thr Arg Glu Val Asn Leu
    355                 360                 365

Leu His Gln Ala Leu Thr Tyr Arg His Asn Leu Pro Glu His Thr Ala
    370                 375                 380

Trp Val Asn Tyr Val Arg Ser His Asp Asp Ile Gly Trp Thr Phe Ala
385                 390                 395                 400

Asp Glu Asp Ala Ala Tyr Leu Gly Ile Ser Gly Tyr Asp His Arg Gln
                405                 410                 415

Phe Leu Asn Arg Phe Phe Val Asn Arg Phe Asp Gly Ser Phe Ala Arg
            420                 425                 430

Gly Val Pro Phe Gln Tyr Asn Pro Ser Thr Gly Asp Cys Arg Val Ser
    435                 440                 445

Gly Thr Ala Ala Ala Leu Val Gly Leu Ala Gln Asp Asp Pro His Ala
450                 455                 460
```

```
Val Asp Arg Ile Lys Leu Leu Tyr Ser Ile Ala Leu Ser Thr Gly Gly
465                 470                 475                 480

Leu Pro Leu Ile Tyr Leu Gly Asp Glu Val Gly Thr Leu Asn Asp Asp
                485                 490                 495

Asp Trp Ser Gln Asp Ser Asn Lys Ser Asp Asp Ser Arg Trp Ala His
            500                 505                 510

Arg Pro Arg Tyr Asn Glu Ala Leu Tyr Ala Gln Arg Asn Asp Pro Ser
        515                 520                 525

Thr Ala Gly Gln Ile Tyr Gln Asp Leu Arg His Met Ile Ala Val
    530                 535                 540

Arg Gln Ser Asn Pro Arg Phe Asp Gly Gly Arg Leu Val Thr Phe Asn
545                 550                 555                 560

Thr Asn Asn Lys His Ile Ile Gly Tyr Ile Arg Asn Asn Ala Leu Leu
                565                 570                 575

Ala Phe Gly Asn Phe Ser Glu Tyr Pro Gln Thr Val Thr Ala His Thr
            580                 585                 590

Leu Gln Ala Met Pro Phe Lys Ala His Asp Leu Ile Gly Gly Lys Thr
        595                 600                 605

Val Ser Leu Asn Gln Asp Leu Thr Leu Gln Pro Tyr Gln Val Met Trp
610                 615                 620

Leu Glu Ile Ala
625

<210> SEQ ID NO 6
<211> LENGTH: 628
<212> TYPE: PRT
<213> ORGANISM: Neisseria polysaccharea
<220> FEATURE:
<221> NAME/KEY: VARIANT
<222> LOCATION: (331)..(331)
<223> OTHER INFORMATION: Xaa is chosen among C, G, Q, S and T

<400> SEQUENCE: 6

Ser Pro Asn Ser Gln Tyr Leu Lys Thr Arg Ile Leu Asp Ile Tyr Thr
1               5                   10                  15

Pro Glu Gln Arg Ala Gly Ile Glu Lys Ser Glu Asp Trp Arg Gln Phe
            20                  25                  30

Ser Arg Arg Met Asp Thr His Phe Pro Lys Leu Met Asn Glu Leu Asp
        35                  40                  45

Ser Val Tyr Gly Asn Asn Glu Ala Leu Leu Pro Met Leu Glu Met Leu
    50                  55                  60

Leu Ala Gln Ala Trp Gln Ser Tyr Ser Gln Arg Asn Ser Ser Leu Lys
65                  70                  75                  80

Asp Ile Asp Ile Ala Arg Glu Asn Asn Pro Asp Trp Ile Leu Ser Asn
                85                  90                  95

Lys Gln Val Gly Gly Val Cys Tyr Val Asp Leu Phe Ala Gly Asp Leu
            100                 105                 110

Lys Gly Leu Lys Asp Lys Ile Pro Tyr Phe Gln Glu Leu Gly Leu Thr
        115                 120                 125

Tyr Leu His Leu Met Pro Leu Phe Lys Cys Pro Glu Gly Lys Ser Asp
    130                 135                 140

Gly Gly Tyr Ala Val Ser Ser Tyr Arg Asp Val Asn Pro Ala Leu Gly
145                 150                 155                 160

Thr Ile Gly Asp Leu Arg Glu Val Ile Ala Ala Leu His Glu Ala Gly
                165                 170                 175

Ile Ser Ala Val Val Asp Phe Ile Phe Asn His Thr Ser Asn Glu His
```

```
              180                 185                 190
Glu Trp Ala Gln Arg Cys Ala Ala Gly Asp Pro Leu Phe Asp Asn Phe
            195                 200                 205
Tyr Tyr Ile Phe Pro Asp Arg Arg Met Pro Asp Gln Tyr Asp Arg Thr
            210                 215                 220
Leu Arg Glu Ile Phe Pro Asp Gln His Pro Gly Phe Ser Gln Leu
225                 230                 235                 240
Glu Asp Gly Arg Trp Val Trp Thr Thr Phe Asn Ser Phe Gln Trp Asp
            245                 250                 255
Leu Asn Tyr Ser Asn Pro Trp Val Phe Arg Ala Met Ala Gly Glu Met
            260                 265                 270
Leu Phe Leu Ala Asn Leu Gly Val Asp Ile Leu Arg Met Asp Ala Val
            275                 280                 285
Ala Phe Ile Trp Lys Gln Met Gly Thr Ser Cys Glu Asn Leu Pro Gln
            290                 295                 300
Ala His Ala Leu Ile Arg Ala Phe Asn Ala Val Met Arg Ile Ala Ala
305                 310                 315                 320
Pro Ala Val Phe Phe Lys Ser Glu Ala Ile Xaa His Pro Asp Gln Val
            325                 330                 335
Val Gln Tyr Ile Gly Gln Asp Glu Cys Gln Ile Gly Tyr Asn Pro Leu
            340                 345                 350
Gln Met Ala Leu Leu Trp Asn Thr Leu Ala Thr Arg Glu Val Asn Leu
            355                 360                 365
Leu His Gln Ala Leu Thr Tyr Arg His Asn Leu Pro Glu His Thr Ala
            370                 375                 380
Trp Val Asn Tyr Val Arg Ser His Asp Asp Ile Gly Trp Thr Phe Ala
385                 390                 395                 400
Asp Glu Asp Ala Ala Tyr Leu Gly Ile Ser Gly Tyr Asp His Arg Gln
            405                 410                 415
Phe Leu Asn Arg Phe Phe Val Asn Arg Phe Asp Gly Ser Phe Ala Arg
            420                 425                 430
Gly Val Pro Phe Gln Tyr Asn Pro Ser Thr Gly Asp Cys Arg Val Ser
            435                 440                 445
Gly Thr Ala Ala Ala Leu Val Gly Leu Ala Gln Asp Asp Pro His Ala
            450                 455                 460
Val Asp Arg Ile Lys Leu Leu Tyr Ser Ile Ala Leu Ser Thr Gly Gly
465                 470                 475                 480
Leu Pro Leu Ile Tyr Leu Gly Asp Glu Val Gly Thr Leu Asn Asp Asp
            485                 490                 495
Asp Trp Ser Gln Asp Ser Asn Lys Ser Asp Asp Ser Arg Trp Ala His
            500                 505                 510
Arg Pro Arg Tyr Asn Glu Ala Leu Tyr Ala Gln Arg Asn Asp Pro Ser
            515                 520                 525
Thr Ala Ala Gly Gln Ile Tyr Gln Asp Leu Arg His Met Ile Ala Val
            530                 535                 540
Arg Gln Ser Asn Pro Arg Phe Asp Gly Gly Arg Leu Val Thr Phe Asn
545                 550                 555                 560
Thr Asn Asn Lys His Ile Ile Gly Tyr Ile Arg Asn Asn Ala Leu Leu
            565                 570                 575
Ala Phe Gly Asn Phe Ser Glu Tyr Pro Gln Thr Val Thr Ala His Thr
            580                 585                 590
Leu Gln Ala Met Pro Phe Lys Ala His Asp Leu Ile Gly Gly Lys Thr
            595                 600                 605
```

```
Val Ser Leu Asn Gln Asp Leu Thr Leu Gln Pro Tyr Gln Val Met Trp
        610                 615                 620

Leu Glu Ile Ala
625

<210> SEQ ID NO 7
<211> LENGTH: 628
<212> TYPE: PRT
<213> ORGANISM: Neisseria polysaccharea
<220> FEATURE:
<221> NAME/KEY: VARIANT
<222> LOCATION: (394)..(394)
<223> OTHER INFORMATION: Xaa is chosen among A and G

<400> SEQUENCE: 7

Ser Pro Asn Ser Gln Tyr Leu Lys Thr Arg Ile Leu Asp Ile Tyr Thr
1               5                   10                  15

Pro Glu Gln Arg Ala Gly Ile Glu Lys Ser Glu Asp Trp Arg Gln Phe
            20                  25                  30

Ser Arg Arg Met Asp Thr His Phe Pro Lys Leu Met Asn Glu Leu Asp
        35                  40                  45

Ser Val Tyr Gly Asn Asn Glu Ala Leu Leu Pro Met Leu Glu Met Leu
    50                  55                  60

Leu Ala Gln Ala Trp Gln Ser Tyr Ser Gln Arg Asn Ser Ser Leu Lys
65                  70                  75                  80

Asp Ile Asp Ile Ala Arg Glu Asn Asn Pro Asp Trp Ile Leu Ser Asn
                85                  90                  95

Lys Gln Val Gly Gly Val Cys Tyr Val Asp Leu Phe Ala Gly Asp Leu
            100                 105                 110

Lys Gly Leu Lys Asp Lys Ile Pro Tyr Phe Gln Glu Leu Gly Leu Thr
        115                 120                 125

Tyr Leu His Leu Met Pro Leu Phe Lys Cys Pro Glu Gly Lys Ser Asp
    130                 135                 140

Gly Gly Tyr Ala Val Ser Ser Tyr Arg Asp Val Asn Pro Ala Leu Gly
145                 150                 155                 160

Thr Ile Gly Asp Leu Arg Glu Val Ile Ala Ala Leu His Glu Ala Gly
                165                 170                 175

Ile Ser Ala Val Val Asp Phe Ile Phe Asn His Thr Ser Asn Glu His
            180                 185                 190

Glu Trp Ala Gln Arg Cys Ala Ala Gly Asp Pro Leu Phe Asp Asn Phe
        195                 200                 205

Tyr Tyr Ile Phe Pro Asp Arg Arg Met Pro Asp Gln Tyr Asp Arg Thr
    210                 215                 220

Leu Arg Glu Ile Phe Pro Asp Gln His Pro Gly Gly Phe Ser Gln Leu
225                 230                 235                 240

Glu Asp Gly Arg Trp Val Trp Thr Thr Phe Asn Ser Phe Gln Trp Asp
                245                 250                 255

Leu Asn Tyr Ser Asn Pro Trp Val Phe Arg Ala Met Ala Gly Glu Met
            260                 265                 270

Leu Phe Leu Ala Asn Leu Gly Val Asp Ile Leu Arg Met Asp Ala Val
        275                 280                 285

Ala Phe Ile Trp Lys Gln Met Gly Thr Ser Cys Glu Asn Leu Pro Gln
    290                 295                 300

Ala His Ala Leu Ile Arg Ala Phe Asn Ala Val Met Arg Ile Ala Ala
305                 310                 315                 320
```

```
Pro Ala Val Phe Phe Lys Ser Glu Ala Ile Val His Pro Asp Gln Val
            325                 330                 335

Val Gln Tyr Ile Gly Gln Asp Glu Cys Gln Ile Gly Tyr Asn Pro Leu
        340                 345                 350

Gln Met Ala Leu Leu Trp Asn Thr Leu Ala Thr Arg Glu Val Asn Leu
            355                 360                 365

Leu His Gln Ala Leu Thr Tyr Arg His Asn Leu Pro Glu His Thr Ala
370                 375                 380

Trp Val Asn Tyr Val Arg Ser His Asp Xaa Ile Gly Trp Thr Phe Ala
385                 390                 395                 400

Asp Glu Asp Ala Ala Tyr Leu Gly Ile Ser Gly Tyr Asp His Arg Gln
            405                 410                 415

Phe Leu Asn Arg Phe Val Asn Arg Phe Asp Gly Ser Phe Ala Arg
        420                 425                 430

Gly Val Pro Phe Gln Tyr Asn Pro Ser Thr Gly Asp Cys Arg Val Ser
            435                 440                 445

Gly Thr Ala Ala Ala Leu Val Gly Leu Ala Gln Asp Asp Pro His Ala
450                 455                 460

Val Asp Arg Ile Lys Leu Leu Tyr Ser Ile Ala Leu Ser Thr Gly Gly
465                 470                 475                 480

Leu Pro Leu Ile Tyr Leu Gly Asp Glu Val Gly Thr Leu Asn Asp Asp
            485                 490                 495

Asp Trp Ser Gln Asp Ser Asn Lys Ser Asp Asp Ser Arg Trp Ala His
            500                 505                 510

Arg Pro Arg Tyr Asn Glu Ala Leu Tyr Ala Gln Arg Asn Asp Pro Ser
        515                 520                 525

Thr Ala Ala Gly Gln Ile Tyr Gln Asp Leu Arg His Met Ile Ala Val
    530                 535                 540

Arg Gln Ser Asn Pro Arg Phe Asp Gly Gly Arg Leu Val Thr Phe Asn
545                 550                 555                 560

Thr Asn Asn Lys His Ile Ile Gly Tyr Ile Arg Asn Asn Ala Leu Leu
                565                 570                 575

Ala Phe Gly Asn Phe Ser Glu Tyr Pro Gln Thr Val Thr Ala His Thr
            580                 585                 590

Leu Gln Ala Met Pro Phe Lys Ala His Asp Leu Ile Gly Gly Lys Thr
        595                 600                 605

Val Ser Leu Asn Gln Asp Leu Thr Leu Gln Pro Tyr Gln Val Met Trp
    610                 615                 620

Leu Glu Ile Ala
625

<210> SEQ ID NO 8
<211> LENGTH: 628
<212> TYPE: PRT
<213> ORGANISM: Neisseria polysaccharea

<400> SEQUENCE: 8

Ser Pro Asn Ser Gln Tyr Leu Lys Thr Arg Ile Leu Asp Ile Tyr Thr
1               5                   10                  15

Pro Glu Gln Arg Ala Gly Ile Glu Lys Ser Glu Asp Trp Arg Gln Phe
            20                  25                  30

Ser Arg Arg Met Asp Thr His Phe Pro Lys Leu Met Asn Glu Leu Asp
        35                  40                  45

Ser Val Tyr Gly Asn Asn Glu Ala Leu Leu Pro Met Leu Glu Met Leu
    50                  55                  60
```

```
Leu Ala Gln Ala Trp Gln Ser Tyr Ser Gln Arg Asn Ser Ser Leu Lys
 65                  70                  75                  80

Asp Ile Asp Ile Ala Arg Glu Asn Asn Pro Asp Trp Ile Leu Ser Asn
                 85                  90                  95

Lys Gln Val Gly Gly Val Cys Tyr Val Asp Leu Phe Ala Gly Asp Leu
            100                 105                 110

Lys Gly Leu Lys Asp Lys Ile Pro Tyr Phe Gln Glu Leu Gly Leu Thr
        115                 120                 125

Tyr Leu His Leu Met Pro Leu Phe Lys Cys Pro Glu Gly Lys Ser Asp
    130                 135                 140

Gly Gly Tyr Ala Val Ser Ser Tyr Arg Asp Val Asn Pro Ala Leu Gly
145                 150                 155                 160

Thr Ile Gly Asp Leu Arg Glu Val Ile Ala Ala Leu His Glu Ala Gly
                165                 170                 175

Ile Ser Ala Val Val Asp Phe Ile Phe Asn His Thr Ser Asn Glu His
            180                 185                 190

Glu Trp Ala Gln Arg Cys Ala Ala Gly Asp Pro Leu Phe Asp Asn Phe
        195                 200                 205

Tyr Tyr Ile Phe Pro Asp Arg Arg Met Pro Asp Gln Tyr Asp Arg Thr
    210                 215                 220

Leu Arg Glu Ile Phe Pro Asp Gln His Pro Gly Gly Phe Ser Gln Leu
225                 230                 235                 240

Glu Asp Gly Arg Trp Val Trp Thr Thr Phe Asn Ser Phe Gln Trp Asp
                245                 250                 255

Leu Asn Tyr Ser Asn Pro Trp Val Phe Arg Ala Met Ala Gly Glu Met
            260                 265                 270

Leu Phe Leu Ala Asn Leu Gly Val Asp Ile Leu Arg Met Asp Ala Val
        275                 280                 285

Ala Phe Ile Trp Lys Gln Met Gly Thr Ser Cys Glu Asn Leu Pro Gln
    290                 295                 300

Ala His Ala Leu Ile Arg Ala Phe Asn Ala Val Met Arg Ile Ala Ala
305                 310                 315                 320

Pro Ala Val Phe Phe Lys Ser Glu Ala Ile Val His Pro Asp Gln Val
                325                 330                 335

Val Gln Tyr Ile Gly Gln Asp Glu Cys Gln Ile Gly Tyr Asn Pro Leu
            340                 345                 350

Gln Met Ala Leu Leu Trp Asn Thr Leu Ala Thr Arg Glu Val Asn Leu
        355                 360                 365

Leu His Gln Ala Leu Thr Tyr Arg His Asn Leu Pro Glu His Thr Ala
    370                 375                 380

Trp Val Asn Tyr Val Arg Ser His Asp Asp Ile Gly Trp Thr Phe Ala
385                 390                 395                 400

Asp Glu Asp Ala Ala Tyr Leu Gly Ile Ser Gly Tyr Asp His Arg Gln
                405                 410                 415

Phe Leu Asn Arg Phe Phe Val Asn Arg Phe Asp Gly Ser Phe Ala Arg
            420                 425                 430

Gly Val Pro Phe Gln Tyr Asn Pro Ser Thr Gly Asp Cys Gln Val Ser
        435                 440                 445

Gly Thr Ala Ala Ala Leu Val Gly Leu Ala Gln Asp Pro His Ala
    450                 455                 460

Val Asp Arg Ile Lys Leu Leu Tyr Ser Ile Ala Leu Ser Thr Gly Gly
465                 470                 475                 480
```

```
Leu Pro Leu Ile Tyr Leu Gly Asp Glu Val Gly Thr Leu Asn Asp Asp
                    485                 490                 495

Asp Trp Ser Gln Asp Ser Asn Lys Ser Asp Ser Arg Trp Ala His
            500                 505                 510

Arg Pro Arg Tyr Asn Glu Ala Leu Tyr Ala Gln Arg Asn Asp Pro Ser
            515                 520                 525

Thr Ala Ala Gly Gln Ile Tyr Gln Asp Leu Arg His Met Ile Ala Val
        530                 535                 540

Arg Gln Ser Asn Pro Arg Phe Asp Gly Gly Arg Leu Val Thr Phe Asn
545                 550                 555                 560

Thr Asn Asn Lys His Ile Ile Gly Tyr Ile Arg Asn Asn Ala Leu Leu
                565                 570                 575

Ala Phe Gly Asn Phe Ser Glu Tyr Pro Gln Thr Val Thr Ala His Thr
            580                 585                 590

Leu Gln Ala Met Pro Phe Lys Ala His Asp Leu Ile Gly Gly Lys Thr
        595                 600                 605

Val Ser Leu Asn Gln Asp Leu Thr Leu Gln Pro Tyr Gln Val Met Trp
    610                 615                 620

Leu Glu Ile Ala
625

<210> SEQ ID NO 9
<211> LENGTH: 628
<212> TYPE: PRT
<213> ORGANISM: Neisseria polysaccharea
<220> FEATURE:
<221> NAME/KEY: VARIANT
<222> LOCATION: (290)..(290)
<223> OTHER INFORMATION: Xaa is chosen among C, I and L

<400> SEQUENCE: 9

Ser Pro Asn Ser Gln Tyr Leu Lys Thr Arg Ile Leu Asp Ile Tyr Thr
1               5                   10                  15

Pro Glu Gln Arg Ala Gly Ile Glu Lys Ser Glu Asp Trp Arg Gln Phe
            20                  25                  30

Ser Arg Arg Met Asp Thr His Phe Pro Lys Leu Met Asn Glu Leu Asp
        35                  40                  45

Ser Val Tyr Gly Asn Asn Glu Ala Leu Leu Pro Met Leu Glu Met Leu
    50                  55                  60

Leu Ala Gln Ala Trp Gln Ser Tyr Ser Gln Arg Asn Ser Ser Leu Lys
65                  70                  75                  80

Asp Ile Asp Ile Ala Arg Glu Asn Asn Pro Asp Trp Ile Leu Ser Asn
                85                  90                  95

Lys Gln Val Gly Gly Val Cys Tyr Val Asp Leu Phe Ala Gly Asp Leu
            100                 105                 110

Lys Gly Leu Lys Asp Lys Ile Pro Tyr Phe Gln Glu Leu Gly Leu Thr
        115                 120                 125

Tyr Leu His Leu Met Pro Leu Phe Lys Cys Pro Glu Gly Lys Ser Asp
    130                 135                 140

Gly Gly Tyr Ala Val Ser Ser Tyr Arg Asp Val Asn Pro Ala Leu Gly
145                 150                 155                 160

Thr Ile Gly Asp Leu Arg Glu Val Ile Ala Ala Leu His Glu Ala Gly
                165                 170                 175

Ile Ser Ala Val Val Asp Phe Ile Phe Asn His Thr Ser Asn Glu His
            180                 185                 190

Glu Trp Ala Gln Arg Cys Ala Ala Gly Asp Pro Leu Phe Asp Asn Phe
```

```
            195                 200                 205
Tyr Tyr Ile Phe Pro Asp Arg Arg Met Pro Asp Gln Tyr Asp Arg Thr
210                         215                 220

Leu Arg Glu Ile Phe Pro Asp Gln His Pro Gly Gly Phe Ser Gln Leu
225                 230                 235                 240

Glu Asp Gly Arg Trp Val Trp Thr Thr Phe Asn Ser Phe Gln Trp Asp
                        245                 250                 255

Leu Asn Tyr Ser Asn Pro Trp Val Phe Arg Ala Met Ala Gly Glu Met
                260                 265                 270

Leu Phe Leu Ala Asn Leu Gly Val Asp Ile Leu Arg Met Asp Ala Val
        275                 280                 285

Pro Xaa Ile Trp Lys Gln Met Gly Thr Ser Cys Glu Asn Leu Pro Gln
290                 295                 300

Ala His Ala Leu Ile Arg Ala Phe Asn Ala Val Met Arg Ile Ala Ala
305                 310                 315                 320

Pro Ala Val Phe Phe Lys Ser Glu Ala Ile Val His Pro Asp Gln Val
                        325                 330                 335

Val Gln Tyr Ile Gly Gln Asp Glu Cys Gln Ile Gly Tyr Asn Pro Leu
                340                 345                 350

Gln Met Ala Leu Leu Trp Asn Thr Leu Ala Thr Arg Glu Val Asn Leu
        355                 360                 365

Leu His Gln Ala Leu Thr Tyr Arg His Asn Leu Pro Glu His Thr Ala
370                 375                 380

Trp Val Asn Tyr Val Arg Ser His Asp Asp Ile Gly Trp Thr Phe Ala
385                 390                 395                 400

Asp Glu Asp Ala Ala Tyr Leu Gly Ile Ser Gly Tyr Asp His Arg Gln
                        405                 410                 415

Phe Leu Asn Arg Phe Phe Val Asn Arg Phe Asp Gly Ser Phe Ala Arg
                420                 425                 430

Gly Val Pro Phe Gln Tyr Asn Pro Ser Thr Gly Asp Cys Arg Val Ser
        435                 440                 445

Gly Thr Ala Ala Ala Leu Val Gly Leu Ala Gln Asp Asp Pro His Ala
450                 455                 460

Val Asp Arg Ile Lys Leu Leu Tyr Ser Ile Ala Leu Ser Thr Gly Gly
465                 470                 475                 480

Leu Pro Leu Ile Tyr Leu Gly Asp Glu Val Gly Thr Leu Asn Asp Asp
                        485                 490                 495

Asp Trp Ser Gln Asp Ser Asn Lys Ser Asp Asp Ser Arg Trp Ala His
                500                 505                 510

Arg Pro Arg Tyr Asn Glu Ala Leu Tyr Ala Gln Arg Asn Asp Pro Ser
        515                 520                 525

Thr Ala Ala Gly Gln Ile Tyr Gln Asp Leu Arg His Met Ile Ala Val
530                 535                 540

Arg Gln Ser Asn Pro Arg Phe Asp Gly Gly Arg Leu Val Thr Phe Asn
545                 550                 555                 560

Thr Asn Asn Lys His Ile Ile Gly Tyr Ile Arg Asn Asn Ala Leu Leu
                        565                 570                 575

Ala Phe Gly Asn Phe Ser Glu Tyr Pro Gln Thr Val Thr Ala His Thr
                580                 585                 590

Leu Gln Ala Met Pro Phe Lys Ala His Asp Leu Ile Gly Gly Lys Thr
        595                 600                 605

Val Ser Leu Asn Gln Asp Leu Thr Leu Gln Pro Tyr Gln Val Met Trp
610                 615                 620
```

Leu Glu Ile Ala
625

<210> SEQ ID NO 10
<211> LENGTH: 1299
<212> TYPE: PRT
<213> ORGANISM: Leuconostoc mesenteroides

<400> SEQUENCE: 10

Thr Gln Gln Val Ser Gly Lys Tyr Val Glu Lys Asp Gly Ser Trp Tyr
1               5                   10                  15

Tyr Tyr Phe Asp Asp Gly Lys Asn Ala Lys Gly Leu Ser Thr Ile Asp
            20                  25                  30

Asn Asn Ile Gln Tyr Phe Tyr Glu Ser Gly Lys Gln Ala Lys Gly Gln
        35                  40                  45

Tyr Val Thr Ile Asp Asn Gln Thr Tyr Tyr Phe Asp Lys Gly Ser Gly
    50                  55                  60

Asp Glu Leu Thr Gly Leu Gln Ser Ile Asp Gly Asn Ile Val Ala Phe
65                  70                  75                  80

Asn Asp Glu Gly Gln Gln Ile Phe Asn Gln Tyr Tyr Gln Ser Glu Asn
                85                  90                  95

Gly Thr Thr Tyr Tyr Phe Asp Asp Lys Gly His Ala Ala Thr Gly Ile
            100                 105                 110

Lys Asn Ile Glu Gly Lys Asn Tyr Tyr Phe Asp Asn Leu Gly Gln Leu
        115                 120                 125

Lys Lys Gly Phe Ser Gly Val Ile Asp Gly Gln Ile Met Thr Phe Asp
    130                 135                 140

Gln Glu Thr Gly Gln Glu Val Ser Asn Thr Thr Ser Glu Ile Lys Glu
145                 150                 155                 160

Gly Leu Thr Thr Gln Asn Thr Asp Tyr Ser Glu His Asn Ala Ala His
                165                 170                 175

Gly Thr Asp Ala Glu Asp Phe Glu Asn Ile Asp Gly Tyr Leu Thr Ala
            180                 185                 190

Ser Ser Trp Tyr Arg Pro Thr Gly Ile Leu Arg Asn Gly Thr Asp Trp
        195                 200                 205

Glu Pro Ser Thr Asp Thr Asp Phe Arg Pro Ile Leu Ser Val Trp Trp
    210                 215                 220

Pro Asp Lys Asn Thr Gln Val Asn Tyr Leu Asn Tyr Met Ala Asp Leu
225                 230                 235                 240

Gly Phe Ile Ser Asn Ala Asp Ser Phe Glu Thr Gly Asp Ser Gln Ser
                245                 250                 255

Leu Leu Asn Glu Ala Ser Asn Tyr Val Gln Lys Ser Ile Glu Met Lys
            260                 265                 270

Ile Ser Ala Gln Gln Ser Thr Glu Trp Leu Lys Asp Ala Met Ala Ala
        275                 280                 285

Phe Ile Val Ala Gln Pro Gln Trp Asn Glu Thr Ser Glu Asp Met Ser
    290                 295                 300

Asn Asp His Leu Gln Asn Gly Ala Leu Thr Tyr Val Asn Ser Pro Leu
305                 310                 315                 320

Thr Pro Asp Ala Asn Ser Asn Phe Arg Leu Leu Asn Arg Thr Pro Thr
                325                 330                 335

Asn Gln Thr Gly Glu Gln Ala Tyr Asn Leu Asp Asn Ser Lys Gly Gly
            340                 345                 350

Phe Glu Leu Leu Leu Ala Asn Gln Glu Asp Asn Ser Asn Val Val Val

```
                355                 360                 365
Glu Ala Glu Gln Leu Asn Trp Leu Tyr Tyr Leu Met Asn Phe Gly Thr
    370                 375                 380
Ile Thr Ala Asn Asp Ala Asp Ala Asn Phe Asp Gly Ile Arg Val Asp
385                 390                 395                 400
Ala Val Asp Asn Val Asp Ala Asp Leu Leu Gln Ile Ala Ala Asp Tyr
                405                 410                 415
Phe Lys Leu Ala Tyr Gly Val Asp Gln Asn Asp Ala Thr Ala Asn Gln
                420                 425                 430
His Leu Ser Ile Leu Glu Asp Trp Ser His Asn Asp Pro Leu Tyr Val
            435                 440                 445
Thr Asp Gln Gly Ser Asn Gln Leu Thr Met Asp Tyr Val His Thr
        450                 455                 460
Gln Leu Ile Trp Ser Leu Thr Lys Ser Ser Asp Ile Arg Gly Thr Met
465                 470                 475                 480
Gln Arg Phe Val Asp Tyr Tyr Met Val Asp Arg Ser Asn Asp Ser Thr
                485                 490                 495
Glu Asn Glu Ala Ile Pro Asn Tyr Ser Phe Val Arg Ala His Asp Cys
            500                 505                 510
Glu Val Gln Thr Val Ile Ala Gln Ile Val Ser Asp Leu Tyr Pro Asp
        515                 520                 525
Val Glu Asn Ser Leu Ala Pro Thr Thr Glu Gln Leu Ala Ala Ala Phe
    530                 535                 540
Lys Val Tyr Asn Glu Asp Glu Lys Leu Ala Asp Lys Lys Tyr Thr Gln
545                 550                 555                 560
Tyr Asn Met Ala Ser Ala Tyr Ala Met Leu Leu Thr Asn Lys Asp Thr
                565                 570                 575
Val Pro Arg Val Tyr Tyr Gly Asp Leu Tyr Thr Asp Asp Gly Gln Tyr
            580                 585                 590
Met Ala Thr Lys Ser Pro Tyr Tyr Asp Ala Ile Asn Thr Leu Leu Lys
        595                 600                 605
Ala Arg Val Gln Tyr Val Ala Gly Gly Gln Ser Met Ser Val Asp Ser
    610                 615                 620
Asn Asp Val Leu Thr Ser Val Arg Tyr Gly Lys Asp Ala Met Thr Ala
625                 630                 635                 640
Ser Asp Thr Gly Thr Ser Glu Thr Arg Thr Glu Gly Ile Gly Val Ile
                645                 650                 655
Val Ser Asn Asn Ala Glu Leu Gln Leu Glu Asp Gly His Thr Val Thr
            660                 665                 670
Leu His Met Gly Ala Ala His Lys Asn Gln Ala Tyr Arg Ala Leu Leu
        675                 680                 685
Ser Thr Thr Ala Asp Gly Leu Ala Tyr Tyr Asp Thr Asp Glu Asn Ala
    690                 695                 700
Pro Val Ala Tyr Thr Asp Ala Asn Gly Asp Leu Ile Phe Thr Asn Glu
705                 710                 715                 720
Ser Ile Tyr Gly Val Gln Asn Pro Gln Val Ser Gly Tyr Leu Ala Val
                725                 730                 735
Trp Val Pro Val Gly Ala Gln Gln Asp Gln Ala Arg Thr Ala Ser
            740                 745                 750
Asp Thr Thr Thr Asn Thr Ser Asp Lys Val Phe His Ser Asn Ala Ala
        755                 760                 765
Leu Asp Ser Gln Val Ile Tyr Glu Gly Phe Ser Asn Phe Gln Ala Phe
    770                 775                 780
```

```
Ala Thr Asp Ser Ser Glu Tyr Thr Asn Val Val Ile Ala Gln Asn Ala
785                 790                 795                 800

Asp Gln Phe Lys Gln Trp Gly Val Thr Ser Phe Gln Leu Ala Pro Gln
            805                 810                 815

Tyr Arg Ser Ser Thr Asp Thr Ser Phe Leu Asp Ser Ile Ile Gln Asn
        820                 825                 830

Gly Tyr Ala Phe Thr Asp Arg Tyr Asp Leu Gly Tyr Gly Thr Pro Thr
    835                 840                 845

Lys Tyr Gly Thr Ala Asp Gln Leu Arg Asp Ala Ile Lys Ala Leu His
850                 855                 860

Ala Ser Gly Ile Gln Ala Ile Ala Asp Trp Val Pro Asp Gln Ile Tyr
865                 870                 875                 880

Asn Leu Pro Glu Gln Glu Leu Ala Thr Val Thr Arg Thr Asn Ser Phe
            885                 890                 895

Gly Asp Asp Asp Thr Asp Ser Asp Ile Asp Asn Ala Leu Tyr Val Val
        900                 905                 910

Gln Ser Arg Gly Gly Gly Gln Tyr Gln Glu Met Tyr Gly Gly Ala Phe
    915                 920                 925

Leu Glu Glu Leu Gln Ala Leu Tyr Pro Ser Leu Phe Lys Val Asn Gln
930                 935                 940

Ile Ser Thr Gly Val Pro Ile Asp Gly Ser Val Lys Ile Thr Glu Trp
945                 950                 955                 960

Ala Ala Lys Tyr Phe Asn Gly Ser Asn Ile Gln Gly Lys Gly Ala Gly
            965                 970                 975

Tyr Val Leu Lys Asp Met Gly Ser Asn Lys Tyr Phe Lys Val Val Ser
        980                 985                 990

Asn Thr Glu Asp Gly Asp Tyr Leu Pro Lys Gln Leu Thr Asn Asp Leu
    995                 1000                1005

Ser Glu Thr Gly Phe Thr His Asp Asp Lys Gly Ile Ile Tyr Tyr
1010                1015                1020

Thr Leu Ser Gly Tyr Arg Ala Gln Asn Ala Phe Ile Gln Asp Asp
1025                1030                1035

Asp Asn Asn Tyr Tyr Tyr Phe Asp Lys Thr Gly His Leu Val Thr
1040                1045                1050

Gly Leu Gln Lys Ile Asn Asn His Thr Tyr Phe Phe Leu Pro Asn
1055                1060                1065

Gly Ile Glu Leu Val Lys Ser Phe Leu Gln Asn Glu Asp Gly Thr
1070                1075                1080

Ile Val Tyr Phe Asp Lys Lys Gly His Gln Val Phe Asp Gln Tyr
1085                1090                1095

Ile Thr Asp Gln Asn Gly Asn Ala Tyr Tyr Phe Asp Asp Ala Gly
1100                1105                1110

Val Met Leu Lys Ser Gly Leu Ala Thr Ile Asp Gly His Gln Gln
1115                1120                1125

Tyr Phe Asp Gln Asn Gly Val Gln Val Lys Asp Lys Phe Val Ile
1130                1135                1140

Gly Thr Asp Gly Tyr Lys Tyr Tyr Phe Glu Pro Gly Ser Gly Asn
1145                1150                1155

Leu Ala Ile Leu Arg Tyr Val Gln Asn Ser Lys Asn Gln Trp Phe
1160                1165                1170

Tyr Phe Asp Gly Asn Gly His Ala Val Thr Gly Phe Gln Thr Ile
1175                1180                1185
```

Asn Gly Lys Lys Gln Tyr Phe Tyr Asn Asp Gly His Gln Ser Lys
    1190                1195                1200

Gly Glu Phe Ile Asp Ala Asp Gly Asp Thr Phe Tyr Thr Ser Ala
    1205                1210                1215

Thr Asp Gly Arg Leu Val Thr Gly Val Gln Lys Ile Asn Gly Ile
    1220                1225                1230

Thr Tyr Ala Phe Asp Asn Thr Gly Asn Leu Ile Thr Asn Gln Tyr
    1235                1240                1245

Tyr Gln Leu Ala Asp Gly Lys Tyr Met Leu Leu Asp Asp Ser Gly
    1250                1255                1260

Arg Ala Lys Thr Gly Phe Val Leu Gln Asp Gly Val Leu Arg Tyr
    1265                1270                1275

Phe Asp Gln Asn Gly Glu Gln Val Lys Asp Ala Ile Ile Val Asp
    1280                1285                1290

Pro Asp Thr Asn Leu Ser
    1295

<210> SEQ ID NO 11
<211> LENGTH: 1877
<212> TYPE: PRT
<213> ORGANISM: Unknown
<220> FEATURE:
<223> OTHER INFORMATION: Unknown organism

<400> SEQUENCE: 11

Met Arg Gln Lys Glu Thr Ile Thr Arg Lys Lys Leu Tyr Lys Ser Gly
1               5                   10                  15

Lys Ser Trp Val Ala Ala Ala Thr Phe Ala Val Met Gly Val Ser
            20                  25                  30

Ala Val Thr Thr Val Ser Ala Asp Thr Gln Thr Pro Val Gly Thr Thr
            35                  40                  45

Gln Ser Gln Gln Asp Leu Thr Gly Gln Arg Gly Gln Asp Lys Pro Thr
        50                  55                  60

Thr Lys Glu Val Ile Asp Lys Lys Glu Pro Val Pro Gln Val Ser Ala
65                  70                  75                  80

Gln Asn Ala Gly Asp Leu Ser Asp Ala Lys Thr Thr Lys Ala Asp
                85                  90                  95

Asp Lys Gln Asp Thr Gln Pro Thr Asn Ala Gln Leu Pro Asp Gln Gly
            100                 105                 110

Asn Lys Gln Thr Asn Ser Asn Ser Asp Lys Gly Val Lys Glu Ser Thr
            115                 120                 125

Thr Ala Pro Val Lys Thr Thr Asp Val Pro Ser Lys Ser Val Thr Pro
        130                 135                 140

Glu Thr Asn Thr Ser Ile Asn Gly Gly Gln Tyr Val Glu Lys Asp Gly
145                 150                 155                 160

Gln Phe Val Tyr Ile Asp Gln Ser Gly Lys Gln Val Ser Gly Leu Gln
                165                 170                 175

Asn Ile Glu Gly His Thr Gln Tyr Phe Asp Pro Lys Thr Gly Tyr Gln
            180                 185                 190

Thr Lys Gly Glu Leu Lys Asn Ile Asp Asp Asn Ala Tyr Tyr Phe Asp
            195                 200                 205

Lys Asn Ser Gly Asn Gly Arg Thr Phe Thr Lys Ile Ser Asn Gly Ser
        210                 215                 220

Tyr Ser Glu Lys Asp Gly Met Trp Gln Tyr Val Asp Ser His Asp Lys
225                 230                 235                 240

```
Gln Pro Val Lys Gly Leu Tyr Asp Val Glu Gly Asn Leu Gln Tyr Phe
            245                 250                 255

Asp Leu Ser Thr Gly Asn Gln Ala Lys His Gln Ile Arg Ser Val Asp
            260                 265                 270

Gly Val Thr Tyr Tyr Phe Asp Ala Asp Ser Gly Asn Ala Thr Ala Phe
            275                 280                 285

Lys Ala Val Thr Asn Gly Arg Tyr Ala Glu Gln Thr Thr Lys Asp Lys
            290                 295                 300

Asp Gly Asn Glu Thr Ser Tyr Trp Ala Tyr Leu Asp Asn Gln Gly Asn
305                 310                 315                 320

Ala Ile Lys Gly Leu Asn Asp Val Asn Gly Glu Ile Gln Tyr Phe Asp
            325                 330                 335

Glu His Thr Gly Glu Gln Leu Lys Gly His Thr Ala Thr Leu Asp Gly
            340                 345                 350

Thr Thr Tyr Tyr Phe Glu Gly Asn Lys Gly Asn Leu Val Ser Val Val
            355                 360                 365

Asn Thr Ala Pro Thr Gly Gln Tyr Lys Ile Asn Gly Asp Asn Val Tyr
            370                 375                 380

Tyr Leu Asp Asn Asn Glu Ala Ile Lys Gly Leu Tyr Gly Ile Asn
385                 390                 395                 400

Gly Asn Leu Asn Tyr Phe Asp Leu Ala Thr Gly Ile Gln Leu Lys Gly
            405                 410                 415

Gln Ala Lys Asn Ile Asp Gly Ile Gly Tyr Tyr Phe Asp Lys Asp Thr
            420                 425                 430

Gly Asn Gly Ser Tyr Gln Tyr Thr Leu Met Ala Pro Ser Asn Lys Asn
            435                 440                 445

Asp Tyr Thr Gln His Asn Val Val Asn Asn Leu Ser Glu Ser Asn Phe
            450                 455                 460

Lys Asn Leu Val Asp Gly Phe Leu Thr Ala Glu Thr Trp Tyr Arg Pro
465                 470                 475                 480

Ala Gln Ile Leu Ser His Gly Thr Asp Trp Val Ala Ser Thr Asp Lys
            485                 490                 495

Asp Phe Arg Pro Leu Ile Thr Val Trp Trp Pro Asn Lys Asp Ile Gln
            500                 505                 510

Val Asn Tyr Leu Arg Leu Met Gln Asn Glu Gly Val Leu Asn Gln Ser
            515                 520                 525

Ala Val Tyr Asp Leu Asn Thr Asp Gln Leu Leu Asn Glu Ala Ala
            530                 535                 540

Gln Gln Ala Gln Ile Gly Ile Glu Lys Lys Ile Ser Gln Thr Gly Asn
545                 550                 555                 560

Thr Asp Trp Leu Asn Asn Val Leu Phe Thr Thr His Asp Gly Gln Pro
            565                 570                 575

Ser Phe Ile Lys Gln Gln Tyr Leu Trp Asn Ser Asp Ser Glu Tyr His
            580                 585                 590

Thr Gly Pro Phe Gln Gly Gly Tyr Leu Lys Tyr Gln Asn Ser Asp Leu
            595                 600                 605

Thr Pro Asn Val Asn Ser Lys Tyr Arg Asn Ala Asp Asn Ser Leu Asp
            610                 615                 620

Phe Leu Leu Ala Asn Asp Val Asp Asn Ser Asn Pro Ile Val Gln Ala
625                 630                 635                 640

Glu Asp Leu Asn Trp Leu Tyr Tyr Leu Leu Asn Phe Gly Ser Ile Thr
            645                 650                 655

Thr Gln Gly Lys Glu Asn Asn Ser Asn Phe Asp Ser Ile Arg Ile Asp
```

-continued

```
                660                 665                 670
Ala Val Asp Phe Val Ser Asn Asp Leu Ile Gln Arg Thr Tyr Asp Tyr
            675                 680                 685

Leu Arg Ala Ala Tyr Gly Val Asp Lys Asn Asp Lys Glu Ala Asn Ala
        690                 695                 700

His Leu Ser Leu Val Glu Ala Gly Leu Asp Ala Gly Thr Thr Thr Ile
705                 710                 715                 720

His Gln Asp Ala Leu Ile Glu Ser Asp Ile Arg Glu Ala Met Lys Lys
                725                 730                 735

Ser Leu Thr Asn Gly Pro Gly Ser Asn Ile Ser Leu Ser Asn Leu Ile
            740                 745                 750

Gln Asp Lys Glu Gly Asp Lys Leu Ile Ala Asp Arg Ala Asn Asn Ser
        755                 760                 765

Thr Glu Asn Val Ala Ile Pro Asn Tyr Ser Ile Ile His Ala His Asp
    770                 775                 780

Lys Asp Ile Gln Asp Lys Val Gly Ala Ala Ile Thr Asp Ala Thr Gly
785                 790                 795                 800

Ala Asp Trp Thr Asn Phe Thr Pro Glu Gln Leu Gln Lys Gly Leu Ser
                805                 810                 815

Leu Tyr Tyr Glu Asp Gln Arg Lys Ile Glu Lys Lys Tyr Asn Gln Tyr
            820                 825                 830

Asn Ile Pro Ser Ala Tyr Ala Leu Leu Leu Thr Asn Lys Asp Thr Val
        835                 840                 845

Pro Arg Val Tyr Tyr Gly Asp Met Tyr Gln Asp Gly Gln Tyr Met
    850                 855                 860

Gln Lys Gln Ser Leu Tyr Phe Asp Thr Ile Thr Ala Leu Met Glu Ala
865                 870                 875                 880

Arg Lys Gln Phe Val Ala Gly Gly Gln Thr Ile Asn Val Asp Asp Asn
                885                 890                 895

Gly Val Leu Thr Ser Val Arg Phe Gly Lys Gly Ala Met Thr Ala Asn
            900                 905                 910

Asp Ile Gly Thr Asn Glu Thr Arg Thr Gln Gly Ile Gly Val Val Ile
        915                 920                 925

Ala Asn Asp Pro Ser Leu Lys Leu Ser Lys Asp Ser Lys Val Thr Leu
    930                 935                 940

His Met Gly Ala Ala His Arg Asn Gln Asn Tyr Arg Ala Leu Leu Leu
945                 950                 955                 960

Thr Thr Asp Asn Gly Ile Asp Ser Tyr Ser Ser Ser Lys Asn Ala Pro
                965                 970                 975

Val Ile Lys Thr Asp Asp Asn Gly Asp Leu Val Phe Ser Asn Gln Asp
            980                 985                 990

Ile Asn Asp Gln Leu Asn Thr Lys Val His Gly Phe Leu Asn Ser Glu
        995                 1000                1005

Val Ser Gly Tyr Leu Ser Ala Trp Val Pro Leu Asp Ala Thr Glu
    1010                1015                1020

Gln Gln Asp Ala Arg Thr Leu Pro Ser Glu Lys Ser Val Asn Asp
    1025                1030                1035

Gly Lys Val Leu His Ser Asn Ala Ala Leu Asp Ser Asn Leu Ile
    1040                1045                1050

Tyr Glu Ala Phe Ser Asn Phe Gln Pro Met Pro Thr Asn Arg Asn
    1055                1060                1065

Glu Tyr Thr Asn Val Val Ile Ala Asp Lys Ala Asp Thr Phe Lys
    1070                1075                1080
```

-continued

Ser Trp Gly Ile Thr Ser Phe Glu Met Ala Pro Gln Tyr Arg Ser
1085              1090                1095

Ser Gln Asp Lys Thr Phe Leu Asp Ser Thr Ile Asp Asn Gly Tyr
1100              1105                1110

Ala Phe Thr Asp Arg Tyr Asp Leu Gly Phe Glu Lys Pro Thr Lys
1115              1120                1125

Tyr Gly Asn Asp Glu Asp Leu Arg Gln Ala Ile Lys Gln Leu His
1130              1135                1140

Ser Ser Gly Met Gln Val Met Ala Asp Val Val Ala Asn Gln Ile
1145              1150                1155

Tyr Asn Leu Pro Gly Lys Glu Val Ala Ser Thr Asn Arg Val Asp
1160              1165                1170

Trp Asn Gly Asn Asn Leu Ser Thr Pro Phe Gly Thr Gln Met Tyr
1175              1180                1185

Val Val Asn Thr Val Gly Gly Gly Lys Tyr Gln Asn Lys Tyr Gly
1190              1195                1200

Gly Glu Phe Leu Asp Lys Leu Lys Ala Ala Tyr Pro Asp Ile Phe
1205              1210                1215

Arg Ser Lys Asn Tyr Glu Tyr Asp Val Lys Asn Tyr Gly Gly Asn
1220              1225                1230

Gly Thr Gly Ser Val Tyr Tyr Thr Val Asp Ser Lys Thr Arg Ala
1235              1240                1245

Glu Leu Asp Thr Asp Thr Lys Ile Lys Glu Trp Ser Ala Lys Tyr
1250              1255                1260

Met Asn Gly Thr Asn Val Leu Gly Leu Gly Met Gly Tyr Val Leu
1265              1270                1275

Lys Asp Trp Gln Thr Gly Gln Tyr Phe Asn Val Ser Asn Gln Asn
1280              1285                1290

Met Lys Phe Leu Leu Pro Ser Asp Leu Ile Ser Asn Asp Ile Thr
1295              1300                1305

Val Gln Leu Gly Val Pro Val Thr Asp Lys Lys Ile Ile Phe Asp
1310              1315                1320

Pro Ala Ser Ala Tyr Asn Met Tyr Ser Asn Leu Pro Glu Asp Met
1325              1330                1335

Gln Val Met Asp Tyr Gln Asp Lys Lys Ser Thr Pro Ser Ile
1340              1345                1350

Lys Pro Leu Ser Ser Tyr Asn Asn Lys Gln Val Gln Val Thr Arg
1355              1360                1365

Gln Tyr Thr Asp Ser Lys Gly Val Ser Trp Asn Leu Ile Thr Phe
1370              1375                1380

Ala Gly Gly Asp Leu Gln Gly Gln Lys Leu Trp Val Asp Ser Arg
1385              1390                1395

Ala Leu Thr Met Thr Pro Phe Lys Thr Met Asn Gln Ile Ser Phe
1400              1405                1410

Ile Ser Tyr Ala Asn Arg Asn Asp Gly Leu Phe Leu Asn Ala Pro
1415              1420                1425

Tyr Gln Val Lys Gly Tyr Gln Leu Ala Gly Met Ser Asn Gln Tyr
1430              1435                1440

Lys Gly Gln Gln Val Thr Ile Ala Gly Val Ala Asn Val Ser Gly
1445              1450                1455

Lys Asp Trp Ser Leu Ile Ser Phe Asn Gly Thr Gln Tyr Trp Ile
1460              1465                1470

```
Asp Ser Gln Ala Leu Asn Thr Asn Phe Thr His Asp Met Asn Gln
1475                1480                1485

Lys Val Phe Val Asn Thr Thr Ser Asn Leu Asp Gly Leu Phe Leu
    1490                1495                1500

Asn Ala Pro Tyr Arg Gln Pro Gly Tyr Lys Leu Ala Gly Leu Ala
    1505                1510                1515

Lys Asn Tyr Asn Asn Gln Thr Val Thr Val Ser Gln Gln Tyr Phe
    1520                1525                1530

Asp Asp Gln Gly Thr Val Trp Ser Gln Val Val Leu Gly Gly Gln
    1535                1540                1545

Thr Val Trp Val Asp Asn His Ala Leu Ala Gln Met Gln Val Arg
    1550                1555                1560

Asp Thr Asn Gln Gln Leu Tyr Val Asn Ser Asn Gly Arg Asn Asp
    1565                1570                1575

Gly Leu Phe Leu Asn Ala Pro Tyr Arg Gly Gln Gly Ser Gln Leu
    1580                1585                1590

Ile Gly Met Thr Ala Asp Tyr Asn Gly Gln His Val Gln Val Thr
    1595                1600                1605

Lys Gln Gly Gln Asp Ala Tyr Gly Ala Gln Trp Arg Leu Ile Thr
    1610                1615                1620

Leu Asn Asn Gln Gln Val Trp Val Asp Ser Arg Ala Leu Ser Thr
    1625                1630                1635

Thr Ile Met Gln Ala Met Asn Asp Asp Met Tyr Val Asn Ser Ser
    1640                1645                1650

Gln Arg Thr Asp Gly Leu Trp Leu Asn Ala Pro Tyr Thr Met Ser
    1655                1660                1665

Gly Ala Lys Trp Ala Gly Asp Thr Arg Ser Ala Asn Gly Arg Tyr
    1670                1675                1680

Val His Ile Ser Lys Ala Tyr Ser Asn Glu Val Gly Asn Thr Tyr
    1685                1690                1695

Tyr Leu Thr Asn Leu Asn Gly Gln Ser Thr Trp Ile Asp Lys Arg
    1700                1705                1710

Ala Phe Thr Ala Thr Phe Asp Gln Val Val Ala Leu Asn Ala Thr
    1715                1720                1725

Ile Val Ala Arg Gln Arg Pro Asp Gly Met Phe Lys Thr Ala Pro
    1730                1735                1740

Tyr Gly Glu Ala Gly Ala Gln Phe Val Asp Tyr Val Thr Asn Tyr
    1745                1750                1755

Asn Gln Gln Thr Val Pro Val Thr Lys Gln His Ser Asp Ala Gln
    1760                1765                1770

Gly Asn Gln Trp Tyr Leu Ala Thr Val Asn Gly Thr Gln Tyr Trp
    1775                1780                1785

Ile Asp Gln Arg Ser Phe Ser Pro Val Val Thr Lys Val Val Asp
    1790                1795                1800

Tyr Gln Ala Lys Ile Val Pro Arg Thr Thr Arg Asp Gly Val Phe
    1805                1810                1815

Ser Gly Ala Pro Tyr Gly Glu Val Asn Ala Lys Leu Val Asn Met
    1820                1825                1830

Ala Thr Ala Tyr Gln Asn Gln Val Val His Ala Thr Gly Glu Tyr
    1835                1840                1845

Thr Asn Ala Ser Gly Ile Thr Trp Ser Gln Phe Ala Leu Ser Gly
    1850                1855                1860

Gln Glu Asp Lys Leu Trp Ile Asp Lys Arg Ala Leu Gln Ala
```

<210> SEQ ID NO 12
<211> LENGTH: 1125
<212> TYPE: PRT
<213> ORGANISM: Leuconostoc mesenteroides
<220> FEATURE:
<221> NAME/KEY: VARIANT
<222> LOCATION: (403)..(403)
<223> OTHER INFORMATION: Xaa in position 403 is chosen among G, S, V, C, F, N, I, L and W
<220> FEATURE:
<221> NAME/KEY: VARIANT
<222> LOCATION: (404)..(404)
<223> OTHER INFORMATION: Xaa in position 404 is chosen among L, I, H, Y and F
<220> FEATURE:
<221> NAME/KEY: VARIANT
<222> LOCATION: (430)..(430)
<223> OTHER INFORMATION: Xaa in position 430 is chosen among A and E
<220> FEATURE:
<221> NAME/KEY: VARIANT
<222> LOCATION: (431)..(431)
<223> OTHER INFORMATION: Xaa in position 431 is chosen among A, F, R, D, N, C ,E, Q, G, H, I, L, K, M, P, S, T, W, Y and V
<220> FEATURE:
<221> NAME/KEY: VARIANT
<222> LOCATION: (434)..(434)
<223> OTHER INFORMATION: Xaa in position 434 is chosen among A, R, D, N, C, E, Q, G, H, I, K, L, M, F, P, S, T, W, Y and V

<400> SEQUENCE: 12

Met Ala His His His His His His Val Thr Ser Leu Tyr Lys Lys Ala
1               5                   10                  15

Gly Ser Ala Ala Ala Pro Phe Thr Met Ala Gln Ala Gly His Tyr Ile
            20                  25                  30

Thr Lys Asn Gly Asn Asp Trp Gln Tyr Asp Thr Asn Gly Glu Leu Ala
        35                  40                  45

Lys Gly Leu Arg Gln Asp Ser Asn Gly Lys Leu Arg Tyr Phe Asp Leu
    50                  55                  60

Thr Thr Gly Ile Gln Ala Lys Gly Gln Phe Val Thr Ile Gly Gln Glu
65                  70                  75                  80

Thr Tyr Tyr Phe Ser Lys Asp His Gly Asp Ala Gln Leu Leu Pro Met
                85                  90                  95

Val Thr Glu Gly His Tyr Gly Thr Ile Thr Leu Lys Gln Gly Gln Asp
            100                 105                 110

Thr Lys Thr Ala Trp Val Tyr Arg Asp Gln Asn Asn Thr Ile Leu Lys
        115                 120                 125

Gly Leu Gln Asn Ile Asn Gly Thr Leu Gln Phe Phe Asp Pro Tyr Thr
130                 135                 140

Gly Glu Gln Leu Lys Gly Gly Val Ala Lys Tyr Asp Asp Lys Leu Phe
145                 150                 155                 160

Tyr Phe Glu Ser Gly Lys Gly Asn Leu Val Ser Thr Val Ala Gly Asp
                165                 170                 175

Tyr Gln Asp Gly His Tyr Ile Ser Gln Asp Gly Gln Thr Arg Tyr Ala
            180                 185                 190

Asp Lys Gln Asn Gln Leu Val Lys Gly Leu Val Thr Val Asn Gly Ala
        195                 200                 205

Leu Gln Tyr Phe Asp Asn Ala Thr Gly Asn Gln Ile Lys Asn Gln Gln
210                 215                 220

Val Ile Val Asp Gly Lys Thr Tyr Tyr Phe Asp Asp Lys Gly Asn Gly
225                 230                 235                 240

-continued

Glu Tyr Leu Phe Thr Asn Thr Leu Asp Met Ser Thr Asn Ala Phe Ser
            245                 250                 255

Thr Lys Asn Val Ala Phe Asn His Asp Ser Ser Phe Asp His Thr
        260                 265                 270

Val Asp Gly Phe Leu Thr Ala Asp Thr Trp Tyr Arg Pro Lys Ser Ile
            275                 280                 285

Leu Ala Asn Gly Thr Thr Trp Arg Asp Ser Thr Asp Lys Asp Met Arg
290                 295                 300

Pro Leu Ile Thr Val Trp Trp Pro Asn Lys Asn Val Gln Val Asn Tyr
305                 310                 315                 320

Leu Asn Phe Met Lys Ala Asn Gly Leu Leu Thr Thr Ala Ala Gln Tyr
                325                 330                 335

Thr Leu His Ser Asp Gln Tyr Asp Leu Asn Gln Ala Ala Gln Asp Val
            340                 345                 350

Gln Val Ala Ile Glu Arg Arg Ile Ala Ser Glu His Gly Thr Asp Trp
        355                 360                 365

Leu Gln Lys Leu Leu Phe Glu Ser Gln Asn Asn Pro Ser Phe Val
370                 375                 380

Lys Gln Gln Phe Ile Trp Asn Lys Asp Ser Glu Tyr His Gly Gly Gly
385                 390                 395                 400

Asp Ala Xaa Xaa Gln Gly Gly Tyr Leu Lys Tyr Gly Asn Asn Pro Leu
                405                 410                 415

Thr Pro Thr Thr Asn Ser Asp Tyr Arg Gln Pro Gly Asn Xaa Xaa Asp
            420                 425                 430

Phe Xaa Leu Ala Asn Asp Val Asp Asn Ser Asn Pro Val Val Gln Ala
        435                 440                 445

Glu Asn Leu Asn Trp Leu His Tyr Leu Met Asn Phe Gly Thr Ile Thr
450                 455                 460

Ala Gly Gln Asp Asp Ala Asn Phe Asp Ser Ile Arg Ile Asp Ala Val
465                 470                 475                 480

Asp Phe Ile His Asn Asp Thr Ile Gln Arg Thr Tyr Asp Tyr Leu Arg
                485                 490                 495

Asp Ala Tyr Gln Val Gln Gln Ser Glu Ala Lys Ala Asn Gln His Ile
            500                 505                 510

Ser Leu Val Glu Ala Gly Leu Asp Ala Gly Thr Ser Thr Ile His Asn
        515                 520                 525

Asp Ala Leu Ile Glu Ser Asn Leu Arg Glu Ala Ala Thr Leu Ser Leu
530                 535                 540

Thr Asn Glu Pro Gly Lys Asn Lys Pro Leu Thr Asn Met Leu Gln Asp
545                 550                 555                 560

Val Asp Gly Gly Thr Leu Ile Thr Asp His Thr Gln Asn Ser Thr Glu
                565                 570                 575

Asn Gln Ala Thr Pro Asn Tyr Ser Ile Ile His Ala His Asp Lys Gly
            580                 585                 590

Val Gln Glu Lys Val Gly Ala Ala Ile Thr Asp Ala Thr Gly Ala Asp
        595                 600                 605

Trp Thr Asn Phe Thr Asp Glu Gln Leu Lys Ala Gly Leu Glu Leu Phe
610                 615                 620

Tyr Lys Asp Gln Arg Ala Thr Asn Lys Lys Tyr Asn Ser Tyr Asn Ile
625                 630                 635                 640

Pro Ser Ile Tyr Ala Leu Met Leu Thr Asn Lys Asp Thr Val Pro Arg
                645                 650                 655

Met Tyr Tyr Gly Asp Met Tyr Gln Asp Asp Gly Gln Tyr Met Ala Asn

-continued

```
                660             665             670
Lys Ser Ile Tyr Tyr Asp Ala Leu Val Ser Leu Met Thr Ala Arg Lys
            675             680             685
Ser Tyr Val Ser Gly Gly Gln Thr Met Ser Val Asp Asn His Gly Leu
690             695             700
Leu Lys Ser Val Arg Phe Gly Lys Asp Ala Met Thr Ala Asn Asp Leu
705             710             715             720
Gly Thr Ser Ala Thr Arg Thr Glu Gly Leu Gly Val Ile Ile Gly Asn
                725             730             735
Asp Pro Lys Leu Gln Leu Asn Asp Ser Asp Lys Val Thr Leu Asp Met
            740             745             750
Gly Ala Ala His Lys Asn Gln Lys Tyr Arg Ala Val Ile Leu Thr Thr
            755             760             765
Arg Asp Gly Leu Ala Thr Phe Asn Ser Asp Gln Ala Pro Thr Ala Trp
            770             775             780
Thr Asn Asp Gln Gly Thr Leu Thr Phe Ser Asn Gln Glu Ile Asn Gly
785             790             795             800
Gln Asp Asn Thr Gln Ile Arg Gly Val Ala Asn Pro Gln Val Ser Gly
                805             810             815
Tyr Leu Ala Val Trp Val Pro Val Gly Ala Ser Asp Asn Gln Asp Ala
                820             825             830
Arg Thr Ala Ala Thr Thr Thr Glu Asn His Asp Gly Lys Val Leu His
                835             840             845
Ser Asn Ala Ala Leu Asp Ser Asn Leu Ile Tyr Glu Gly Phe Ser Asn
850             855             860
Phe Gln Pro Lys Ala Thr Thr His Asp Glu Leu Thr Asn Val Val Ile
865             870             875             880
Ala Lys Asn Ala Asp Val Phe Asn Asn Trp Gly Ile Thr Ser Phe Glu
                885             890             895
Met Ala Pro Gln Tyr Arg Ser Ser Gly Asp His Thr Phe Leu Asp Ser
                900             905             910
Thr Ile Asp Asn Gly Tyr Ala Phe Thr Asp Arg Tyr Asp Leu Gly Phe
            915             920             925
Asn Thr Pro Thr Lys Tyr Gly Thr Asp Gly Asp Leu Arg Ala Thr Ile
            930             935             940
Gln Ala Leu His His Ala Asn Met Gln Val Met Ala Asp Val Val Asp
945             950             955             960
Asn Gln Val Tyr Asn Leu Pro Gly Lys Glu Val Val Ser Ala Thr Arg
                965             970             975
Ala Gly Val Tyr Gly Asn Asp Asp Ala Thr Gly Phe Gly Thr Gln Leu
            980             985             990
Tyr Val Thr Asn Ser Val Gly Gly Gly Gln Tyr Gln Glu Lys Tyr Ala
                995             1000            1005
Gly Gln Tyr Leu Glu Ala Leu Lys Ala Lys Tyr Pro Asp Leu Phe
            1010            1015            1020
Glu Gly Lys Ala Tyr Asp Tyr Trp Tyr Lys Asn Tyr Ala Asn Asp
            1025            1030            1035
Gly Ser Asn Pro Tyr Tyr Thr Leu Ser His Gly Asp Arg Glu Ser
            1040            1045            1050
Ile Pro Ala Asp Val Ala Ile Lys Gln Trp Ser Ala Lys Tyr Met
            1055            1060            1065
Asn Gly Thr Asn Val Leu Gly Asn Gly Met Gly Tyr Val Leu Lys
            1070            1075            1080
```

Asp Trp His Asn Gly Gln Tyr Phe Lys Leu Asp Gly Asp Lys Ser
    1085                1090                1095

Thr Leu Pro Lys Gly Gly Arg Ala Asp Pro Ala Phe Leu Tyr Lys
    1100                1105                1110

Val Val Ser Ala Trp Ser His Pro Gln Phe Glu Lys
    1115                1120                1125

<210> SEQ ID NO 13
<211> LENGTH: 1125
<212> TYPE: PRT
<213> ORGANISM: Leuconostoc mesenteroides

<400> SEQUENCE: 13

Met Ala His His His His His His Val Thr Ser Leu Tyr Lys Lys Ala
1               5                   10                  15

Gly Ser Ala Ala Ala Pro Phe Thr Met Ala Gln Ala Gly His Tyr Ile
            20                  25                  30

Thr Lys Asn Gly Asn Asp Trp Gln Tyr Asp Thr Asn Gly Glu Leu Ala
        35                  40                  45

Lys Gly Leu Arg Gln Asp Ser Asn Gly Lys Leu Arg Tyr Phe Asp Leu
    50                  55                  60

Thr Thr Gly Ile Gln Ala Lys Gly Gln Phe Val Thr Ile Gly Gln Glu
65                  70                  75                  80

Thr Tyr Tyr Phe Ser Lys Asp His Gly Asp Ala Gln Leu Leu Pro Met
                85                  90                  95

Val Thr Glu Gly His Tyr Gly Thr Ile Thr Leu Lys Gln Gly Gln Asp
            100                 105                 110

Thr Lys Thr Ala Trp Val Tyr Arg Asp Gln Asn Asn Thr Ile Leu Lys
        115                 120                 125

Gly Leu Gln Asn Ile Asn Gly Thr Leu Gln Phe Phe Asp Pro Tyr Thr
    130                 135                 140

Gly Glu Gln Leu Lys Gly Gly Val Ala Lys Tyr Asp Asp Lys Leu Phe
145                 150                 155                 160

Tyr Phe Glu Ser Gly Lys Gly Asn Leu Val Ser Thr Val Ala Gly Asp
                165                 170                 175

Tyr Gln Asp Gly His Tyr Ile Ser Gln Asp Gly Gln Thr Arg Tyr Ala
            180                 185                 190

Asp Lys Gln Asn Gln Leu Val Lys Gly Leu Val Thr Val Asn Gly Ala
        195                 200                 205

Leu Gln Tyr Phe Asp Asn Ala Thr Gly Asn Gln Ile Lys Asn Gln Gln
    210                 215                 220

Val Ile Val Asp Gly Lys Thr Tyr Tyr Phe Asp Asp Lys Gly Asn Gly
225                 230                 235                 240

Glu Tyr Leu Phe Thr Asn Thr Leu Asp Met Ser Thr Asn Ala Phe Ser
                245                 250                 255

Thr Lys Asn Val Ala Phe Asn His Asp Ser Ser Phe Asp His Thr
            260                 265                 270

Val Asp Gly Phe Leu Thr Ala Asp Thr Trp Tyr Arg Pro Lys Ser Ile
        275                 280                 285

Leu Ala Asn Gly Thr Thr Trp Arg Asp Ser Thr Asp Lys Asp Met Arg
    290                 295                 300

Pro Leu Ile Thr Val Trp Trp Pro Asn Lys Asn Val Gln Val Asn Tyr
305                 310                 315                 320

Leu Asn Phe Met Lys Ala Asn Gly Leu Leu Thr Thr Ala Ala Gln Tyr

-continued

```
                325                 330                 335
Thr Leu His Ser Asp Gln Tyr Asp Leu Asn Gln Ala Ala Gln Asp Val
                340                 345                 350
Gln Val Ala Ile Glu Arg Arg Ile Ala Ser Glu His Gly Thr Asp Trp
                355                 360                 365
Leu Gln Lys Leu Leu Phe Glu Ser Gln Asn Asn Pro Ser Phe Val
                370                 375                 380
Lys Gln Gln Phe Ile Trp Asn Lys Asp Ser Glu Tyr His Gly Gly Gly
385                 390                 395                 400
Asp Ala Trp Phe Gln Gly Gly Tyr Leu Lys Tyr Gly Asn Asn Pro Leu
                405                 410                 415
Thr Pro Thr Thr Asn Ser Asp Tyr Arg Gln Pro Gly Asn Ala Ile Glu
                420                 425                 430
Phe Ile Leu Ala Asn Asp Val Asp Asn Ser Asn Pro Val Val Gln Ala
                435                 440                 445
Glu Asn Leu Asn Trp Leu His Tyr Leu Met Asn Phe Gly Thr Ile Thr
                450                 455                 460
Ala Gly Gln Asp Asp Ala Asn Phe Asp Ser Ile Arg Ile Asp Ala Val
465                 470                 475                 480
Asp Phe Ile His Asn Asp Thr Ile Gln Arg Thr Tyr Asp Tyr Leu Arg
                485                 490                 495
Asp Ala Tyr Gln Val Gln Gln Ser Glu Ala Lys Ala Asn Gln His Ile
                500                 505                 510
Ser Leu Val Glu Ala Gly Leu Asp Ala Gly Thr Ser Thr Ile His Asn
                515                 520                 525
Asp Ala Leu Ile Glu Ser Asn Leu Arg Glu Ala Ala Thr Leu Ser Leu
                530                 535                 540
Thr Asn Glu Pro Gly Lys Asn Lys Pro Leu Thr Asn Met Leu Gln Asp
545                 550                 555                 560
Val Asp Gly Gly Thr Leu Ile Thr Asp His Thr Gln Asn Ser Thr Glu
                565                 570                 575
Asn Gln Ala Thr Pro Asn Tyr Ser Ile Ile His Ala His Asp Lys Gly
                580                 585                 590
Val Gln Glu Lys Val Gly Ala Ala Ile Thr Asp Ala Thr Gly Ala Asp
                595                 600                 605
Trp Thr Asn Phe Thr Asp Glu Gln Leu Lys Ala Gly Leu Glu Leu Phe
                610                 615                 620
Tyr Lys Asp Gln Arg Ala Thr Asn Lys Lys Tyr Asn Ser Tyr Asn Ile
625                 630                 635                 640
Pro Ser Ile Tyr Ala Leu Met Leu Thr Asn Lys Asp Thr Val Pro Arg
                645                 650                 655
Met Tyr Tyr Gly Asp Met Tyr Gln Asp Gly Gln Tyr Met Ala Asn
                660                 665                 670
Lys Ser Ile Tyr Tyr Asp Ala Leu Val Ser Leu Met Thr Ala Arg Lys
                675                 680                 685
Ser Tyr Val Ser Gly Gly Gln Thr Met Ser Val Asp Asn His Gly Leu
                690                 695                 700
Leu Lys Ser Val Arg Phe Gly Lys Asp Ala Met Thr Ala Asn Asp Leu
705                 710                 715                 720
Gly Thr Ser Ala Thr Arg Thr Glu Gly Leu Gly Val Ile Ile Gly Asn
                725                 730                 735
Asp Pro Lys Leu Gln Leu Asn Asp Ser Asp Lys Val Thr Leu Asp Met
                740                 745                 750
```

-continued

Gly Ala Ala His Lys Asn Gln Lys Tyr Arg Ala Val Ile Leu Thr Thr
             755                 760                 765

Arg Asp Gly Leu Ala Thr Phe Asn Ser Asp Gln Ala Pro Thr Ala Trp
770                 775                 780

Thr Asn Asp Gln Gly Thr Leu Thr Phe Ser Asn Gln Glu Ile Asn Gly
785                 790                 795                 800

Gln Asp Asn Thr Gln Ile Arg Gly Val Ala Asn Pro Gln Val Ser Gly
            805                 810                 815

Tyr Leu Ala Val Trp Val Pro Val Gly Ala Ser Asp Asn Gln Asp Ala
                820                 825                 830

Arg Thr Ala Ala Thr Thr Thr Glu Asn His Asp Gly Lys Val Leu His
            835                 840                 845

Ser Asn Ala Ala Leu Asp Ser Asn Leu Ile Tyr Glu Gly Phe Ser Asn
850                 855                 860

Phe Gln Pro Lys Ala Thr Thr His Asp Glu Leu Thr Asn Val Val Ile
865                 870                 875                 880

Ala Lys Asn Ala Asp Val Phe Asn Asn Trp Gly Ile Thr Ser Phe Glu
            885                 890                 895

Met Ala Pro Gln Tyr Arg Ser Ser Gly Asp His Thr Phe Leu Asp Ser
                900                 905                 910

Thr Ile Asp Asn Gly Tyr Ala Phe Thr Asp Arg Tyr Asp Leu Gly Phe
            915                 920                 925

Asn Thr Pro Thr Lys Tyr Gly Thr Asp Gly Asp Leu Arg Ala Thr Ile
            930                 935                 940

Gln Ala Leu His His Ala Asn Met Gln Val Met Ala Asp Val Val Asp
945                 950                 955                 960

Asn Gln Val Tyr Asn Leu Pro Gly Lys Glu Val Val Ser Ala Thr Arg
                965                 970                 975

Ala Gly Val Tyr Gly Asn Asp Asp Ala Thr Gly Phe Gly Thr Gln Leu
            980                 985                 990

Tyr Val Thr Asn Ser Val Gly Gly Gly Gln Tyr Gln Glu Lys Tyr Ala
            995                 1000                1005

Gly Gln Tyr Leu Glu Ala Leu Lys Ala Lys Tyr Pro Asp Leu Phe
        1010                1015                1020

Glu Gly Lys Ala Tyr Asp Tyr Trp Tyr Lys Asn Tyr Ala Asn Asp
        1025                1030                1035

Gly Ser Asn Pro Tyr Tyr Thr Leu Ser His Gly Asp Arg Glu Ser
        1040                1045                1050

Ile Pro Ala Asp Val Ala Ile Lys Gln Trp Ser Ala Lys Tyr Met
        1055                1060                1065

Asn Gly Thr Asn Val Leu Gly Asn Gly Met Gly Tyr Val Leu Lys
        1070                1075                1080

Asp Trp His Asn Gly Gln Tyr Phe Lys Leu Asp Gly Asp Lys Ser
        1085                1090                1095

Thr Leu Pro Lys Gly Gly Arg Ala Asp Pro Ala Phe Leu Tyr Lys
        1100                1105                1110

Val Val Ser Ala Trp Ser His Pro Gln Phe Glu Lys
        1115                1120                1125

FLAVONOIDS O-A-GLUCOSYLATED ON THE B CYCLE, METHOD FOR THE PRODUCTION THEREOF AND USES

CROSS-REFERENCE TO RELATED APPLICATIONS

This application is a U.S. National Stage Application pursuant to 35 U.S.C. § 371 of International Patent Application PCT/EP2015/056307, filed on Mar. 24, 2015, and published as WO 2015/144731 on Oct. 1, 2015, which claims priority to French Patent Application 1456417, filed on Jul. 3, 2014, and French Patent Application No. 1452461, filed on Mar. 24, 2014, all of which are incorporated herein by reference in their entireties for all purposes.

FIELD OF THE INVENTION

The present invention relates to the field of the glucosylation of flavonoids and more particularly of the α-glucosylation of certain flavonoids, in order to obtain derivatives of flavonoids which are O-α-glucosylated, in particular on their aromatic B ring, at the level of non-vicinal hydroxyl functions.

The present invention also relates to the O-α-glucosylated compounds obtained at the end of a glucosylation process of the invention and to the use of these compounds for various purposes, in particular cosmetic or therapeutic purposes.

PRIOR ART

Flavonoids are compounds which have a $C_6$-$C_3$-$C_6$ carbon-based structure, the backbone of which is a cyclic system of 1-benzopyran type, in which the aromatic ring is defined as A ring and the pyran ring is defined as C ring, and which also comprises a phenyl substituent, on the pyran ring, as B ring.

They constitute a group of 8000 compounds widely found in the plant kingdom, where they are responsible for the color of some of the flowers and fruits. They may thus be involved therein in protection against solar radiation, in resistance against pathogenic microorganisms of the plant and against herbivorous animals, and also in the relationships of interaction with the other organisms of the environment, such as symbiotic fungi, bacteria or even insects (Quideau S et al., Angew. Chem. Int. End. 2011 50: 586-621).

Numerous biological properties are moreover attributed thereto, in particular antioxidant, anti-hepatotoxic, anti-allergic, anti-inflammatory, anti-ulcer and anti-tumor properties (Harborne J et al., Phytochemistry 2000 55: 481-504; Quideau S et al., Angew. Chem. Int. End. 2011 50: 586-621).

Flavonoids may be hydroxylated in numerous positions, and these hydroxyl groups are frequently methylated, acetylated, prenylated or sulfated. In plants, they are usually present in the form of C- or O-glycosylated soluble heterocides.

There are at the current time several routes for obtaining glucosylated flavonoids.

Numerous flavonoids exist naturally in the form of heterocides. In vivo, glucosylation is based on the use of glucosyltransferases of Leloir type, capable of transferring the glucosyl residue from a nucleotide-sugar (UDP-glucose) onto the backbone of the flavonoid. These enzymes, which contribute to the synthesis of secondary metabolites in plants, are acknowledged to have a broad spectrum of acceptor substrates.

However, their levels of production by plant cells are very low and the β-glucosylation reaction is the most common, compared with α-glucosylation. Cell glucosylation may have various effects and influence the trafficking and/or the toxicity of the products obtained. Thus, although it is not an absolute rule, it should be noted that, generally, flavonoid glycosylation makes it possible to increase the stability and solubility, and consequently the availability, of these molecules.

Several UDP glycosyltransferases have been isolated and cloned in various microorganisms. The natural or recombinant forms of these enzymes may thus be used in vitro for the production of glucosylated flavonoids.

For example, the UDP glycosyltransferase (UGT) from *Bacillus cereus* has been expressed in *Escherichia coli* (*E. coli*). This enzyme glucosylates apigenin, genistein, campherol, luteolin, naringenin and quercetin. Position 3 is the position preferentially glucosylated, but in the absence of hydroxyl functions on this position, the glucosylation takes place on position 7. The products obtained with the recombinant enzyme are identical to those produced by the wild-type enzyme. (Ko J H et al., FEMS Microbiol. Lett. 2006, 258: 263-268).

Likewise, the UDP glucosyltransferase YjiC from *Bacillus licheniformis* DSM 13 has been used to glucosylate apigenin. Two β-monoglucosylated forms, β-monoglucosylated in position 4' or in position 7, have been obtained. A form β-diglucosylated on positions 4' and 7 has also been structurally characterized (Gurung R. B. et al., Mol. Cells 2013, 36(4): 355-361).

The oleandomycin glycosyltransferase (OleD GT) from *Streptomyces antibioticus* has been expressed in *E. coli* BL 21. The purified enzyme catalyzes the glucosylation of several flavonoids: apigenin, chrysin, daidzein, genistein, campherol, luteolin, naringenin and quercetin, from UDP-glucose. The best conversion (90%) has been obtained with naringenin at 20 µM in 5 h. No indication regarding the glucosylation position is specified in the publication. (Choi S H et al., Biotechnol. Lett. 2012, 34: 499-505).

The UDP glycosyltransferase RhGT1 from *Rosa hybrida* has been tested on a collection of 24 flavonoids. It shows results comparable to those obtained with oleandomycin glycosyltransferase in terms of acceptor recognition (Wang L et al., Carbohydr. Res. 2013, 368: 73-77).

At the current time, six microbial UDP glycosyltransferases are known to have a glucosylation activity on flavonoids (Wang L et al., Carbohydr. Res. 2013, 368: 73-77).

The in vitro glycosylation of flavonoids may be carried out using enzymes of the type glycoside hydrolases, trans-glycosylases of cyclodextrin-glucanotransferase type or glycoside phosphorylases.

More particularly, the enzymatic glycosylation of flavonoids in vitro may be carried out via the use of glucansucrases. Such a synthesis route results in the production of α-glucosylated flavonoids, and is based on the use of glucansucrases belonging to family 13 or 70 of the glycosides hydrolases (GH 13 and GH 70) (Classification CAZy—Henrissat B, Davies G J, Curr. Op. Struct. Biol. 1997, 7: 637-644).

Glucansucrases are transglucosylases which catalyze, from sucrose, the synthesis of homopolymers, consisting of α-D-glucosyl units, called glucan. These glucans generally have a very high molar mass ($10^8$ Da), and have varied structures due to the presence of various types of glycosidic bonds (α-1,2, α-1,3, α-1,4, and/or α-1,6) and also to their location in the polymer. Isomers of sucrose and of glucose are also produced from the sucrose, but in very small amounts compared with the polymer.

More particularly, these enzymes are capable of glucosylating hydroxylated "acceptor" molecules, introduced into the reaction medium as a supplement for sucrose, such as flavonoids. The degree of glucosylation of the acceptor depends on its structure and also on that of the enzyme. Thus, an effective acceptor, or good acceptor, may virtually totally divert the synthesis of polymers to the benefit of its own glucosylation. Conversely, an ineffective acceptor, or poor acceptor, will only be able to very weakly divert the synthesis of polymers and will therefore be only very barely glucosylated, or even not at all.

This is why these enzymes have been studied for many years in order in particular to provide innovative enzymatic tools, effective for the synthesis of original molecules, and meeting industrial needs in particular in terms of synthesis of novel glucoconjugates of interest. Indeed, for obvious reasons, the industry is constantly searching for novel compounds that may in particular be produced in sufficient amounts, and in particular at the lowest possible cost.

As early as 1995, the glucosylation of catechin with a glucosyltransferase from *Streptococcus sobrinus* 6715 (serotype g) was carried out, in a 100 mM phosphate buffer (pH 6) in the presence of 1 g/l of catechin and of 2% of sucrose (Nakahara et al., Appl. Environ Microbiol. 1995, 61: 2768-2770). The monoglucosylated product obtained with a yield of 13.7% is 4'-O-α-D-glucopyranosyl-(+)-catechin.

A similar enzyme, glucosyltransferase-D from *Streptococcus mutans* GS-5, was also tested a few years later on the same substrate (Meulenbeld G et al., Appl. Env. Microbiol. 1999, 65: 4141-4147). Two monoglucosylation products were thus isolated: 4'-O-α-D-glucopyranosyl-(+)-catechin and 7-O-α-D-glucopyranosyl-(+)-catechin, and also a diglucosylated product, 4',7-O-α-D-glucopyranosyl-(+)-catechin.

A study was carried out in 2000 to determine the specificity of glucosyltransferase-D from *Streptococcus mutans* GS-5. Several acceptors were tested (catechol, 3-methoxycatechol, 3-methylcatechol, 4-methylcatechol, phenol, 3-hydroxyphenol, benzyl alcohol, 2-hydroxybenzyl alcohol, 2-methoxybenzyl alcohol, 1-phenyl-1,2-ethanediol, 4-methylphenol, 3-methylphenol, 3,5-dihydroxybenzyl alcohol, 2-methoxy-4-methylphenol, 2-methoxybenzyl alcohol, 3-methoxybenzyl alcohol and catechin) (Meulenbeld G Hartmans S., Biotechnol. Bioeng. 2000, 70: 363-369). Only the acceptors having two adjacent, and therefore vicinal, hydroxyl groups on the aromatic B ring were glucosylated.

A few years later, the enzymatic glucosylation of a flavone (luteolin) and of two flavanols (quercetin and myricetin) was carried out using two glucansucrases: dextransucrase from *Leuconostoc mesenteroides* NRRL B-512F and alternansucrase from *Leuconostoc mesenteroides* NRRL B-23192 (Bertrand A et al., Carbohydr. Res. 2006, 341: 855-863). The reactions were carried out in a mixture of aqueous-organic solvents in order to improve the solubility of the substrates. A degree of conversion of 44% was achieved after 24 hours of reaction catalyzed by the dextransucrase in a mixture containing 70% of acetic acid/sodium acetate aqueous buffer and 30% of bis(2-methoxyethyl) ether. Two products were characterized by NMR: 3'-O-α-D-glucopyranosylluteolin and 4'-O-α-D-glucopyranosylluteolin. In the presence of the alternansucrase, three additional products, namely 4'-O-α-D-triglucopyranosylluteolin and two forms of 4'-O-α-D-diglucopyranosylluteolin, with a degree of luteolin conversion of 8% were obtained.

The two enzymes were also used to glucosylate quercetin and myricetin with respective degrees of conversion of 4% and 49%. No glucosylation was however observed when these two enzymes were used with diosmetin, diosmin and 7-β-D-glucopyranosyldiosmetin.

Quercetin glucosylation in the presence of sucrose and of glucansucrose from the *Leuconostoc mesenteroides* NRRL B-1299 strain has also been described in Korean application KR20060063703.

Epigallocatechin gallate has also been glucosylated in the presence of sucrose and of glucansucrose from *Leuconostoc mesenteroides* B-1299CB (Moon et al., Journal of Molecular Catalysis B: Enzymatic. 2006, 40: 1-7). A mixture of three products was obtained:

a monoglucosylation product: 4"-O-α-D-glucopyranosylepigallocatechin gallate (15.7%); and
two diglucosylation products: 7,4"-O-α-D-glucopyranosylepigallocatechin (22.7%) and 4',4"-di-O-α-D-glucopyranosylepigallocatechin gallate (23.8%).

Quercetin glucosylation was carried out in 2007 in the presence of sucrose and of glucansucrose from *Leuconostoc mesenteroides* B-1299CB (Moon Y H et al., Enzyme Microb. Technol. 2007, 40: 1124-1129). A mixture of two monoglucosylated products is obtained: 4'-O-α-D-glucopyranosylquercetin and 3'-O-α-D-glucopyranosylquercetin.

Amylosucrase from *Deinococcus geothermalis* has been expressed in *E. coli* and studied for the glucosylation of (+)-catechin and 3'-O-α-D-maltosylcatechin (Cho H K et al., Enzyme Microb. Technol. 2011, 49(2): 246-253).

In American patent application US 20110183930A1, Auriol et al. have described the preparation of phenolic derivatives obtained by enzymatic condensation between phenolic compounds selected from pyrocatechols or derivatives thereof, and the glucosyl residue originating from sucrose. The production of these derivatives of phenolic compounds is carried out with a glucosyltransferase (EC 2.4.1.5). The O-α-D-glucosides of phenolic compounds synthesized have a solubility in water that is greater than that of their polyphenol parent.

These compounds are in particular described therein for their use as antioxidant, antiviral, antibacterial, immunostimulant, anti-allergic, antihypertensive, anti-ischemic, antiarrhythmic, anti-thrombic, hypocholesterolemia, antilipoperoxidant, hepatoprotective, anti-inflammatory, anticarcinogen, antimutagenic, antineoplasic and vasodilatator agent.

The glucosylation of astragalin in the presence of sucrose and of glucansucrose from *Leuconostoc mesenteroides* B-512FMCM has also been carried out (Kim G E et al., Enzyme Microb Technol. 2012, 50: 50-56). Nine products have been isolated, namely:

two monoglucosylation products: campherol-3-O-β-D-glucopyranosyl-(1→6)-O-α-D-glucopyranoside and campherol-3-O-β-D-glucopyranosyl-(1→3)-O-α-D-glucopyranoside; and
seven astragalin polyglucosylation products (bonds of α-(1→6) type).

The glucosylation of ampelopsin has also been carried out in the presence of sucrose and of glucansucrose from *Leuconostoc mesenteroides* B-1299CB4. Five glucosylation products have been isolated and the monoglucosylation product has been characterized: it is 4'-O-α-D-glucopyranosylampelopsin (Woo H J et al., Enzyme Microb. Technol. 2012 51: 311-318).

However, to the knowledge of the inventors, and despite the very large number of experiments that have been carried out for many years in the field, the glucosylation of flavonoids that are monohydroxylated or hydroxylated in a non-vicinal manner, on the B ring, has never been carried out.

There is consequently a need, in the prior art, for the availability of flavonoids which are α-glucosylated, and in particular O-α-glucosylated, on non-vicinal hydroxyl groups, in particular on the B ring.

SUMMARY OF THE INVENTION

Thus, the present invention provides a process for producing O-α-glucosylated flavonoid derivatives, comprising at least one step of incubating a glucansucrose with a flavonoid and at least one sucrose, in which:

(A) said flavonoid is of formula (I) below:

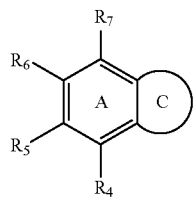

(I)

in which
the C ring represents a ring chosen from the group consisting of the rings of formula (II), (III), (IV) or (V) below:

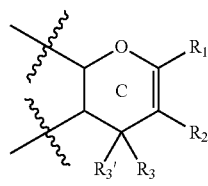

(II)

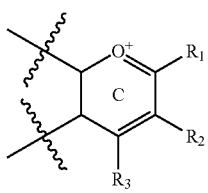

(III)

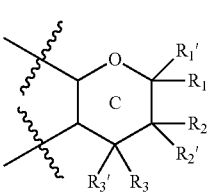

(IV)

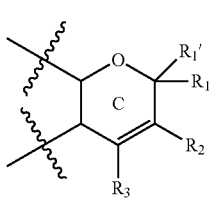

(V)

in which:
one of the R1, R2 or R3 groups represents a B ring of formula (VI) below:

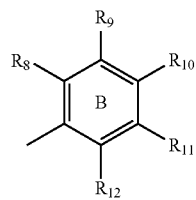

(VI)

in which:
(a) just one of the groups chosen from $R_8$, $R_9$, $R_{10}$, $R_{11}$ and $R_{12}$ represents a hydroxyl group,
the other groups among $R_8$, $R_9$, $R_{10}$, $R_{11}$ and $R_{12}$, which may be identical or different, being chosen from the group comprising a hydrogen atom; a linear or branched, saturated or unsaturated $C_1$-$C_{10}$ hydrocarbon-based group, optionally interrupted with at least one heteroatom chosen from O, N or S; a halogen atom; a $C_5$-$C_9$ aryl; a $C_4$-$C_9$ heterocycle; a $(C_1$-$C_3)$alkoxy group; a $C_2$-$C_3$ acyl; a $C_1$-$C_3$ alcohol; a —COOH; —NH$_2$; —CONH$_2$; —CHO; —SH; —C(O)O $(C_2$-$C_3)$ group; a $C_1$-$C_3$ amine; a $C_1$-$C_3$ imine; a nitrile group; a $C_1$-$C_3$ haloalkyl; a $C_1$-$C_3$ thioalkyl; a —C(W) group; and an —O(W) group; W representing a chain consisting of from 1 to 6 glycoside(s);
or
(b) $R_8$ and just one of the groups chosen from $R_{10}$, $R_{11}$ and $R_{12}$ represent a hydroxyl group,
$R_9$ and the other groups among $R_{10}$, $R_{11}$ and R12, which may be identical or different, being chosen from the group comprising a hydrogen atom; a linear or branched, saturated or unsaturated $C_1$-$C_{10}$ hydrocarbon-based group, optionally interrupted with at least one heteroatom chosen from O, N or S; a halogen atom; a $C_5$-$C_9$ aryl; a $C_4$-$C_9$ heterocycle; a $(C_1$-$C_3)$alkoxy group; a $C_2$-$C_3$ acyl; a $C_1$-$C_3$ alcohol; a —COOH; —NH$_2$; —CONH$_2$; —CHO; —SH; —C(O)O $(C_2$-$C_3)$ group; a $C_1$-$C_3$ amine; a $C_1$-$C_3$ imine; a nitrile group; a $C_1$-$C_3$ haloalkyl; a $C_1$-$C_3$ thioalkyl; a —C(W) group; and an —O(W) group; W representing a chain consisting of from 1 to 6 glycoside(s);
or
(c) $R_9$ and just one of the groups chosen from $R_{11}$ and $R_{12}$ represent a hydroxyl group,
the $R_8$ and $R_{10}$ groups, and the other group among $R_{11}$ and $R_{12}$, which may be identical or different, being chosen from the group comprising a hydrogen atom; a linear or branched, saturated or unsaturated $C_1$-$C_{10}$ hydrocarbon-based group, optionally interrupted with at least one heteroatom chosen from O, N or S; a halogen atom; a $C_5$-$C_9$ aryl; a $C_4$-$C_9$ heterocycle; a $(C_1$-$C_3)$alkoxy group; a $C_2$-$C_3$ acyl; a $C_1$-$C_3$ alcohol; a —COOH; —NH$_2$; —CONH$_2$; —CHO; —SH; —C(O)O($C_2$-$C_3$) group; a $C_1$-$C_3$ amine; a $C_1$-$C_3$ imine; a nitrile group; a $C_1$-$C_3$ haloalkyl; a $C_1$-$C_3$ thioalkyl; a —C(W) group; and an —O(W) group; W representing a chain consisting of from 1 to 6 glycoside(s);
or
(d) $R_{10}$ and $R_{12}$ represent a hydroxyl group,
the $R_8$, $R_9$ and $R_{11}$ groups, which may be identical or different, being chosen from the group comprising a hydrogen atom; a linear or branched, saturated or unsaturated $C_1$-$C_{10}$ hydrocarbon-based group, optionally interrupted with at least one heteroatom chosen from O, N or S; a halogen atom; a $C_5$-$C_9$ aryl; a $C_4$-$C_9$ heterocycle; a $(C_1$-$C_3)$ alkoxy group; a $C_2$-$C_3$ acyl; a $C_1$-$C_3$ alcohol; a —COOH; —NH$_2$; —CONH$_2$; —CHO; —SH; —C(O)O($C_2$-$C_3$) group; a $C_1$-$C_3$ amine; a $C_1$-$C_3$ imine; a nitrile group; a $C_1$-$C_3$ haloalkyl; a $C_1$-$C_3$ thioalkyl; a —C(W) group; and an —O(W) group; W representing a chain consisting of from 1 to 6 glycoside(s);

or (e) $R_8$, $R_{10}$ and $R_{12}$ represent a hydroxyl group, the $R_9$ and $R_{11}$ groups, which may be identical or different, being chosen from the group comprising a hydrogen atom; a linear or branched, saturated or unsaturated $C_1$-$C_{10}$ hydrocarbon-based group, optionally interrupted with at least one heteroatom chosen from O, N or S; a halogen atom; a $C_5$-$C_9$ aryl; a $C_4$-$C_9$ heterocycle; a ($C_1$-$C_3$)alkoxy group; a $C_2$-$C_3$ acyl; a $C_1$-$C_3$ alcohol; a —COOH; —NH$_2$; —CONH$_2$; —CHO; —SH; —C(O)O($C_2$-$C_3$) group; a $C_1$-$C_3$ amine; a $C_1$-$C_3$ imine; a nitrile group; a $C_1$-$C_3$ haloalkyl; a $C_1$-$C_3$ thioalkyl; a —C(W) group; and an —O(W) group; W representing a chain consisting of from 1 to 6 glycoside(s);

the $R_1$, $R_2$ and $R_3$ groups which do not represent a B ring of formula (VI), which may be identical or different, being chosen from the group comprising a hydrogen atom; a linear or branched $C_1$-$C_6$ alkyl; an —OH group; a $C_1$-$C_3$ amine; a —COOH group; —C(O)O($C_2$-$C_3$); a —C(W) group; and an —O(W) group; W representing a chain consisting of from 1 to 6 glycoside(s);

$R_1'$, $R_2'$ and $R_3'$, which may be identical or different, being chosen from the group comprising a hydrogen atom; a linear or branched, saturated or unsaturated $C_1$-$C_{10}$ hydrocarbon-based group, optionally interrupted with at least one heteroatom chosen from O, N or S; a halogen atom; a $C_5$-$C_9$ aryl; a $C_4$-$C_9$ heterocycle; a ($C_1$-$C_3$)alkoxy group; a $C_2$-$C_3$ acyl; a $C_1$-$C_3$ alcohol; a —COOH; —NH$_2$; —CONH$_2$; —CHO; —SH; —C(O)O($C_2$-$C_3$) group; a $C_2$-$C_3$ amine; a $C_1$-$C_3$ amine; a $C_1$-$C_3$ imine; a nitrile group; a $C_1$-$C_3$ haloalkyl; a $C_1$-$C_3$ thioalkyl; a —C(W) group; and an —O(W) group; W representing a chain consisting of from 1 to 6 glycoside(s);

or the $R_1$ and $R_1'$ groups when $R_1$ does not represent a B ring of formula (VI), or $R_2$ and $R_2'$ groups when $R_2$ does not represent a B ring of formula (VI), or $R_3$ and $R_3'$ groups when $R_3$ does not represent a B ring of formula (VI), together form an =O group;

$R_4$, $R_5$, $R_6$ and $R_7$, which may be identical or different, being chosen from the group comprising a hydrogen atom; a linear or branched, saturated or unsaturated $C_1$-$C_{10}$ hydrocarbon-based group, optionally interrupted with at least one heteroatom chosen from O, N or S; a halogen atom; a $C_5$-$C_9$ aryl; a $C_4$-$C_9$ heterocycle; a ($C_1$-$C_3$)alkoxy group; a $C_2$-$C_3$ acyl; a $C_1$-$C_3$ alcohol; an —OH; —COOH; —NH$_2$; —CONH$_2$; —CHO; —SH; —C(O)O($C_2$-$C_3$) group; a $C_1$-$C_3$ amine; a $C_1$-$C_3$ imine; a nitrile group; a $C_1$-$C_3$ haloalkyl; a $C_1$-$C_3$ thioalkyl; a —C(W) group; and an —O(W) group; W representing a chain consisting of from 1 to 6 glycoside(s);

and (B) said glucansucrose being chosen from the group comprising:

a sequence having at least 80% identity with the sequence SEQ ID NO: 1, said sequence having an amino acid $X_1$ representing an amino acid chosen from the group consisting of A, C, E, F, G, H, I, K, M, N, P, Q, S, T, V and Y;

a sequence having at least 80% identity with the sequence SEQ ID NO: 2, said sequence having an amino acid $X_2$ representing an amino acid chosen from the group consisting of A, C, D, F, G, H, K, L, M, N, P, S, V and Y;

a sequence having at least 80% identity with the sequence SEQ ID NO: 3, said sequence having an amino acid $X_3$ representing an amino acid chosen from the group consisting of A, C, G, I, K, M, N and W;

a sequence having at least 80% identity with the sequence SEQ ID NO: 4, said sequence having an amino acid $X_4$ representing an amino acid chosen from the group consisting of C, I, N, P, V and W;

a sequence having at least 80% identity with the sequence SEQ ID NO: 5, said sequence having an amino acid $X_5$ representing an amino acid chosen from the group consisting of A, C, D, G, I, K, L, M, R, V and W;

a sequence having at least 80% identity with the sequence SEQ ID NO: 6, said sequence having an amino acid $X_6$ representing an amino acid chosen from the group consisting of C, G, Q, S and T;

a sequence having at least 80% identity with the sequence SEQ ID NO: 7, said sequence having an amino acid $X_7$ representing an amino acid chosen from the group consisting of A and G;

a sequence having at least 80% identity with SEQ ID NO: 8;

a sequence having at least 80% identity with SEQ ID NO: 9, said sequence having an amino acid $X_8$ representing an amino acid chosen from the group consisting of C, I and L;

a sequence having at least 80% identity with SEQ ID NO: 10;

a sequence having at least 80% identity with SEQ ID NO: 11; and a sequence having at least 80% identity with SEQ ID NO: 12, said sequence having amino acids $X_9$, $X_{10}$, $X_{11}$, $X_{12}$ and $X_{13}$, with:

(i) $X_9$ representing, independently of $X_{10}$, $X_{11}$, $X_{12}$ and $X_{13}$, an amino acid chosen from the group consisting of G, S, V, C, F, N, I, L and W;

$X_{10}$ representing, independently of $X_9$, $X_{11}$, $X_{12}$ and $X_{13}$, an amino acid chosen from the group consisting of L, I, H, Y and F;

with the exception of the case where $X_9$ represents W and $X_{10}$ represents F;

$X_{11}$ representing A;

$X_{12}$ representing F; and $X_{13}$ representing L;

(ii) $X_9$ representing W;

$X_{10}$ representing F;

$X_{11}$ representing, independently of $X_9$, $X_{10}$, $X_{12}$ and $X_{13}$, an amino acid chosen from the group consisting of E and A;

$X_{12}$ representing, independently of $X_9$, $X_{10}$, $X_{11}$ and $X_{13}$, an amino acid chosen from the group consisting of L and F; and $X_{13}$ representing L;

with the exception of the case where $X_{11}$ represents A and $X_{12}$ represents F;

or (iii) $X_9$ representing W;

$X_{10}$ representing F;

$X_{11}$ representing A;

$X_{12}$ representing, independently of $X_9$, $X_{10}$, $X_{11}$ and $X_{13}$, an amino acid chosen from the list consisting of A, R, D, N, C, E, Q, G, H, I, L, K, M, P, S, T, W, Y and V, preferably I; and $X_{13}$ representing, independently of $X_9$, $X_{10}$, $X_{11}$ and $X_{12}$, an amino acid chosen from the list consisting of A, R, D, N, C, E, Q, G, H, I, K, M, F, P, S, T, W, Y and V, preferably I.

The inventors have in fact shown, totally unexpectedly, that certain mutated specific glucansucrases, described hereinafter in the present text, have the capacity to generate novel flavonoids which are O-α-glucosylated on non-vicinal hydroxyl groups, in particular on the B ring. These mutated enzymes in fact have a glucosylation activity that is greater, or even much greater, than their wild-type forms, on these specific flavonoids, usually considered to be poor receptors, since they are very difficult to glucosylate, in particular on the B ring.

More particularly, a glucansucrose used in a process of the invention is chosen from the group comprising:

a sequence having at least 80% identity with SEQ ID NO: 1, said sequence having an amino acid $X_1$ representing an amino acid chosen from the group consisting of H, N or S;

a sequence having at least 80% identity with SEQ ID NO: 2, said sequence having an amino acid $X_2$ representing an amino acid chosen from the group consisting of A, C, F, L, M, S or V;

a sequence having at least 80% identity with SEQ ID NO: 3, said sequence having an amino acid $X_3$ representing an amino acid chosen from the group consisting of A and N;

a sequence having at least 80% identity with SEQ ID NO: 4, said sequence having an amino acid $X_4$ representing an amino acid chosen from the group consisting of C, I, N, P, V or W;

a sequence having at least 80% identity with SEQ ID NO: 5, said sequence having an amino acid $X_5$ representing an amino acid chosen from the group consisting of C, K, R or V;

a sequence having at least 80% identity with SEQ ID NO: 9, said sequence having an amino acid $X_8$ representing an amino acid chosen from the group consisting of C or L; and a sequence having at least 80% identity with SEQ ID NO: 12, said sequence having amino acids $X_9$, $X_{10}$, $X_{11}$, $X_{12}$ and $X_{13}$, with:

(i) $X_9$ representing an amino acid chosen from the group consisting of G, V, C and F;

$X_{10}$ representing F; $X_{11}$ representing A; $X_{12}$ representing F; and $X_{13}$ representing L;

(ii) $X_9$ representing, independently of $X_{10}$, $X_{11}$, $X_{12}$ and $X_{13}$, an amino acid chosen from the group consisting of S, N, L and I;

$X_{10}$ representing, independently of $X_9$, $X_{11}$, $X_{12}$ and $X_{13}$, an amino acid chosen from the group consisting of L, I, H and Y;

$X_{11}$ representing A; $X_{12}$ representing F; and $X_{13}$ representing L;

(iii) $X_9$ representing W; $X_{10}$ representing F; $X_{11}$ representing A or E; $X_{12}$ representing L; and $X_{13}$ representing L; or said sequence having at least 80% identity with sequence SEQ ID NO: 12 is the sequence SEQ ID NO: 13.

A subject of the invention is also an O-α-glycosylated flavonoid derivative obtained by means of the process of the invention, and in particular of formula (I) as defined above, in which the C ring represents the ring of formula (IV) in which the $R_1$ group represents a B ring of formula (VI); and at least the B ring is O-α-glycosylated.

The present invention in fact advantageously makes it possible to obtain flavonoid derivatives according to the invention which are at least O-α-glycosylated, in particular O-α-glucosylated, on the B ring.

The invention also relates to a compound of formula (X) below:

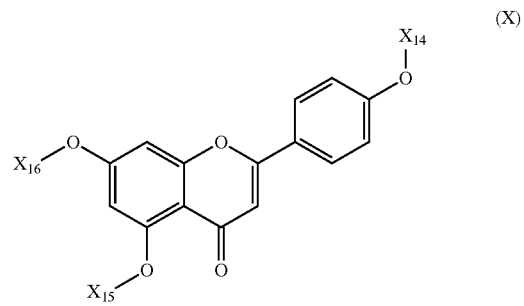

in which $X_{14}$ represents a chain consisting of at least two α-glucoside groups, and $X_{15}$ and $X_{16}$, which may be identical or different, are chosen from the group comprising a hydrogen atom; a linear or branched $C_1$-$C_6$ alkyl; a —C(O)O($C_2$-$C_3$) group; and a chain consisting of from 1 to 600 000 α-glucoside groups.

A chain consisting of from 1 to 600 000 α-glucoside groups according to the invention may more particularly consist of from 1 to 500 000 α-glucoside groups, from 1 to 400 000 α-glucoside groups, from 1 to 300 000 α-glucoside groups, from 1 to 200 000 α-glucoside groups, from 2 to 100 000 α-glucoside groups, from 5 to 50 000 α-glucoside groups, from 10 to 25 000 α-glucoside groups or from 10 to 10 000 α-glucoside groups.

The invention also relates to a compound of formula (XI) below:

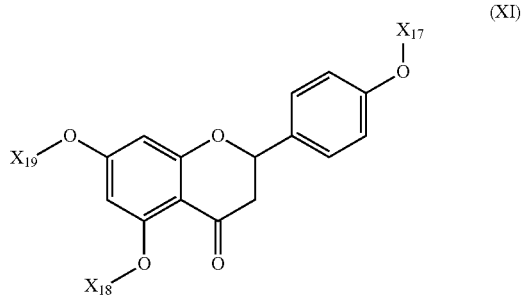

in which $X_{17}$ represents a chain consisting of from 1 to 600 000 α-glucoside groups, and $X_{18}$ and $X_{19}$, which may be identical or different, are chosen from the group comprising a hydrogen atom; a linear or branched $C_1$-$C_6$ alkyl; a —C(O)O($C_2$-$C_3$) group; and a chain consisting of from 1 to 600 000 α-glucoside groups.

The present invention also relates to the cosmetic use, as an antioxidant, of at least one O-α-glycosylated flavonoid derivative in accordance with the invention.

The present invention is also directed toward an O-α-glycosylated flavonoid derivative in accordance with the invention, for pharmaceutical use thereof in the treatment and/or prevention of hepatotoxicity, allergies, inflammation, ulcers, tumors, menopausal disorders, or neurodegenerative diseases.

Another aspect of the invention relates to an O-α-glycosylated flavonoid derivative in accordance with the invention, for pharmaceutical use thereof as a veinotonic. Finally, the present invention relates to the use of an O-α-glycosylated flavonoid derivative in accordance with the invention, as a photovoltaic agent, insect repellent, bleaching agent, pesticide, fungicide and/or bactericide.

In the context of the present invention, and unless otherwise mentioned in the text:

the expression linear or branched, saturated or unsaturated $C_1$-$C_{10}$ hydrocarbon-based group, optionally interrupted with at least one heteroatom chosen from O, N or S, is intended to mean: an alkyl or an alkylene;

the term "alkyl" is intended to mean: a linear or branched, saturated hydrocarbon-based aliphatic group comprising from 1 to 10, preferably from 1 to 6 carbon atoms;

the term "cycloalkyl" is intended to mean: a cyclic alkyl group comprising from 3 to 10 ring members, preferably from 3 to 8 ring members. The cycloalkyl group is optionally substituted with one or more halogen atoms and/or alkyl groups;

the term "heterocycle" is intended to mean: a cyclic alkyl group comprising from 4 to 9 ring members, preferably from 3 to 8 ring members, and consisting of from 1 to 3 rings, comprising between 3 and 6 carbon atoms and one or more heteroatoms, for example 1, 2 or 3 heteroatoms, preferably 1 or 2, chosen from nitrogen, oxygen and sulfur. The heterocycle group is optionally substituted with one or more halogen atoms and/or alkyl groups;

the term "partially cyclic alkyl group" is intended to mean: an alkyl group in which only one part forms a ring;

the term "alkylene" is intended to mean: a linear or branched, divalent alkylene group comprising from 1 to 10, preferably from 1 to 6, carbon atoms;

the term "aryl" is intended to mean: a cyclic aromatic group comprising between 5 and 9 carbon atoms, for example a phenyl group;

the term "heteroaryl" is intended to mean: a cyclic aromatic group comprising between 3 and 10 atoms including one or more heteroatoms, for example between 1 and 4 heteroatoms, such as nitrogen, oxygen or sulfur, this group comprising one or more rings, preferably 1 or 2 rings. The heterocycles may comprise several condensed rings. The heteroaryls are optionally substituted with one or more alkyl groups or an oxygen atom. By way of examples, mention may be made of thienyl, pyridinyl, pyrazolyl, imidazolyl, thiazolyl and triazolyl groups;

the term "halogen" is intended to mean: a chlorine, fluorine, bromine or iodine atom;

the term "$C_1$-$C_3$ alcohol" is intended to mean: an alcohol chosen from methanol, ethanol, propanol and isopropanol;

the term "a ($C_1$-$C_3$)alkoxy" is intended to mean: a group chosen from a methoxyl, an ethoxyl, a propyloxyl and an isopropyloxyl;

the term "$C_2$-$C_3$ acyl" is intended to mean: a group chosen from an acetyl, a propylacetyl and an isopropylacetyl;

the term "$C_1$-$C_3$ amine" is intended to mean: a group chosen from a methylamine, an ethylamine and a propylamine;

the term "$C_1$-$C_3$ imine" is intended to mean: a group chosen from a methylimine, an ethylimine and a propylimine;

In the present application, the term "glycoside" is used to denote a glycoside unit.

Glycoside units are known to those skilled in the art.

By way of examples of monosaccharide glycosides, the following glycosides may be mentioned: glucose, fructose, sorbose, mannose, galactose, talose, allose, gulose, idose, glucosamine, N-acetylglucosamine, mannoamine, galactosamine, glucuronic acid, rhamnose, arabinose, galacturonic acid, fucose, xylose, lyxose and ribose.

By way of examples of disaccharide or oligosaccharide glycosides, the following glycosides may be mentioned:

disaccharides: maltose, gentiobiose, lactose, cellobiose, isomaltose, melibiose, laminaribiose, chitobiose, xylobiose, mannobiose, sophorose, nigerose, kojibiose, rutinose, robinose, oligosacchacarides: panose, galactotriose, β-glucotriose, β-glucotetraose, galactotetraose, maltodextrin, in particular maltotriose, isomaltotriose, maltotetraose, maltopentaose, maltoheptaose.

By way of examples of glycosides, the following may also be mentioned:

starch derivatives, in particular maltose, maltodextrins,
cellulose derivatives,
pectins and derivatives thereof,
chitin, chitosan and derivatives thereof,
glucoaminoglucans and derivatives thereof,
xyloglucan derivatives,
galactomannans and derivatives thereof.

For the purposes of the invention, the expression "a chain consisting of from 1 to 6 glycoside(s)" is intended to mean a sequence of from 1 to 6 glycosides mentioned above.

Likewise, for the purposes of the present invention, the expression "a chain consisting of from 1 to 600 000 α-glucoside groups" is intended to mean a sequence of 1 to 600 000 glucosyl units bonded to one another by α-bonds.

Structure of the m/z ion at 353.0667, signature of a glucosylation of each of the two positions 5 and 7 of the A ring of apigenin.

Figure 19:
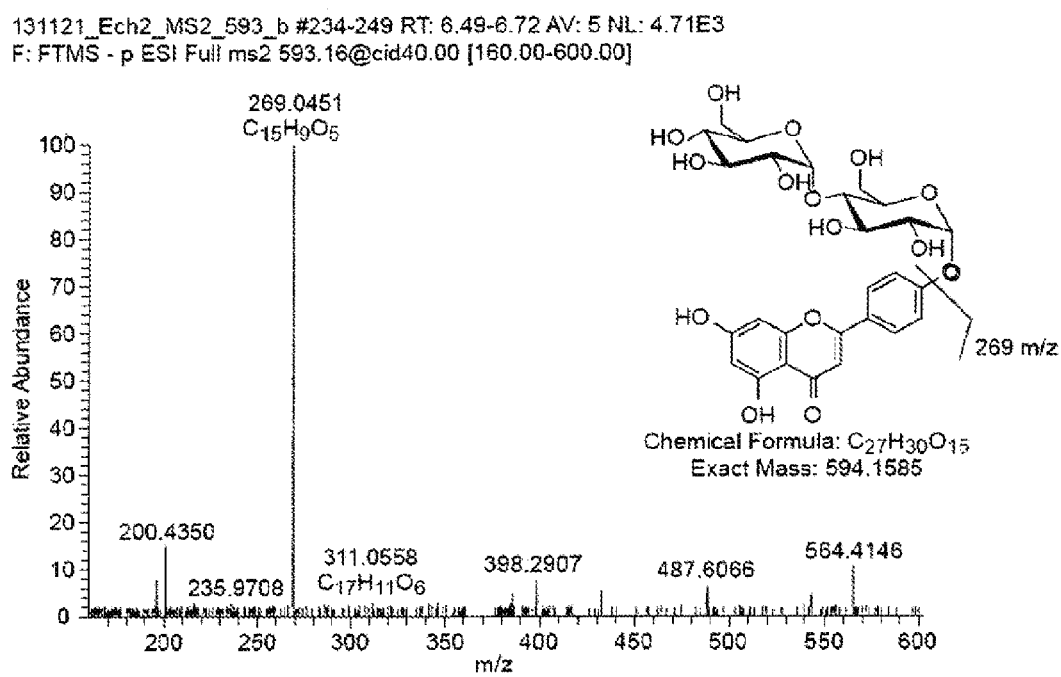

FIG. 19 illustrates the negative electrospray mode high-resolution MS/MS spectrum for one of the two diglucosylated forms of apigenin (at m/z 593.16) obtained with the mutant enzyme ASNp A289W. Along the X-axis: m/z ratio; Along the Y-axis: relative abundance.

Fragmentation of the diglucosylated form on position 4' of the B ring of apigenin resulting in the m/z ion at 269.0451.

Figure 20:
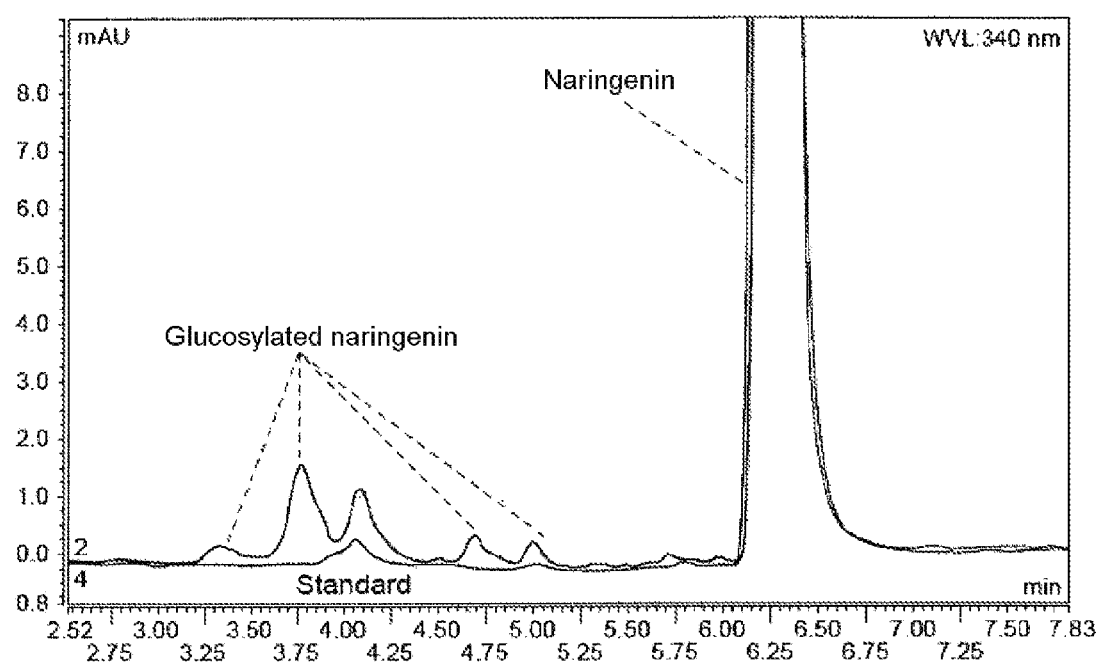

FIG. 20 illustrates the UV chromatography profile obtained after naringenin glucosylation, for the wild-type ASNp enzyme (ASNp WT), in comparison with the naringenin standard. Along the X-axis: Retention time in minutes; Along the Y-axis: Absorbance in mAU (milliabsorbance units).

Figure 21:
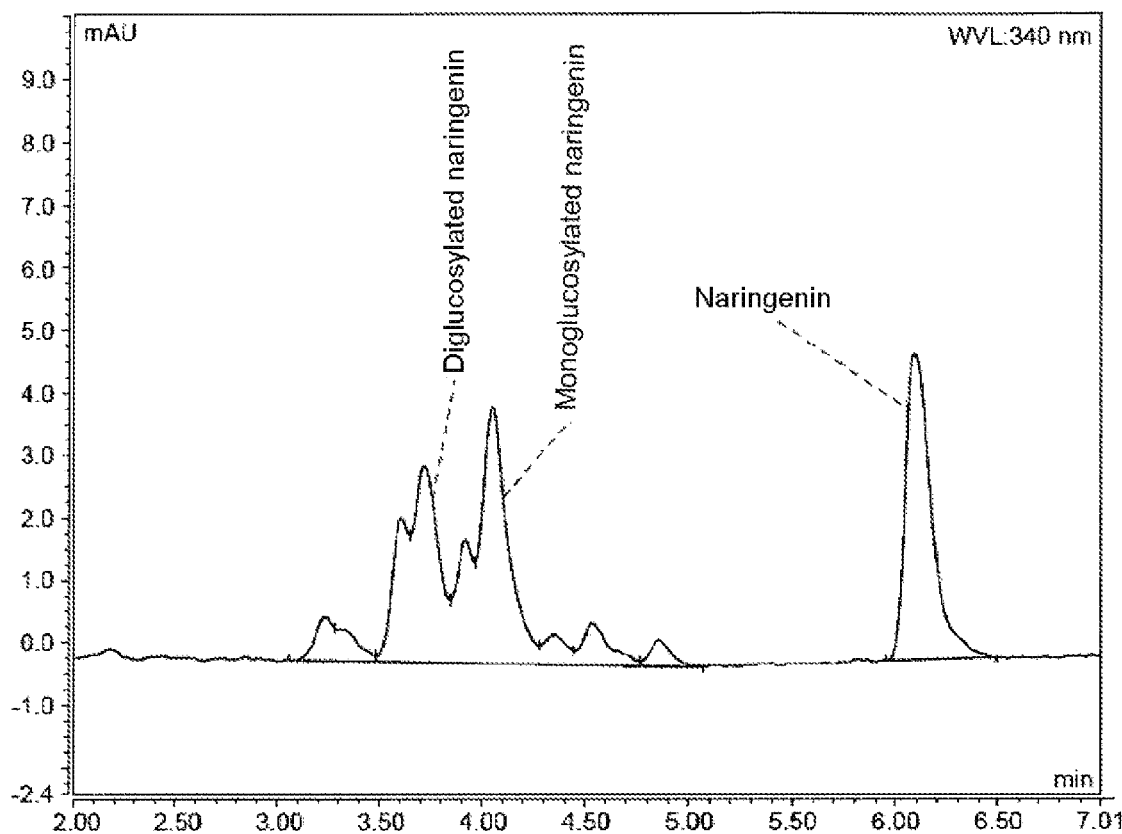

FIG. 21 illustrates the UV chromatography profile obtained after naringenin glucosylation, for the mutant enzyme ASNp I228A. Along the X-axis: Retention time in minutes; Along the Y-axis: Absorbance in mAU (milliabsorbance units).

Figure 22:
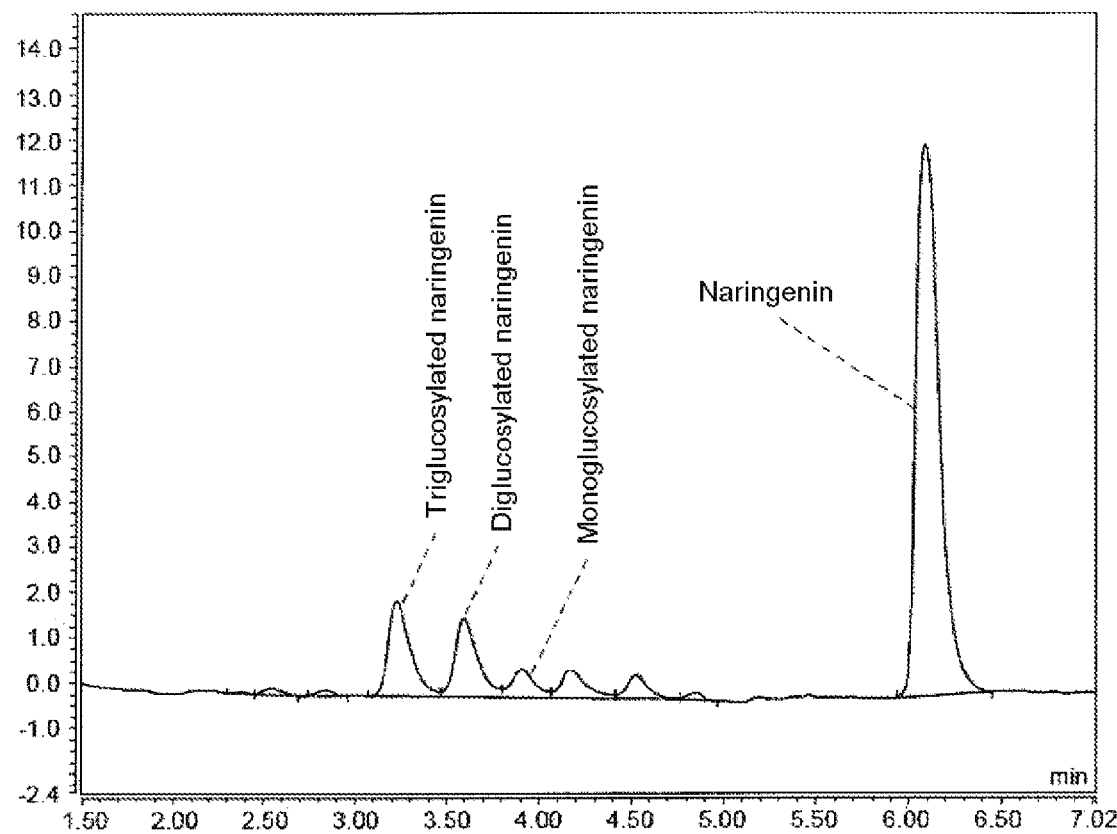

FIG. 22 illustrates the UV chromatography profile obtained after naringenin glucosylation, for the mutant enzyme ASNp A289C. Along the X-axis: Retention time in minutes; Along the Y-axis: Absorbance in mAU (milliabsorbance units).

Figure 23:
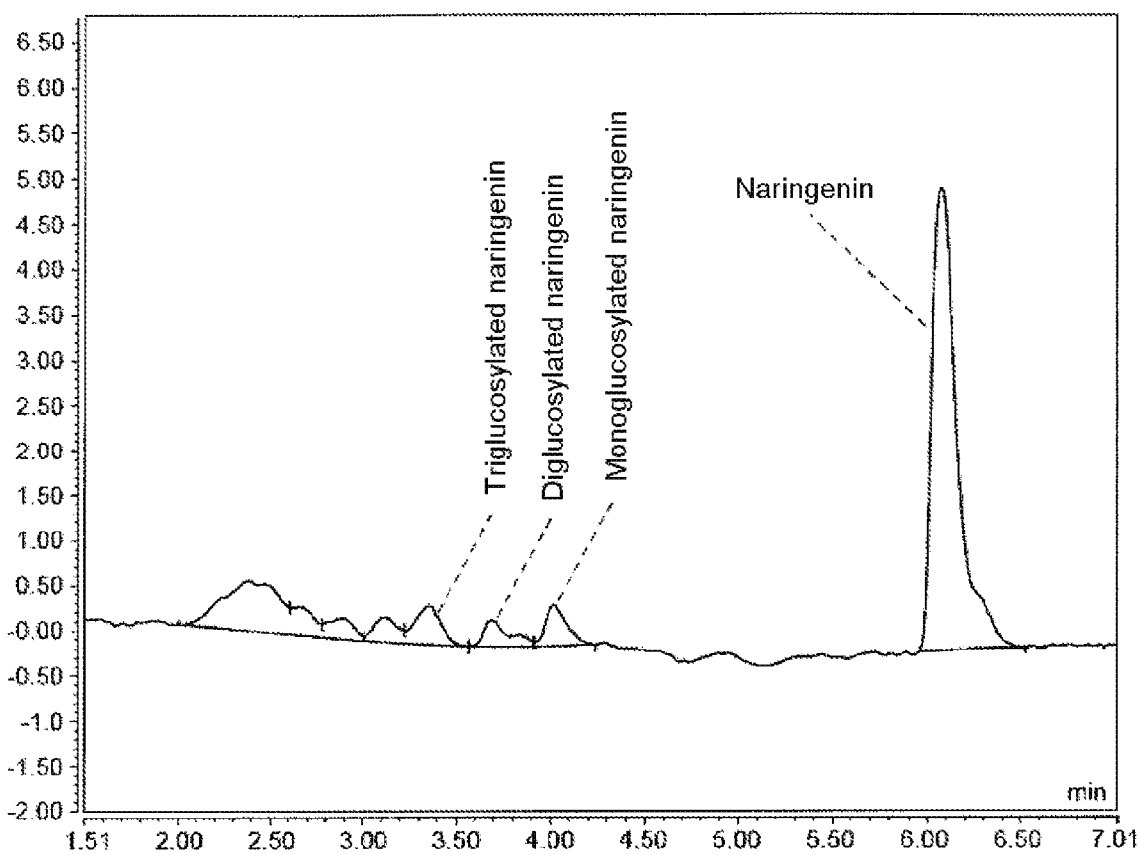

FIG. 23 illustrates the UV chromatography profile obtained after naringenin glucosylation, for the truncated wild-type enzyme ASR-C-APY-del. Along the X-axis: Retention time in minutes; Along the Y-axis: Absorbance in mAU (milliabsorbance units).

Figure 24:
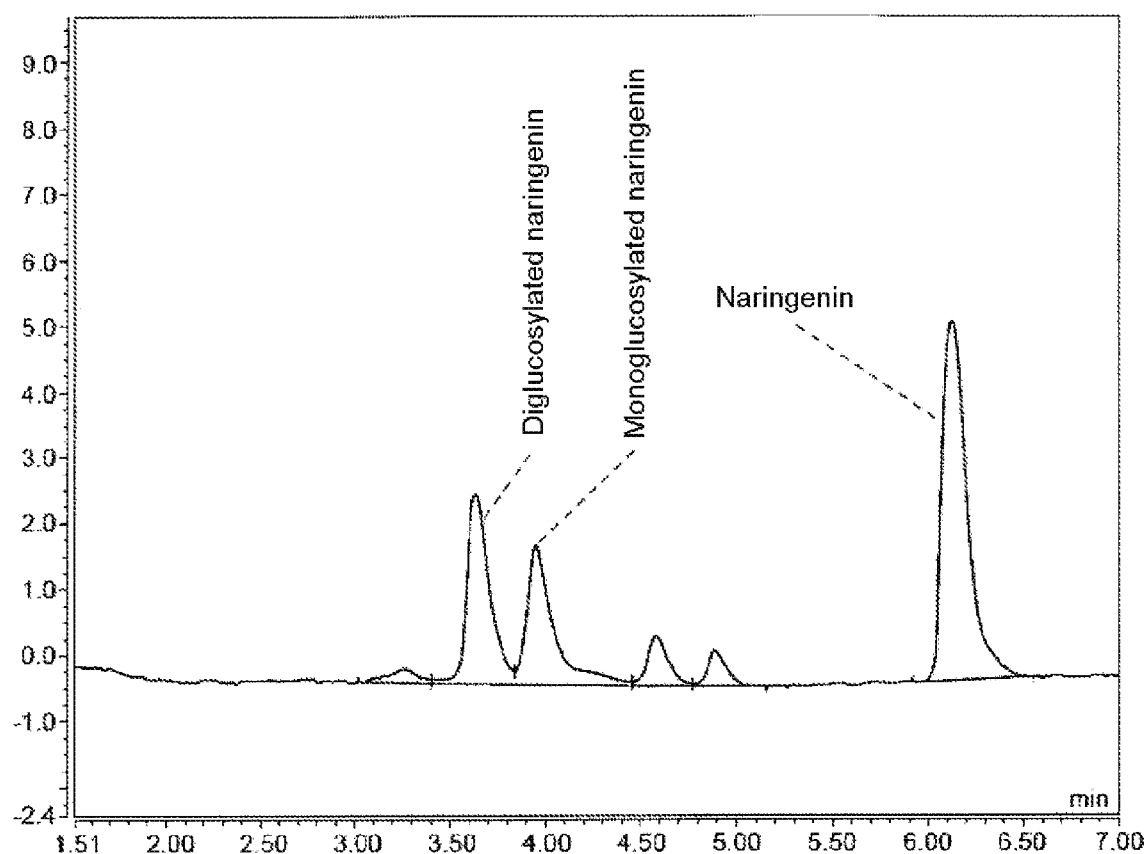

FIG. 24 illustrates the UV chromatography profile obtained after naringenin glucosylation, for the mutant enzyme ASNp A289P/F290C. Along the X-axis: Retention time in minutes; Along the Y-axis: Absorbance in mAU (milliabsorbance units).

Figure 25:
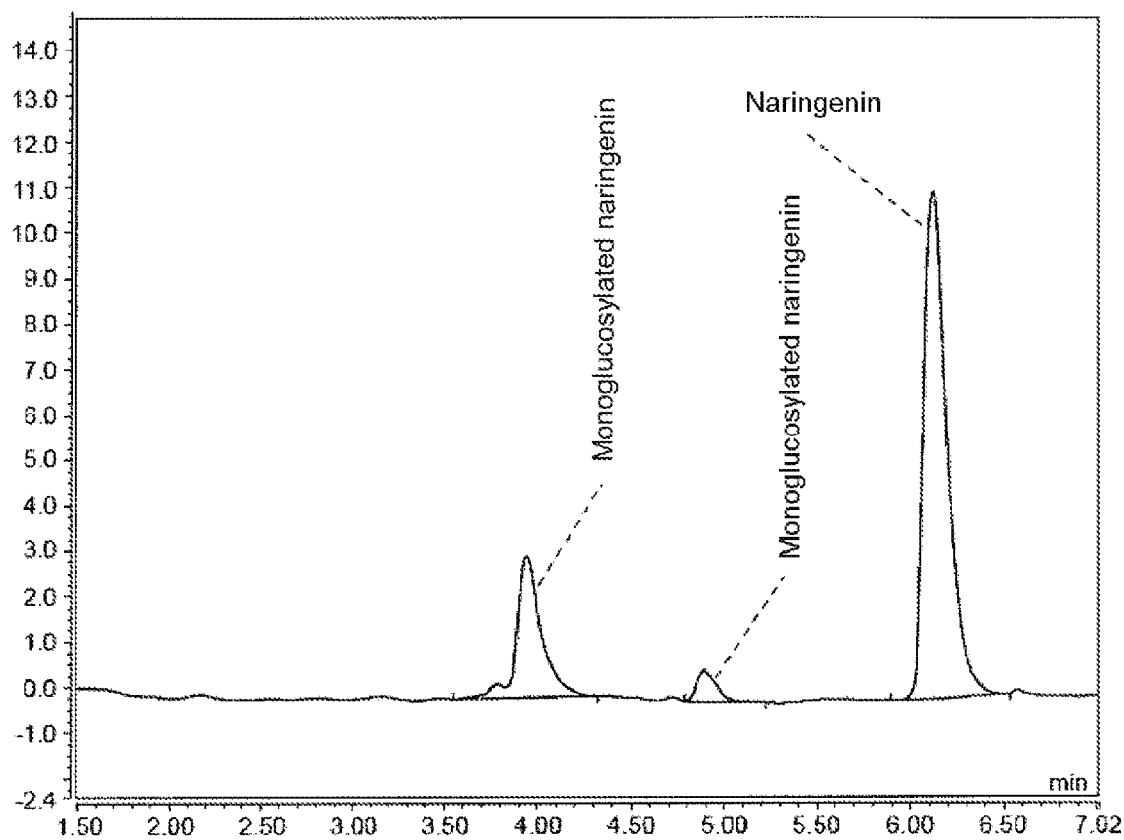

FIG. 25 illustrates the UV chromatography profile obtained after naringenin glucosylation, for the wild-type enzyme α-1,2 BrS. Along the X-axis: Retention time in minutes; Along the Y-axis: Absorbance in mAU (milliabsorbance units).

Figure 26:
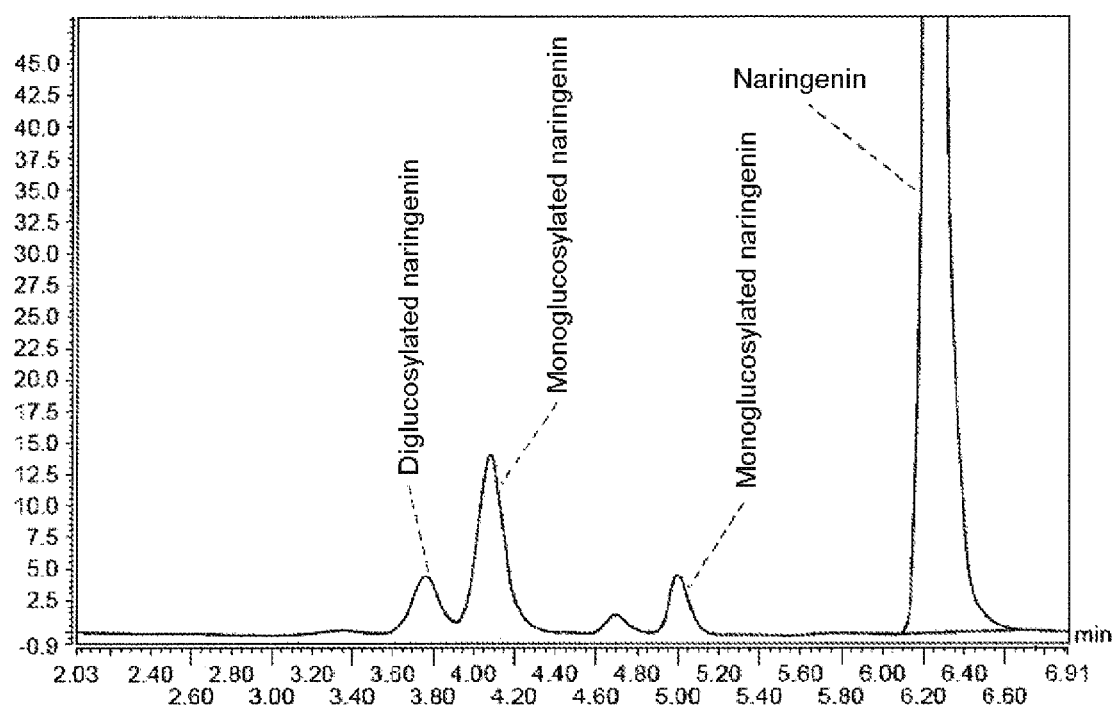

FIG. 26 illustrates the UV chromatography profile obtained after naringenin glucosylation, for the mutant enzyme ASNp F290V. Along the X-axis: Retention time in minutes; Along the Y-axis: Absorbance in mAU (milliabsorbance units).

Figure 27:
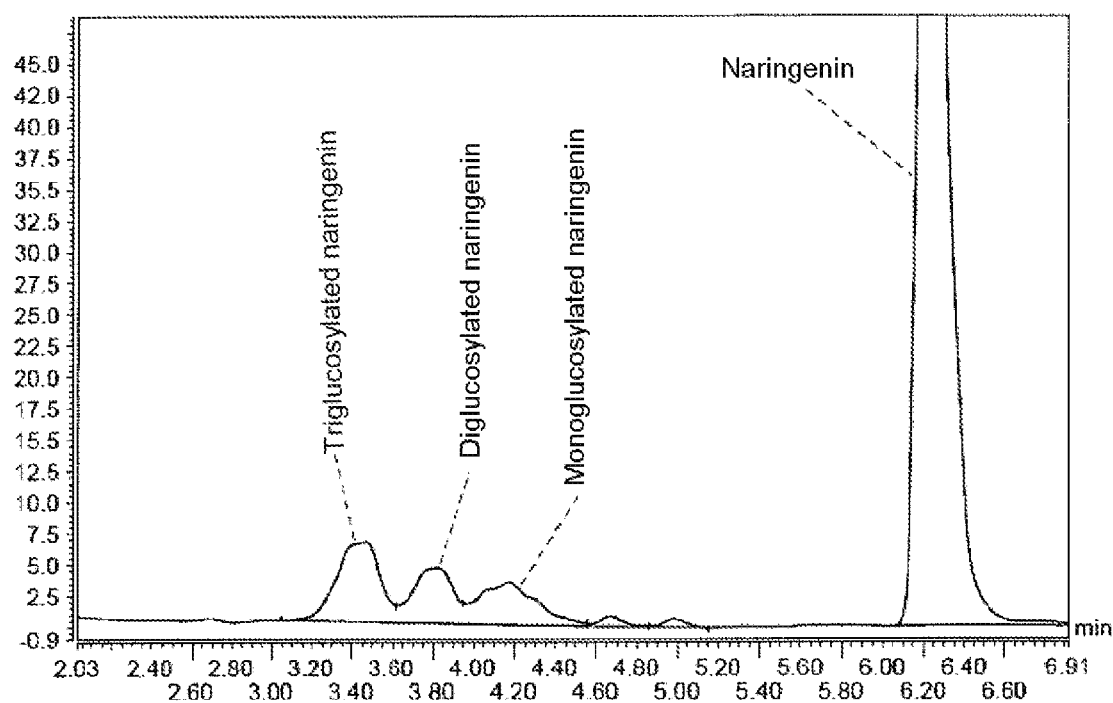

FIG. 27 illustrates the UV chromatography profile obtained after naringenin glucosylation, for the mutant enzyme ASNp R226N. Along the X-axis: Retention time in minutes; Along the Y-axis: Absorbance in mAU (milliabsorbance units).

Figure 28:
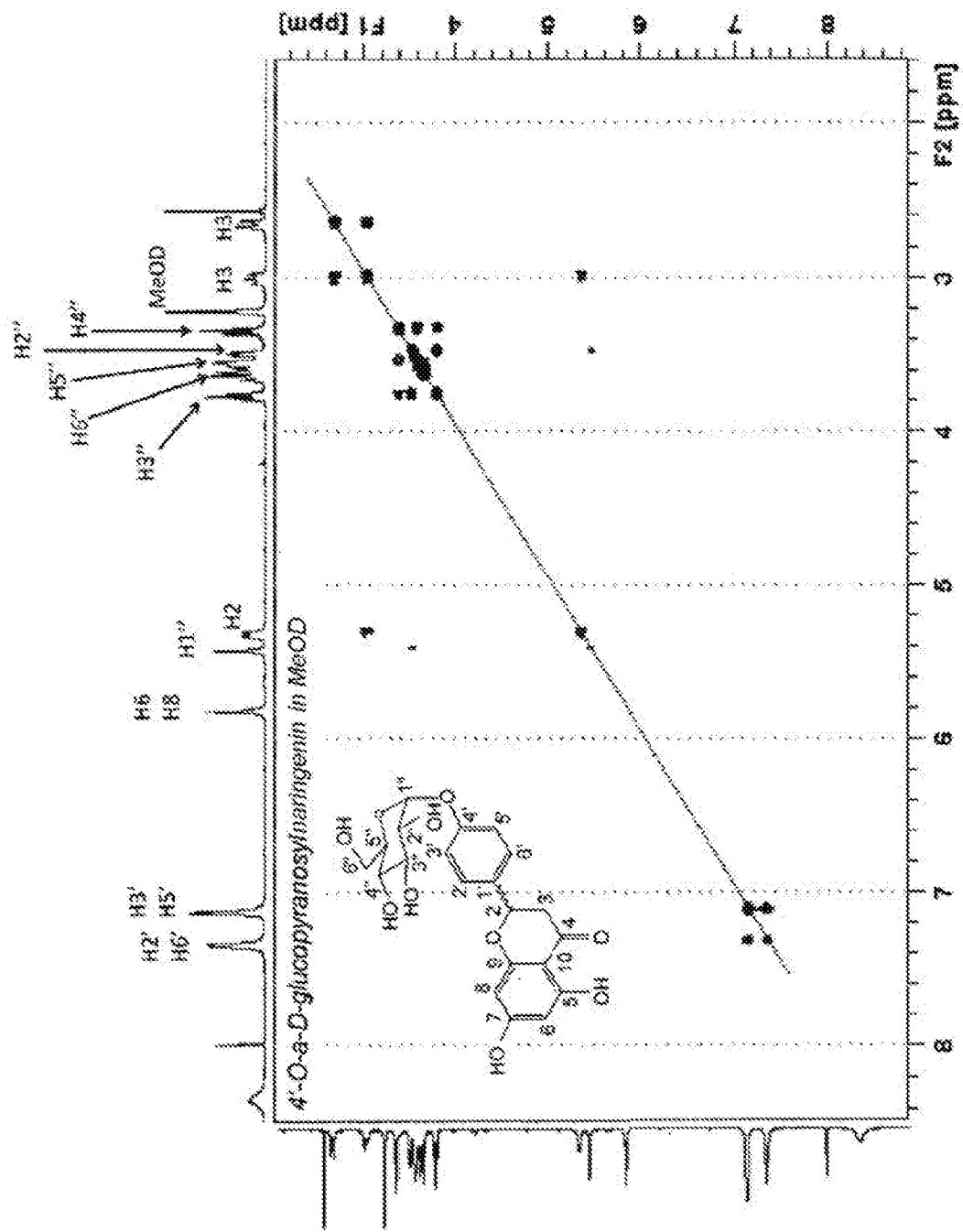

FIG. 28 illustrates the COSY $^1$H 2D NMR spectrum of 4'-O-α-D-glucopyranosylnaringenin. Along the X-axis and Y-axis: chemical shift, in parts per million (ppm).

Figure 29:
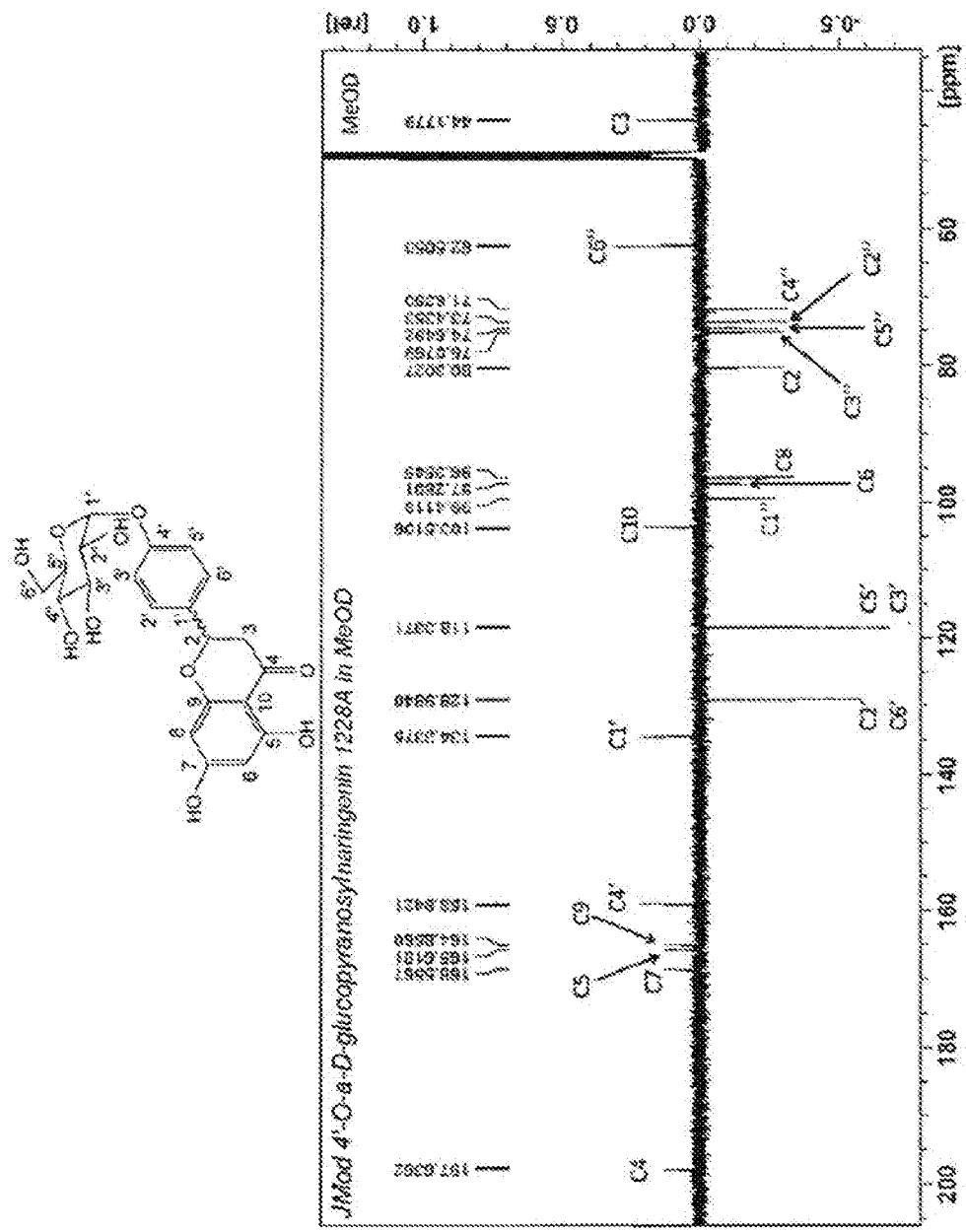

FIG. 29 illustrates the Jmod $^{13}$C 1D NMR spectrum of 4'-O-α-D-glucopyranosylnaringenin. Along the X-axis and Y-axis: chemical shift, in parts per million (ppm).

Figure 30:
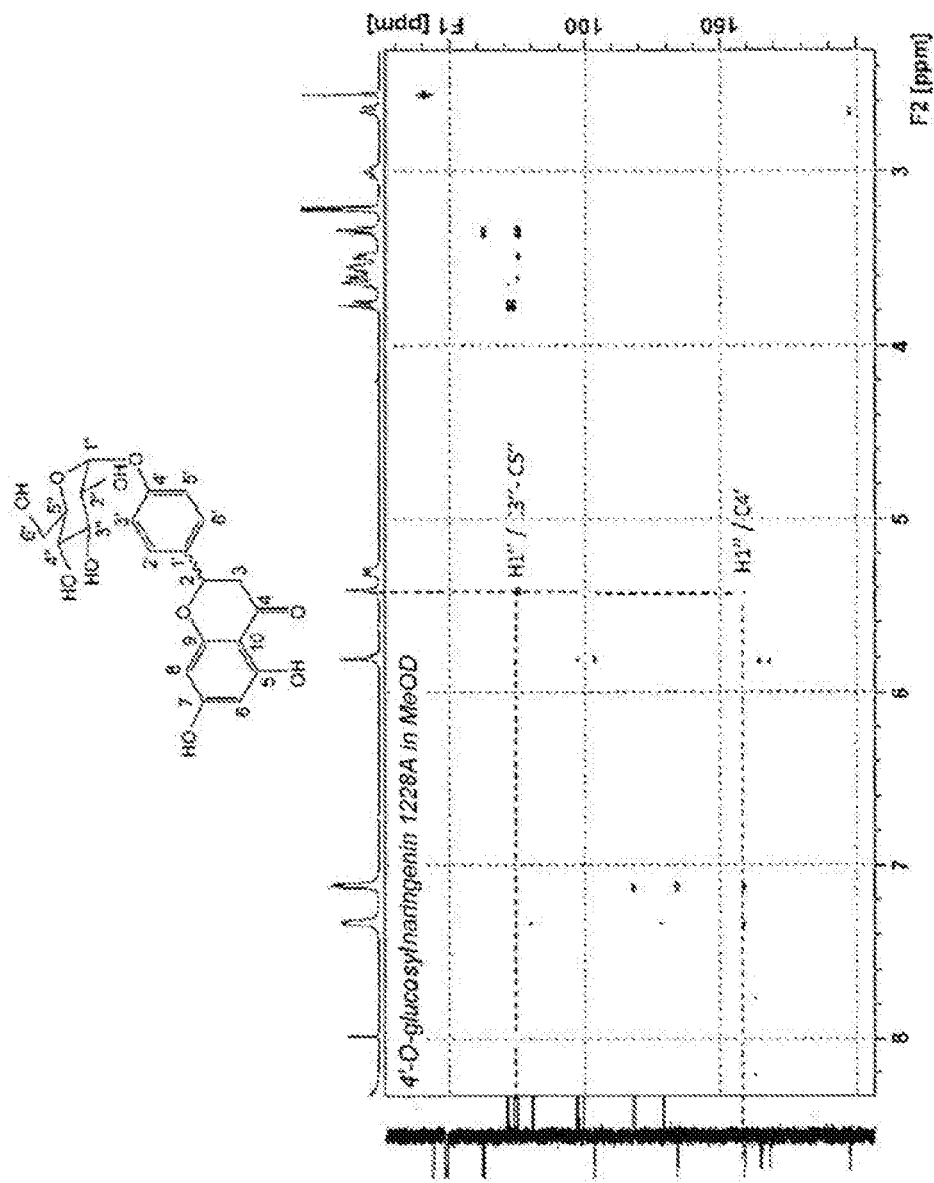

FIG. 30 illustrates the HMBC 2D NMR spectrum of 4'-O-α-D-glucopyranosylnaringenin. Along the X-axis and Y-axis: chemical shift, in parts per million (ppm).

Figure 31:
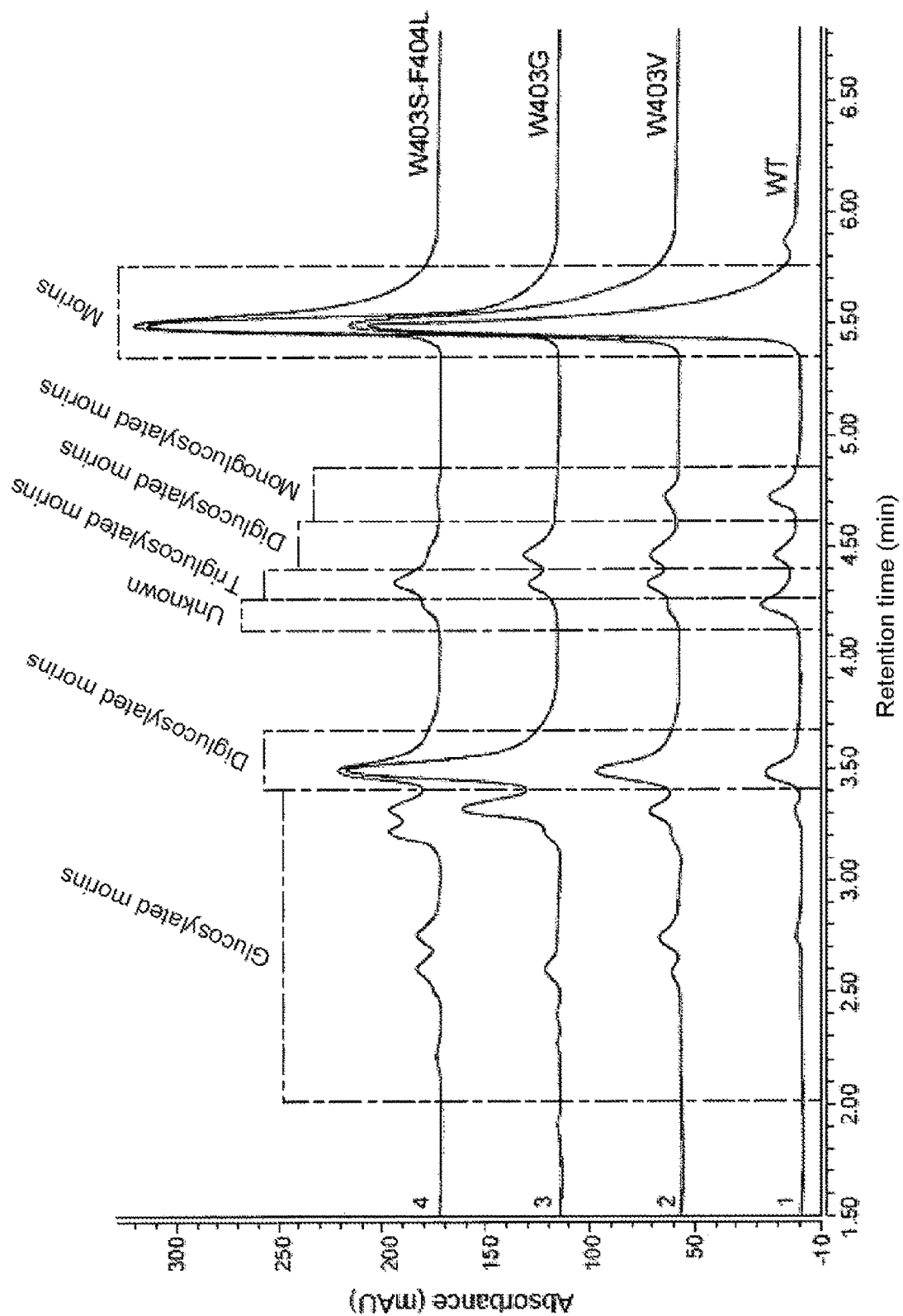

FIG. 31 illustrates the superimposition of the chromatographic profiles obtained by LC-UV-MS for the products of morin glucosylation by the $\Delta N_{123}$-GBD-CD2 WT enzyme and three of the most efficient mutants for glucosylating this flavonoid. Along the X-axis: Retention time in minutes; Along the Y-axis: Absorbance in mAU (milliabsorbance units).

Figure 32:
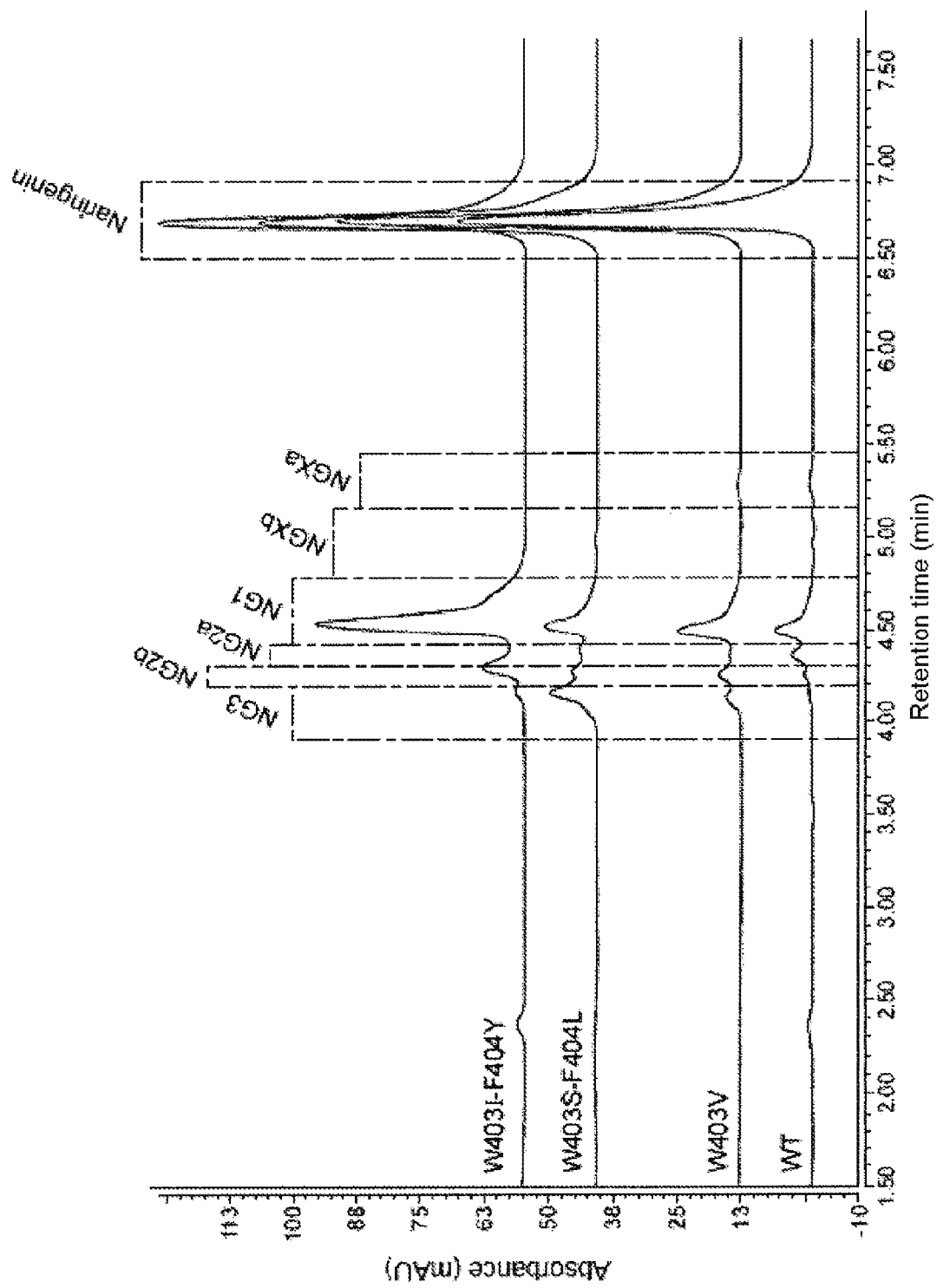

FIG. 32 illustrates the superimposition of the chromatographic profiles obtained by LC-UV-MS for the products of naringenin glucosylation by the $\Delta N_{123}$-GBD-CD2 enzyme and three of its efficient mutants for glucosylating this flavonoid. Along the X-axis: Retention time in minutes; Along the Y-axis: Absorbance in mAU (milliabsorbance units).

DETAILED DESCRIPTION OF THE INVENTION

In order to make available novel O-α-glucosylated flavonoids, the applicant has developed a novel process for the synthesis of novel structures of α-glucoflavonoids specifically glycosylated on non-vicinal hydroxyls, in particular of the B ring. This process uses mutated specific glucansucrases, identified by the applicant, capable of performing such a glucosylation.

These specific enzymes require for this only the presence of sucrose, a renewable and inexpensive agricultural resource. In this respect, a process according to the invention is advantageously inexpensive.

Glucansucrases of the Invention

The present invention relates firstly to a process for producing O-α-glucosylated flavonoid derivatives, comprising at least one step of incubating an enzyme of the invention with a flavonoid of formula (I) and at least one sucrose.

As previously indicated, the enzymes of the invention are advantageously capable of glucosylating flavonoids at the level of non-vicinal hydroxyl function(s), in particular present on the B ring.

These enzymes consist more particularly of glucansucrases belonging to families 13 and 70 of the glycoside hydrolases (GH13 and GH70).

The glucansucrases belonging to family 13 are naturally produced by bacteria of the *Deinococcus*, *Neisseria* or *Alteromonas* genera.

The glucansucrases belonging to family 70 are for their part naturally produced by lactic acid bacteria of the *Leuconostoc*, *Lactobacillus*, *Streptococcus* or *Weissela* sp. genera.

As previously indicated, various wild-type glucansucrases of family 13 or 70 of the glycoside hydrolases have already been used for the production of glucosylated flavonoids, but none of them has to date been described as being capable of glucosylating the flavonoids more particularly targeted in the present invention, namely those which are monohydroxylated on the B ring or which have non-vicinal hydroxyl functions on the B ring.

As it happens, as shown in the examples, the inventors have determined variants of these enzymes, mutated at the level of their flavonoid-binding site, and capable of efficiently glucosylating such compounds.

All of the wild-type or mutated enzymes described in the present application that were known to those skilled in the art had to date never been used to glucosylate flavonoids according to the invention.

The nucleotide sequence of the wild-type form of the ASNp (amylosucrase *Neisseria polysaccharea*) enzyme (family GH13) has the GenBank reference AJ011781.1, while its polypeptide sequence has the Uniprot reference Q9ZEU2.

The nucleotide sequence of the wild-type form of the DSR-S enzyme (derived from the *Leuconostoc mesenteroides* B-512F strain) has the GenBank reference I09598.

The nucleotide sequence of the wild-type form of the DSR-E enzyme (derived from the *Leuconostoc mesenteroides* NRRL B-1299 strain) has the GenBank reference AJ430204.1 and the Uniprot reference Q8G9Q2.

The ΔN123-GBD-CD2 enzyme (sequence SEQ ID NO: 12) is a truncated form of the abovementioned DSR-E enzyme, as described in Brison et al., J. Biol. Chem., 2012, 287, 7915-24.

Literature references describing these mutated enzymes are indicated in tables 1 and 4. In addition, the method for obtaining the mutated enzymes is described in European patent application EP 2 100 966 A1.

The peptide sequences of the various mutated or non-mutated enzymes according to the invention are indicated in the present application. Thus, an enzyme according to the invention may be synthesized by conventional synthesis chemistry methods, that is to say homogeneous chemical syntheses in solution or in solid phase. By way of illustration, those skilled in the art may use the techniques for polypeptide synthesis in solution described by Houben Weil (1974, In methode der Organischen Chemie, E. Wunsh ed., volume 15-I and 15II, Thieme, Stuttgart.). An enzyme according to the invention may also be chemically synthesized in the liquid or solid phase by means of successive couplings of the various amino acid residues (from the N-terminal end to the C-terminal end in liquid phase, or from the C-terminal end to the N-terminal end in solid phase). Those skilled in the art may in particular use the solid-phase peptide synthesis technique described by Merrifield (Merrifield R B, (1965a), Nature, vol. 207 (996): 522-523; Merrifield Rb, (1965b), Science, vol. 150 (693): 178-185).

According to another aspect, an enzyme according to the invention may be synthesized by genetic recombination, for example according to a production process comprising the following steps:

(a) preparing an expression vector into which has been inserted a nucleic acid encoding the peptide sequence of an enzyme of the invention, said vector also comprising the regulatory sequences required for the expression of said nucleic acid in a chosen host cell;

(b) transfecting a host cell with the recombinant vector obtained in step (a);

(c) culturing the host cell transfected in step b) in an appropriate culture medium;

(d) recovering the culture supernatent of the transfected cells or the cell lysate of said cells, for example by sonication or by osmotic shock; and (e) separating or purifying, from said culture medium, or from the cell lysate pellet, the enzyme of the invention thus obtained.

In order to purify an enzyme according to the invention that has been produced by host cells transfected or infected with a recombinant vector encoding said enzyme, those skilled in the art may advantageously use purification techniques described by Molinier-Frenkel (2002, J. Viral. 76, 127-135), by Karayan et al. (1994, Virology 782-795) or by Novelli et al. (1991, Virology 185, 365-376).

Thus, glucansucrases that are usable in a process of the invention are chosen from a group comprising:

- a sequence having at least 80% identity with the sequence SEQ ID NO: 1, said sequence having an amino acid $X_1$ representing an amino acid chosen from the group consisting of A, C, E, F, G, H, I, K, M, N, P, Q, S, T, V and Y;
- a sequence having at least 80% identity with the sequence SEQ ID NO: 2, said sequence having an amino acid $X_2$ representing an amino acid chosen from the group consisting of A, C, D, F, G, H, K, L, M, N, P, S, V and Y;
- a sequence having at least 80% identity with the sequence SEQ ID NO: 3, said sequence having an amino acid $X_3$ representing an amino acid chosen from the group consisting of A, C, G, I, K, M, N and W;
- a sequence having at least 80% identity with the sequence SEQ ID NO: 4, said sequence having an amino acid $X_4$ representing an amino acid chosen from the group consisting of C, I, N, P, V and W;
- a sequence having at least 80% identity with the sequence SEQ ID NO: 5, said sequence having an amino acid Xs representing an amino acid chosen from the group consisting of A, C, D, G, I, K, L, M, R, V and W;
- a sequence having at least 80% identity with the sequence SEQ ID NO: 6, said sequence having an amino acid $X_6$ representing an amino acid chosen from the group consisting of C, G, Q, S and T;
- a sequence having at least 80% identity with the sequence SEQ ID NO: 7, said sequence having an amino acid $X_7$ representing an amino acid chosen from the group consisting of A and G;
- a sequence having at least 80% identity with the sequence SEQ ID NO: 8;
- a sequence having at least 80% identity with the sequence SEQ ID NO: 9;
- said sequence having an amino acid Xs representing an amino acid chosen from the group consisting of C, I and L;
- a sequence having at least 80% identity with the sequence SEQ ID NO: 10;
- a sequence having at least 80% identity with the sequence SEQ ID NO: 11; and
- a sequence having at least 80% identity with the sequence SEQ ID NO: 12, said sequence having amino acids $X_9$, $X_{10}$, $X_{11}$, $X_{12}$ and $X_{13}$, with:
  (i) $X_9$ representing, independently of $X_{10}$, $X_{11}$, $X_{12}$ and $X_{13}$, an amino acid chosen from the group consisting of G, S, V, C, F, N, I, L and W;
  $X_{10}$ representing, independently of $X_9$, $X_{11}$, $X_{12}$ and $X_{13}$, an amino acid chosen from the group consisting of L, I, H, Y and F;
  with the exception of the case where $X_9$ represents W and $X_{10}$ represents F;
  $X_{11}$ representing A;
  $X_{12}$ representing F; and
  $X_{13}$ representing L;
  (ii) $X_9$ representing W; $X_{10}$ representing F;
  $X_{11}$ representing, independently of $X_9$, $X_{10}$, $X_{12}$ and $X_{13}$, an amino acid chosen from the group consisting of E and A;
  $X_{12}$ representing, independently of $X_9$, $X_{10}$, $X_{11}$ and $X_{13}$, an amino acid chosen from the group consisting of L and F;

with the exception of the case where $X_{11}$ represents A and $X_{12}$ represents F;
$X_{13}$ representing L;
or
(iii) $X_9$ representing W;
$X_{10}$ representing F;
$X_{11}$ representing A;
$X_{12}$ representing, independently of $X_9$, $X_{10}$, $X_{11}$ and $X_{13}$, an amino acid chosen from the group consisting of A, R, D, N, C, E, Q, G, H, I, L, K, M, P, S, T, W, Y and V; and
$X_{13}$ representing, independently of $X_9$, $X_{10}$, $X_{11}$ and $X_{12}$, an amino acid chosen from the group consisting of A, R, D, N, C, E, Q, G, H, I, K, M, F, P, S, T, W, Y and V.

According to one embodiment of the invention, a sequence having at least 80% identity with SEQ ID NO: 12 indicated above is preferably such that:

(i) $X_9$ represents, independently of $X_{10}$, $X_{11}$, $X_{12}$ and $X_{13}$, an amino acid chosen from the group consisting of G, S, V, C, F, N, I, L and W;
$X_{10}$ represents, independently of $X_9$, $X_{11}$, $X_{12}$ and $X_{13}$, an amino acid chosen from the group consisting of L, I, H, Y and F;
with the exception of the case where $X_9$ represents W and $X_{10}$ represents F;
$X_{11}$ represents A;
$X_{12}$ represents F; and
$X_{13}$ represents L;
or
(ii) $X_9$ represents W;
$X_{10}$ represents F;
$X_{11}$ represents, independently of $X_9$, $X_{10}$, $X_{12}$ and $X_{13}$, an amino acid chosen from the group consisting of E and A;
$X_{12}$ represents, independently of $X_9$, $X_{10}$, $X_{11}$ and $X_{13}$, an amino acid chosen from the group consisting of L and F;
with the exception of the case where $X_{11}$ represents A and $X_{12}$ represents F; $X_{13}$ represents L;
or
is the sequence SEQ ID NO: 13.

In this sequence SEQ ID NO: 13, $X_9$ represents W, $X_{10}$ represents F, $X_{11}$ represents A, $X_{12}$ represents I, $X_{13}$ represents I, and the aspartic acid (D) in position 432 is substituted with a glutamic acid (E).

It should be understood from this formulation that the amino acids defined as being respectively $X_1$, $X_2$, $X_3$, $X_4$, $X_5$, $X_6$, $X_7$, $X_8$, $X_9$, $X_{10}$, $X_{11}$, $X_{12}$ and $X_{13}$ are present and as defined above in the glucansucrases of the invention having at least 80% identity with, respectively, a sequence SEQ ID NO: 1 to 7, 9 and 12, as defined above.

As shown in the examples, all the enzymes having one of these peptide sequences exhibit a capacity, statistically greater than that of the wild-type enzyme, for glucosylating the flavonoids of the invention, having non-vicinal hydroxyl functions, in particular on the B ring.

The present invention also encompasses the sequences of which the amino acid sequence has at least 80%, 81%, 82%, 83%, 84%, 85%, 86%, 87%, 88%, 89%, 90%, 91%, 92%, 93%, 94%, 95%, 96%, 97%, 98%, 99% or 100% amino acid identity with one of the sequences SEQ ID NO: 1 to 12 as defined previously and a biological activity of the same nature.

The expression "biological activity of the same nature" with regard to the peptide sequences 1 to 12 is intended to mean the same capacity for glucosylating flavonoids which are monohydroxylated or hydroxylated in a non-vicinal manner on the B ring.

For the purposes of the present invention, the "percentage identity" between two nucleic acid or amino acid sequences is determined by comparing the two sequences optimally aligned, through a comparison window.

The part of the nucleotide sequence in the comparison window may thus comprise additions or deletions (for example "gaps") compared with the reference sequence (which does not comprises these additions or these deletions) so as to obtain optimal alignment between the two sequences.

The percentage identity is calculated by determining the number of positions at which an identical nucleic base (or an identical amino acid) is observed for the two sequences compared, then by dividing the number of positions at which there is identity between the two nucleic bases (or between the two amino acids) by the total number of positions in the comparison window, then by multiplying the result by one hundred in order to obtain the percentage nucleotide (or amino acid) identity of the two sequences with respect to one another.

The optimal alignment of the sequences for the comparison may be carried out by computer using known algorithms.

Entirely preferably, the percentage sequence identity is determined using the Clustal W software (version 1.82), the parameters being set as follows: (1) CPU MODE=ClustalW mp; (2) ALIGNMENT="full"; (3) OUTPUT FORMAT="aln w/numbers"; (4) OUTPUT ORDER="aligned"; (5) COLOR ALIGNMENT="no"; (6) KTUP (word size)="default"; (7) WINDOW LENGTH="default"; (8) SCORE TYPE="percent"; (9) TOPDIAG="default"; (10) PAIRGAP="default"; (11) PHYLOGENETIC TREE/TREE TYPE="none"; (12) MATRIX="default"; (13) GAP OPEN="default"; (14) END GAPS="default"; (15) GAP EXTENSION="default"; (16) GAP DISTANCES="default"; (17) TREE TYPE="cladogram" and (18) TREE GRAPH DISTANCES="hide".

More particularly, the present invention also relates to the sequences in which the amino acid sequence has 100% amino acid identity with amino acids 225 to 450 of the sequences SEQ ID NO: 1 to 9, or 100% amino acid identity with amino acids 2130 to 2170 of the sequence SEQ ID NO: 12, and at least 80%, 81%, 82%, 83%, 84%, 85%, 86%, 87%, 88%, 89%, 90%, 91%, 92%, 93%, 94%, 95%, 96%, 97%, 98%, 99% or 100% amino acid identity with the rest of the sequences SEQ ID NO: 1 to 12 as previously defined, and a biological activity of the same nature.

Among the sequences of interest of the invention, some of them prove to be more particularly advantageous in terms of glucosylation activity.

Thus, according to one embodiment, the glucansucrases preferentially used in a process of the invention are chosen from the group comprising:

a sequence having at least 80% identity with SEQ ID NO: 1, said sequence having an amino acid $X_1$ representing an amino acid chosen from the group consisting of H, N or S;

a sequence having at least 80% identity with SEQ ID NO: 2, said sequence having an amino acid $X_2$ representing an amino acid chosen from the group consisting of A, C, F, L, M, S or V;

a sequence having at least 80% identity with SEQ ID NO: 3, said sequence having an amino acid $X_3$ representing an amino acid chosen from the group consisting of A and N;

a sequence having at least 80% identity with SEQ ID NO: 4, said sequence having an amino acid $X_4$ representing an amino acid chosen from the group consisting of C, I, N, P, V or W;

a sequence having at least 80% identity with SEQ ID NO: 5, said sequence having an amino acid $X_5$ representing an amino acid chosen from the group consisting of C, K, R or V;

a sequence having at least 80% identity with SEQ ID NO: 9, said sequence having an amino acid $X_8$ representing an amino acid chosen from the group consisting of C or L; and a sequence having at least 80% identity with SEQ ID NO: 12, said sequence having amino acids $X_9, X_{10}, X_{11}, X_{12}$ and $X_{13}$, with:

(i) $X_9$ representing an amino acid chosen from the group consisting of G, V, C and F;

$X_{10}$ representing F; $X_{11}$ representing A; $X_{12}$ representing F; and $X_{13}$ representing L;

(ii) $X_9$ representing, independently of $X_{10}, X_{11}, X_{12}$ and $X_{13}$, an amino acid chosen from the group consisting of S, N, L and I;

$X_{10}$ representing, independently of $X_9, X_{11}, X_{12}$ and $X_{13}$, an amino acid chosen from the group consisting of L, I, H and Y;

$X_{11}$ representing A; $X_{12}$ representing F; and $X_{13}$ representing L;

(iii) $X_9$ representing W; $X_{10}$ representing F; $X_{11}$ representing A or E; $X_{12}$ representing L and $X_{13}$ representing L; or said sequence having at least 80% identity with SEQ ID NO: 12 is the sequence SEQ ID NO: 13.

According to one preferred mode, a sequence having at least 80% identity with SEQ ID NO: 12, having the amino acids $X_9, X_{10}, X_{11}, X_{12}$ and $X_{13}$, is such that:

(i) $X_9$ represents an amino acid chosen from the group consisting of G, V, C and F;

$X_{10}$ represents F; $X_{11}$ represents A; $X_{12}$ represents F; and $X_{13}$ represents L;

(ii) $X_9$ represents, independently of $X_{10}, X_{11}, X_{12}$ and $X_{13}$, an amino acid chosen from the group consisting of S and I;

$X_{10}$ represents, independently of $X_9, X_{11}, X_{12}$ and $X_{13}$, an amino acid chosen from the group consisting of L, I and Y; represents A; $X_{12}$ represents F; and $X_{13}$ represents L; or (iii) $X_9$ represents W; $X_{10}$ represents F; $X_{11}$ represents A or E; $X_{12}$ represents L and $X_{13}$ represents L; or said sequence having at least 80% identity with SEQ ID NO: 12 is the sequence SEQ ID NO: 13.

The mutants that are more particularly advantageous according to the invention, of SEQ ID NO: 12, are in particular indicated in example 11 of the present application.

The enzymes of which the sequences have at least 80% identity with SEQ ID NO 1 to 11 all in fact exhibit a glucosylation efficiency on the flavonoids of the invention which is 5%, 10%, 15%, 20%, 25%, 30%, 35%, 40%, 45%, 50%, 55% or 60% greater compared respectively to an activity of 0.5+/−0.5% or 4.7+/−1.7% for the wild-type enzyme (see in particular tables 2, 3, 5 and 6).

The enzymes of which the sequence has at least 80% identity with SEQ ID NO 12 exhibit a glucosylation efficiency on the flavonoids of the invention which is 5%, 10%, 15%, 20%, 25%, 30%, 35%, 40%, 45% or 50% greater compared respectively to an activity of 20.4+/−3.2% or 13.9+/−4.7% for the wild-type enzyme (see in particular tables 7 and 8).

Flavonoids, Derivatives and Uses a) Flavonoids Used in a Process of the Invention The flavonoids specifically used in a process of the invention are of formula (I) as previously described.

According to one embodiment, just one of the groups chosen from $R_8$, $R_9$, $R_{10}$, $R_{11}$ and $R_{12}$ represents a hydroxyl group, the other groups among $R_8$, $R_9$, $R_{10}$, $R_{11}$ and $R_{12}$, which may be identical or different, being chosen from the group comprising a hydrogen atom; a linear or branched, saturated or unsaturated $C_1$-$C_{10}$ hydrocarbon-based group, optionally interrupted with at least one heteroatom chosen from O, N or S; a halogen atom; a $C_5$-$C_9$ aryl; a $C_4$-$C_9$ heterocycle; a $(C_1$-$C_3)$alkoxy group; a $C_2$-$C_3$ acyl; a $C_1$-$C_3$ alcohol; a —COOH; —$NH_2$; —$CONH_2$; —CHO; —SH; —C(O)O ($C_2$-$C_3$) group; a $C_1$-$C_3$ amine; a $C_1$-$C_3$ imie; a nitrile group; a $C_1$-$C_3$ haloalkyl; and a $C_1$-$C_3$ thioalkyl; a —C(W) group; and an —O(W) group; W representing a chain consisting of from 1 to 6 glycoside(s).

Preferably, the $R_{10}$ group represents a hydroxyl group.

Preferably, the $R_8$, $R_9$, $R_{11}$ and $R_{12}$ groups represent hydrogen atoms. According to one preferred embodiment, the $R_{10}$ group represents a hydroxyl group and the $R_8$, $R_9$, $R_{11}$ and $R_{12}$ groups represent hydrogen atoms.

According to one embodiment, the C ring represents a ring of formula (II) or (IV) as previously defined. According to one embodiment, the C ring represents a ring of formula (II). According to another embodiment, the C ring represents a ring of formula (IV).

According to one embodiment of the invention, the $R_1$ group represents a B ring of formula (VI) as previously defined.

According to one embodiment, the C ring represents a ring of formula (II) and the $R_1$ group represents a B ring of formula (VI) as previously defined.

According to another embodiment, the C ring represents a ring of formula (IV) and the $R_1$ group represents a B ring of formula (VI) as previously defined.

According to one embodiment, the $R_1'$, $R_2$ and $R_2'$ groups represent hydrogen atoms, and $R_3$ and $R_3'$ together form an =O group.

According to one preferred embodiment, the $R_1$ group represents a B ring of formula (VI), the $R_1'$, $R_2$ and $R_2'$ groups represent hydrogen atoms, and $R_3$ and $R_3'$ together form an =O group.

According to one preferred embodiment, the C ring represents a ring of formula (II) or (IV), the $R_1$ group represents a B ring of formula (VI), the $R_1'$, $R_2$ and $R_2'$ groups represent hydrogen atoms, and $R_3$ and $R_3'$ together form an =O group.

According to one embodiment, two of the $R_4$, $R_8$, $R_6$ and $R_7$ groups represent a hydroxyl group, the other two groups being as previously defined. Preferably, the two groups representing a hydroxyl group are the $R_4$ and $R_6$ groups.

According to one embodiment, two of the $R_4$, $R_5$, $R_6$ and $R_7$ groups represent a hydroxyl group, the other two groups representing a hydrogen atom.

According to one embodiment, the $R_5$ and $R_7$ groups represent hydrogen atoms.

According to one preferred embodiment, the $R_4$ and $R_6$ groups represent a hydroxyl group and the $R_5$ and $R_7$ groups represent a hydrogen atom.

According to another embodiment, $R_8$ and just one of the groups chosen from $R_{10}$, $R_{11}$ and $R_{12}$ represent a hydroxyl group, $R_9$ and the other groups among $R_{10}$, $R_{11}$ and $R_{12}$, which may be identical or different, being chosen from the group comprising a hydrogen atom; a linear or branched, saturated or unsaturated $C_1$-$C_{10}$ hydrocarbon-based group, optionally interrupted with at least one heteroatom chosen from O, N or S; a halogen atom; a $C_5$-$C_9$ aryl; a $C_4$-$C_9$ heterocycle; a $(C_1$-$C_3)$alkoxy group; a $C_2$-$C_3$ acyl; a $C_1$-$C_3$ alcohol; a —COOH; —$NH_2$; —$CONH_2$; —CHO; —SH; —C(O)O ($C_2$-$C_3$) group; a $C_1$-$C_3$ amine; a $C_1$-$C_3$ imine; a nitrile group; a $C_1$-$C_3$ haloalkyl; a $C_1$-$C_3$ thioalkyl; a —C(W) group; and an —O(W) group; W representing a chain consisting of from 1 to 6 glycoside(s).

Preferably, the $R_{10}$ group represents a hydroxyl group.

Preferably, the $R_9$, $R_{11}$ and $R_{12}$ groups represent hydrogen atoms.

According to one preferred embodiment, the $R_8$ and $R_{10}$ groups represent a hydroxyl group and the $R_9$, $R_{11}$ and $R_{11}$ groups represent hydrogen atoms.

According to one embodiment, the C ring represents a ring of formula (II) or (IV), preferably (II), as previously defined.

According to one embodiment of the invention, the $R_1$ group represents a B ring of formula (VI) as previously defined.

According to one embodiment, the $R_1'$ and $R_2'$ groups represent hydrogen atoms, $R_2$ represents a hydrogen atom or an —OH group, preferably an —OH group, and $R_3$ and $R_3'$ together form an =O group.

According to one preferred embodiment, the $R_1$ group represents a B ring of formula (VI), the $R_1'$ and $R_2'$ groups represent hydrogen atoms, $R_2$ represents an —OH group, and $R_3$ and $R_3'$ together form an =O group.

According to one preferred embodiment, the C ring represents a ring of formula (II), the $R_1$ group represents a B ring of formula (VI), the $R_2$ group represents an —OH group, and $R_3$ and $R_3'$ together form an =O group.

According to one embodiment, a flavonoid used in a process of the invention is of formula (VII), (VIII) or (IX) below:

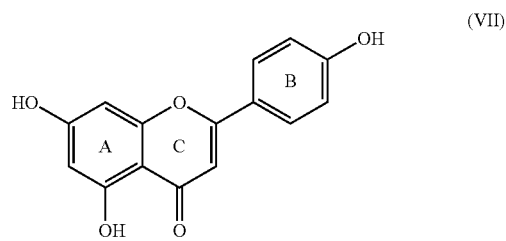

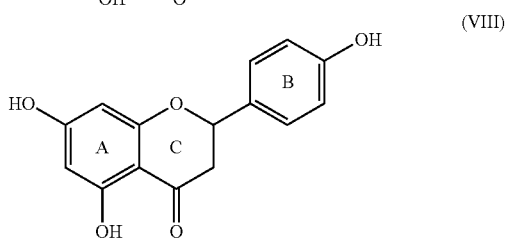

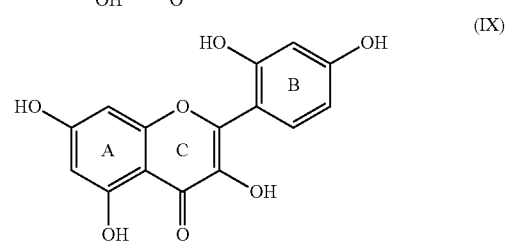

A flavonoid of the invention may be used in a process of the invention at a sucrose to flavonoid molar ratio of between 1 and 35 000, the reaction mixture comprising at least the enzyme(s), the sucrose and the receptor flavonoid(s).

Preferably, the sucrose to flavonoid molar ratio is between 7 and 292, the reaction mixture comprising at least the enzyme(s), the sucrose and the receptor flavonoid(s).

b) O-α-Glucosylated Flavonoid Derivatives

The present invention also relates to certain O-α-glucosylated flavonoid derivatives. They are capable of being obtained from a process of the invention.

The present invention is more particularly directed toward compounds of formula (X) below:

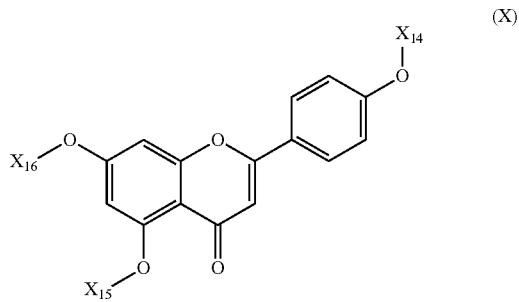

in which $X_{14}$ represents a chain consisting of at least two α-glucoside groups, and $X_{15}$ and $X_{16}$, which may be identical or different, are chosen from the group comprising a hydrogen atom; a linear or branched $C_1$-$C_6$ alkyl; a —C(O)O($C_2$-$C_3$) group; and a chain consisting of from 1 to 600 000 α-glucoside groups.

As illustrated in Moulis et al. Understanding the polymerization mechanism of glycoside-hydrolase family 70 glucansucrases, J. Biol. Chem. 2006, 281: 31254-31267, a compound according to the invention, and glucosylated using a glucansucrose in accordance with the invention, may in fact comprise a chain consisting of from 1 to 600 000 α-glucoside groups.

The present invention is also directed toward compounds of formula (XI) below:

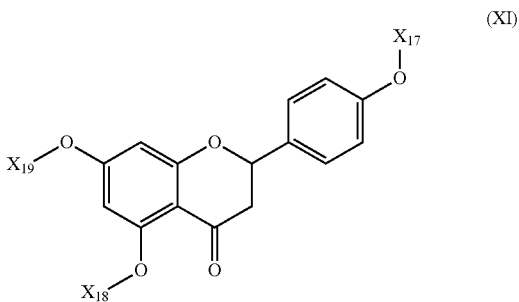

in which $X_{17}$ represents a chain consisting of from 1 to 600 000 α-glucoside groups, and $X_{18}$ and $X_{19}$, which may be identical or different, are chosen from the group comprising a hydrogen atom; a linear or branched $C_1$-$C_6$ alkyl; a —C(O)O($C_2$-$C_3$) group; and a chain consisting of from 1 to 600 000 α-glucoside groups.

c) Use of the O-α-Glucosylated Flavonoid Derivatives of the Invention

According to one embodiment, the O-α-glucosylated flavonoid derivatives of the invention may be used as an antioxidant (Heim et al., J. Nutr. Biochem., 2002, 13: 572-584).

According to one embodiment, the O-α-glucosylated flavonoid derivatives of the invention may be employed for the pharmaceutical use thereof in the treatment and/or prevention of hepatotoxicity, allergies, inflammation, ulcers, tumors, menopausal disorders or neurodegenerative diseases (Harborne J. et al., Phytochemistry, 2000, 55: 481-504; Quideau S. et al., Angew. Chem. Int. End. 2011, 50: 586-621).

According to one embodiment, the O-α-glucosylated flavonoid derivatives of the invention may be employed for the pharmaceutical use thereof as a veinotonic (Katsenis K., Curr. Vasc. Pharmacol. 2005, 3(1), 1-9).

Furthermore, according to one embodiment of the invention, the O-α-glucosylated flavonoid derivatives of the invention may be used as:

a photovoltaic agent (see in particular in this respect the document Meng et al., Nano Lett. 2008, 8(10), 3266-72; Narayan M. R., Renew. Sust. Energ. Rev. 2012, 16, 208-215; US 2009/0071534 A1);

an insect repellent (see in particular in this respect the documents JP 2002060304; JP 2003104818; Benavente-garcia et al., J. Agric. Food Chem., 1997, 45 (12), 4505-4515; Singh et al., Natural product sciences, 1997, 3(1), 49-54; Diwan and Saxena, Int. J. Chem. Sci., 2010, 8(2), 777-782; Regnault-Roger et al., J. Stored Prod Res, 2004, 40, 395-408);

a bleaching agent (see in particular in this respect the document Barkat Ali Khan et al., Asian J. Chem., 2011, 23(2), pp 903-906; patent applications WO 2008140440 A1; WO 2005094770 A1; Zhu W. & Gao J., J. Invest. Dermatol. Symposium Proceedings, 2008, 13, 20-24; Kim J. H. et al., J. Invest. Dermatol., 2008, 128, 1227-1235); or a pesticide, fungicide and/or bactericide (see in particular in this respect the documents WO 2013043031, CN 102477024 and CN 101002557).

The present invention is also illustrated, without in any way being limited thereto, by the examples which follow.

EXAMPLES

Example 1: Production and Use of Recombinant Glucansucrases for Apigenin and Naringenin Glucosylation A library of 183 variants including 174 single or double mutants, constructed from the amylosucrase of *N. polysaccharea* (glycoside hydrolase family GH13) and 10 variants, constructed from the glucansucrases DSR-S, ASR and α-1,2 BrS (belonging to the GH70 family) were tested for their ability to glucosylate apigenin and naringenin.

The origin of the glucansucrases selected for the study is reported in tables 1 and 4.

Tables 1 and 4 in fact illustrate a certain number of the glucansucrases tested in the examples of the present text and specify: column 1: the organism from which the enzyme originates; column 2: the various wild-type enzymes tested and also the mutated positions of the active site of these wild-type enzymes in the mutated glucansucrases also tested; column 3: the major binding specificities during the synthesis of the natural polymer; column 4: the literature references in which these enzymes, both in wild-type forms and in mutated forms, have been described in the prior art.

These enzymes were used in recombinant form and are expressed in *Escherichia coli*.

1.1. Enzymes Production in Microplates

All of the *Escherichia coli* strains overexpressing the heterologous glucansucrases of the GH13 and GH70 families, wild-types or their mutants, are maintained in the 96-well microplate format in order to facilitate the future flavonoid glucosylation screening steps.

Starting from the source microplates, a preculture of these *E. coli* strains is carried out for 22 hours at 30° C., 700 rpm in 96-well microplates, in 200 µl of LB culture medium supplemented with 100 µg/ml of ampicillin.

These precultures are in turn used to inoculate the "deep-well" microplates, each well of which contains 1 ml per well of ZYM5052 auto-induction medium containing in particular 0.2% (w/v) of α-lactose, 0.05% (w/v) of D-glucose, 0.5% (w/v) of glycerol and 0.05% (w/v) of L-arabinose (Studier et al., 2005).

After 22 hours of culture at 30° C. and at 700 rpm, the cell suspension is centrifuged for 20 minutes at 3000 g at 4° C. The cell pellets are resuspended in the 96-well deep-well microplates, with 300 µl of phosphate buffered saline (24 mM sodium/potassium phosphate and 274 mM NaCl) containing 0.5 g/l of lysozyme and 5 mg/l of bovin pancreatic RNAse.

An incubation is then carried out for 30 minutes at 30° C. with shaking, these microplates then being stored overnight at −80° C. After thawing, the microplates are vigorously shaken and then centrifuged for 20 minutes at 3000 g at 4° C.

The centrifuged cell lysates containing the recombinant enzymes are transferred into clean deep-well 96-well microplates.

1.2. Implementation of the Acceptor Reactions

The enzymatic extracts obtained are used to carry out the flavonoid glucosylation enzymatic screening reactions. The enzymatic activity of each centrifuged cell lysate is evaluated in the microplate format, by final weight after 30 minutes incubation in the presence of a final concentration of 146 mM of sucrose, by assaying the reducing sugars with 3,5-dinitrosalicylic acid (DNS). Finally, after dilution in ultrapure water, the absorbance is read at 540 nm.

The flavonoid acceptor reactions are then carried out in deep-well microplates, in a volume of 300 µl, at final concentrations of sucrose of 146 mM and of flavonoid of 2.5 mM (apigenin) or 5 mM (naringenin) (initially dissolved in 100% DMSO), and 140 µl of centrifuged cell lysate.

The final DMSO concentration in the reaction medium is 3% (v/v).

The incubation is carried out at 30° C. and at 700 rpm. After 24 hours, the enzymes are denatured at 95° C. for 15 minutes. These microplates are stored at −80° C. with a view to rapid evaluation of the flavonoid glucosylation by liquid-phase chromatography coupled to mass spectrometry (HPLC-MS or LC-MS).

1.3. Analytical Techniques

With a view to their analyses by HPLC-MS, the extensively homogenized reaction media are diluted to 1/30th in DMSO. The separation of the flavonoids and of their glucosylated forms is carried out in reverse phase with a ProntoSIL Eurobond® 53×3.0 mm 120-3-C18-AQ column (porosity of 120 Å, particle size of 3 µm, C18 grafting, Bischoff Chromatography, Germany).

This column is maintained at 40° C. on a Dionex Ultimate 3000 HPLC system equipped with a UV/Vis detector. This system is coupled to a single quadrupole mass spectrometer (Thermo Scientific, MSQ Plus).

The mobile phase is composed of a mixture of ultrapure water (solvent A)/acetonitrile of LC-MS quality (solvent B), each containing 0.05% (v/v) of formic acid. The separation is carried out in 10 minutes by means of a gradient of solvent B defined as follows:
 0 min, 15% (v/v);
 3 min, 25% (v/v);
 6.5 min, 49.5% (v/v);
 6.6 min, 80% (v/v);
 6.8 min, 15% (v/v); and
 10 min, 15% (v/v).

The mass spectrometry ionization on the MSQ Plus equipment is carried in positive electrospray mode (ESI+) for the apigenin and negative electrospray mode (ESI−) for the naringenin.

The capillary voltage is regulated at 3000 V, the cone voltage at 75 V. The source block temperature is set at 450° C.

The LC-MS/MS system used for the high-resolution mass spectrometry or MS/MS fragmentation analysis comprises an Ultimate 3000 chromatographic separation system (Dionex) coupled to a linear trap/Orbitrap hybrid mass spectrometer (LQT Orbitrap, Thermo Fischer Scientific). The mass spectrometry ionization on the LQT Orbitrap equipment is this time carried out either in positive electrospray mode (ESI+) or in negative electrospray mode (ESI−).

Example 2: Determination of the Efficiencies of Apigenin Glucosylation by the Recombinant Amylosucrase from *N. Polysaccharea* and by Variants Thereof The reactions in the presence of acceptor were carried out by applying the conditions described in example 1.

The flavonoid glucosylation efficiency was determined from the following formula:

Glucosylation efficiency=(Σ(area of the peak of glucosylated flavonoid(s)))/(Σ(area of the peak of glucosylated flavonoid(s))+area of the peak of residual aglycone flavonoid)×100

The flavonoid glucosylation efficiencies, expressed as a percentage, were calculated from the areas of the peaks of the various products analyzed, as described in example 1, by HPLC with a UV detector (340 nm) after 24 h of reaction.

The values obtained are reported in table 2.

Table 2 illustrates the apigenin glucosylation efficiency, during the screening of microplates, for the wild-type form of ASNp (recombinant amylosucrase from *N. polysaccharea*) and also for its 174 mutants of its active site. Along the Y-axis: the positions of mutation of the wild-type enzyme (ASNp WT); along the X-axis: the amino acid substituting that present in the sequence of the wild-type enzyme.

Thus, by way of illustration, the percentage of 1.7% indicated in row 2, column 2 was obtained using an enzyme mutated in position 226 by substitution of the amino acid R (arginine) with the amino acid A (alanine).

Each case represents a single mutation on positions R226, I228, F229, A289, F290, I330, V331, D394 and R446 or a double mutation, namely two single mutations at two of these positions.

The results obtained for the wild-type enzyme are indicated above table 2 and also at the intersections R226R, I228I, F229F, A289A, F290F, I330I, V331V, D394D and R446R.

The three double mutant variants are indicated under table 2.

For the wild-form type of the ASNp enzyme (amylosucrase *Neisseria polysaccharea*), the glucosylation efficiency is very low (0.5±0.5; n=16). The glucosylation efficiencies obtained for R226R, I228I, F229F, A289A, F290F, I330I, V331V, D394D and R446R given in table 2 are also included in the range of values 0.5±0.5.

With an apigenin glucosylation efficiency greater than that of the wild-type enzyme (greater than 1%), a large number of mutant enzymes emerge from its screening.

More particularly, with an apigenin glucosylation efficiency greater than 5%, eight enzymes emerge more particularly from the screening.

The glucosylation efficiencies for these eight mutated enzymes are respectively the following: ASNp I228F: 9.9%; ASNp I228L: 11.1%; ASNp I228M: 5.4%; ASNp F229A: 5.6%; ASNp F229N: 5.7%; ASNp A289W: 22.1%; ASNp F290C: 5.4%; and ASNp F290K: 8.9%.

This illustrates the advantage of employing enzymes derived from site-directed engineering for the glucosylation of poorly recognized acceptors such as flavonoids which are monohydroxylated or hydroxylated in a non-vicinal manner, in particular on the B ring.

Example 3: Determination of the Efficiencies of Apigenin Glucosylation by the Glucansucrases of the GH70 Family The glucansucrases of the GH70 family tested for their apigenin glucosylation activity are reported in table 4.

Table 4 illustrates the glucansucrases of the GH70 family (glycoside hydrolase 70) tested in the examples of the present text.

Thus, ASR C-APY-del WT represents the truncated form of ASR (alternansucrase), DSR-S vardelΔ4N WT represents the wild-type truncated form DSR-S (dextransucrase) and, for example, DSR-S vardelΔ4N F353T represents the truncated form of DSR-S mutated in position 353 by substitution of the amino acid F (phenylalanine) with the amino acid T (threonine).

The results of apigenin glucosylation by the glucansucrases of the GH70 family are reported in table 5.

Table 5 illustrates the apigenin glucosylation efficiency for the wild-type form of the truncated variant of DSR-S (vardelΔ4N WT), for the truncated wild-type form of ASR (ASR C-APY-del WT), for the wild-type form of the α-1,2 BrS enzyme, and for seven mutants of DSR-S vardelΔ4N.

Although the wild-type form of the truncated variant of DSR-S (DSR-S vardelΔ4N WT) exhibits only a very low glucosylation activity (0.5%), the S512C mutant exhibits a higher apigenin glucosylation efficiency (13.9%).

Figure 1:
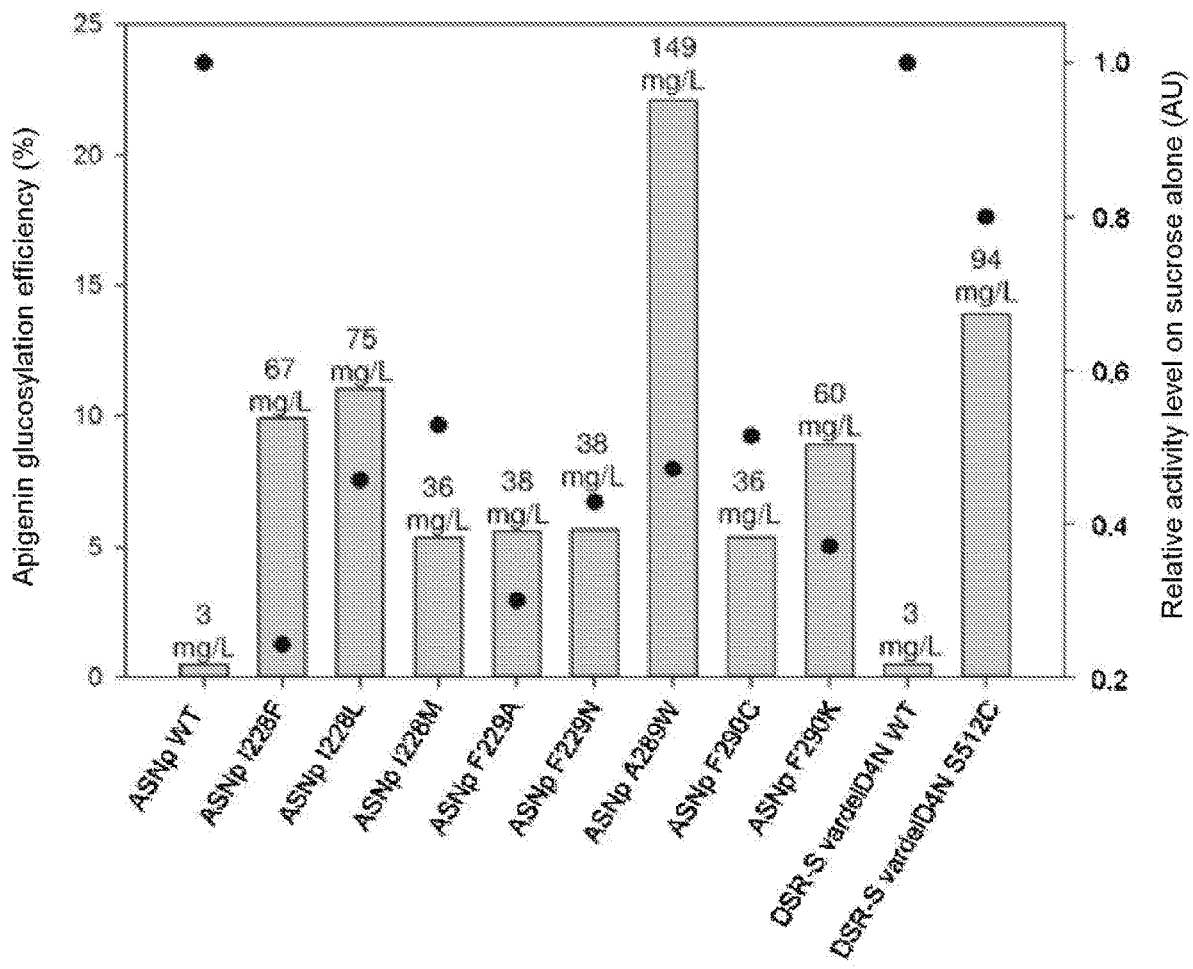
FIG. 1 illustrates the apigenin glucosylation efficiencies (histogram—left-hand y-axis—%), the relative activity levels on sucrose only (⊙ black dots—right-hand y-axis—AU) and the weight concentrations of glucosylated apigenin (values placed above the histogram—mg/L), of the enzymes ASNp WT, DSR-S vardelΔ4N WT and of their mutants ASNp I228F, ASNp I228L, ASNp I228M, ASNp F229A, ASNp F229N, ASNp A289W, ASNp F290C, ASNp F290K and DSR-S vardelΔ4N S512C.

Example 4: Comparison of the Apigenin Glucosylation Efficiencies for the Most Efficient Enzymes Among the tested enzymes of the GH13 and GH70 families, nine mutants have apigenin glucosylation efficiencies greater than 5%, namely ASNp I228F, ASNp I228L, ASNp I228M, ASNp F229A, ASNp F229N, ASNp A289W, ASNp F290C, ASNp F290K and DSR-S (vardelΔ4N S512C). These efficiencies are compared for these nine most efficient mutants, with their relative activities in the presence of sucrose alone (see FIG. 1).

The sucrose hydrolysis activities of the wild-type, ASNp WT (GH13) or DSR-S vardelΔ4N WT (GH70) enzymes were taken as references for calculating the relative sucrose hydrolysis activities of their respective mutants.

Although the mutants exhibit activities on sucrose alone that are lower than those of the wild-type enzymes, the glucosylation efficiencies of these same mutants are from 10 to 44 times greater than for the wild-type enzymes. More globally, the correlation coefficient between the apigenin glucosylation efficiencies and the sucrose hydrolysis activities, calculated for all the mutant enzymes of the amylosucrase from *N. polysaccharea*, is 0.08. This illustrates the advantage of the process for identifying enzymes that are not very active on sucrose alone but capable of glucosylating the flavonoids of the invention.

In the case of the mutant enzyme ASNp A289W, a weight concentration of 149 mg/ml of glucosylated apigenin is achieved.

This is a minimum concentration obtained in microplates. Thus, an improvement factor of 10 may be expected after optimization of the medium.

Example 5: LC-MS Analysis of the Apigenin Glucosylation Products

Figure 2:
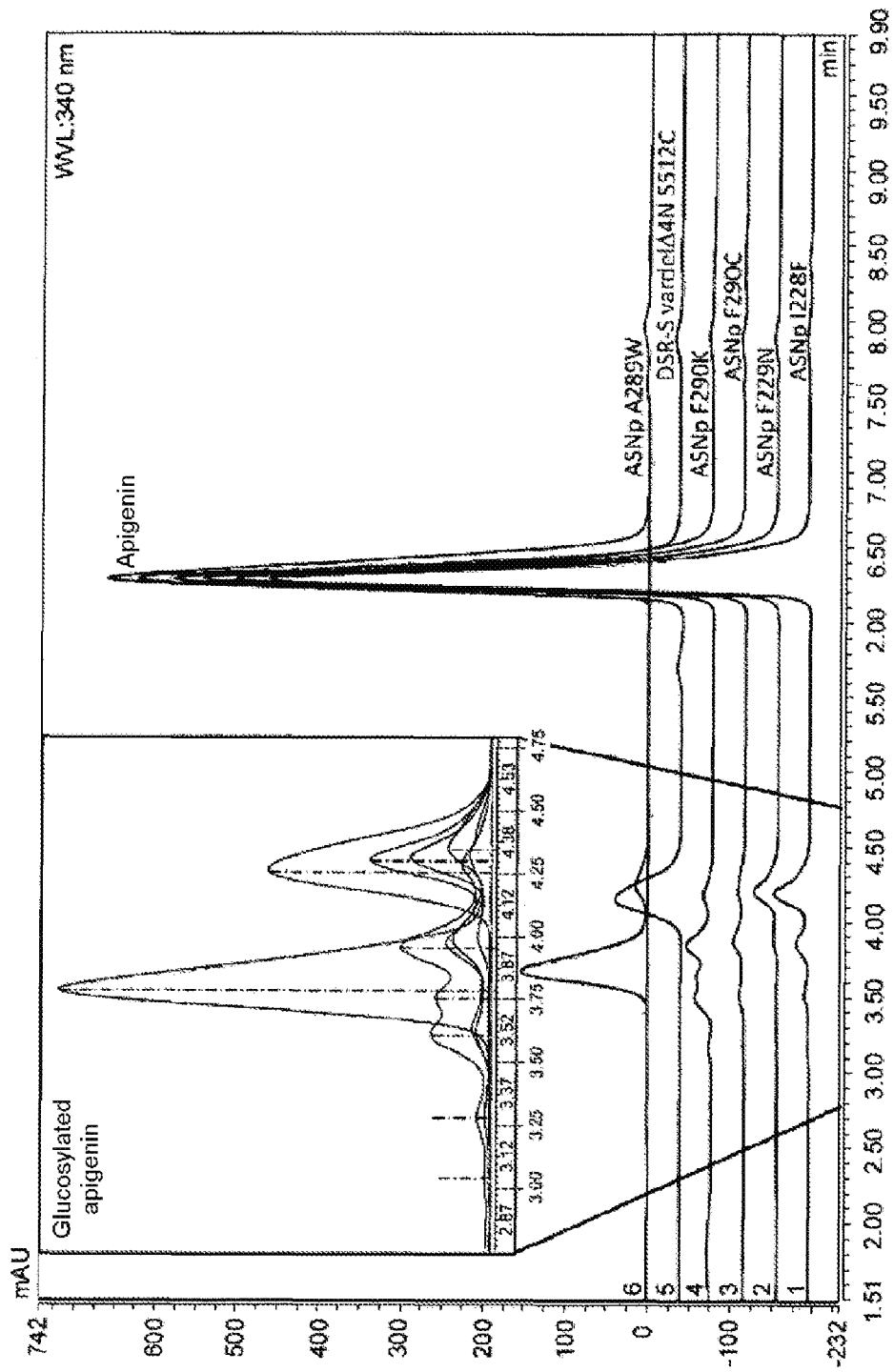
FIG. 2 illustrates the superimposition of the UV chromatograms (λ340 nm) for the six mutants representative of the six apigenin glucosylation product profile categories. The name of the enzymes corresponding to these reactions is indicated beside each chromatogram: ASNp A289W, DSR-S vardelΔ4N S512C, ASNp F290K, ASNp F290C, ASNp F229N and ASNp I228F. Along the X-axis: Retention in minutes; Along the Y-axis: Absorbance in mAU (milliabsorbance units).

The nine mutants mentioned in example 4 may be classified in six categories according to the glucosylation product profile obtained by LC-MS. The superimposition of the UV chromatograms ($\lambda$340 nm) for a representative of each of these six profile categories (respectively ASNp A289W, DSR-S (vardelΔ4N S512C), ASNp F290K, ASNp F290C, ASNp F229N and ASNp I228F) is presented in FIG. 2.

The superimposition of these chromatograms demonstrates the diversity of glucosylated apigenin forms that it is possible to obtain.

The LC-MS profiles obtained for ASNp WT and the nine most efficient mutants mentioned in example 4 are represented in FIGS. 4 to 13.

Figure 5:
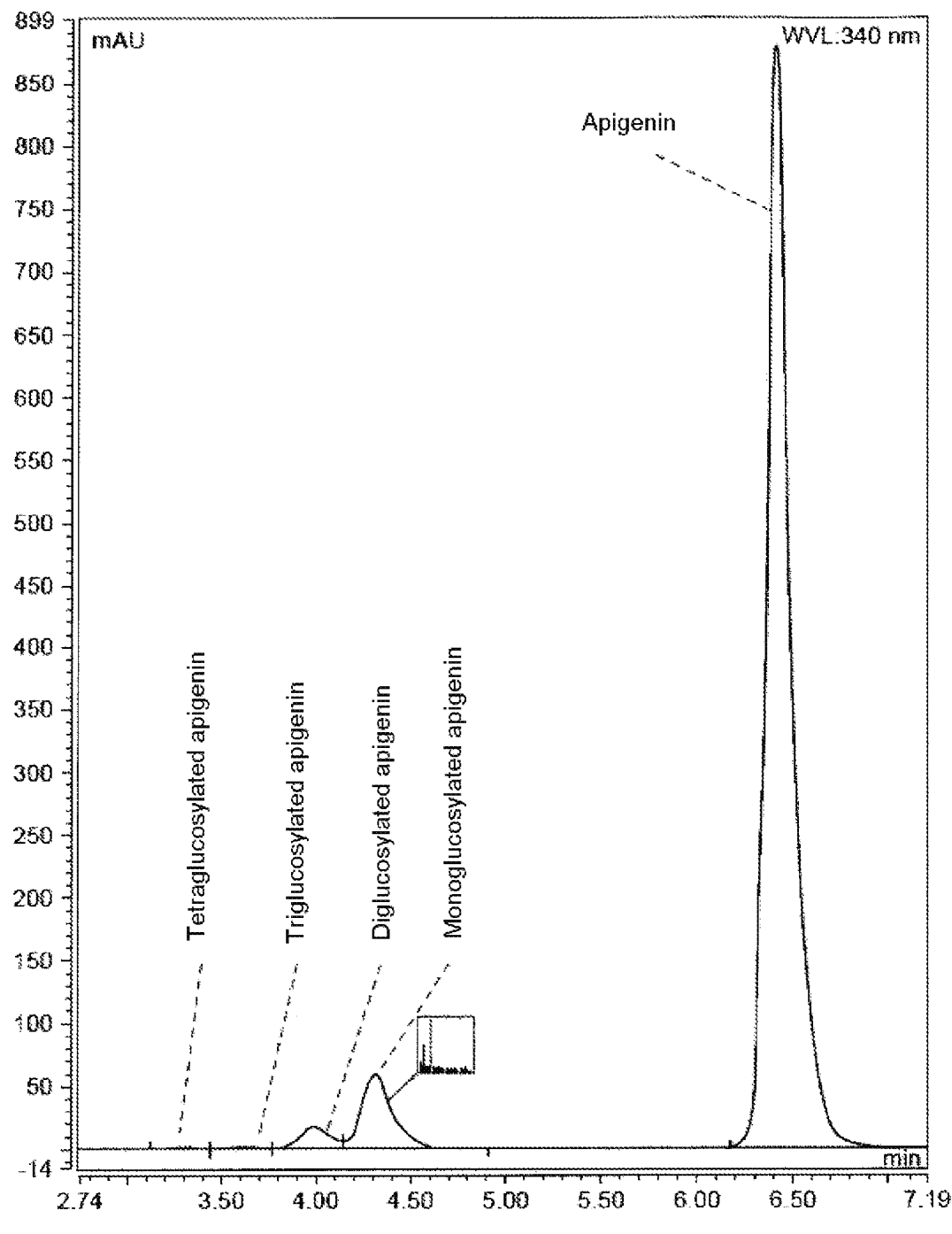
FIG. 5 illustrates the UV chromatography profile obtained after apigenin glucosylation, for the mutant enzyme ASNp I228F. Along the X-axis: Retention time in minutes; Along the Y-axis: Absorbance in mAU (milliabsorbance units). The nature of the various peaks is indicated directly on the profile.
Figure 6:
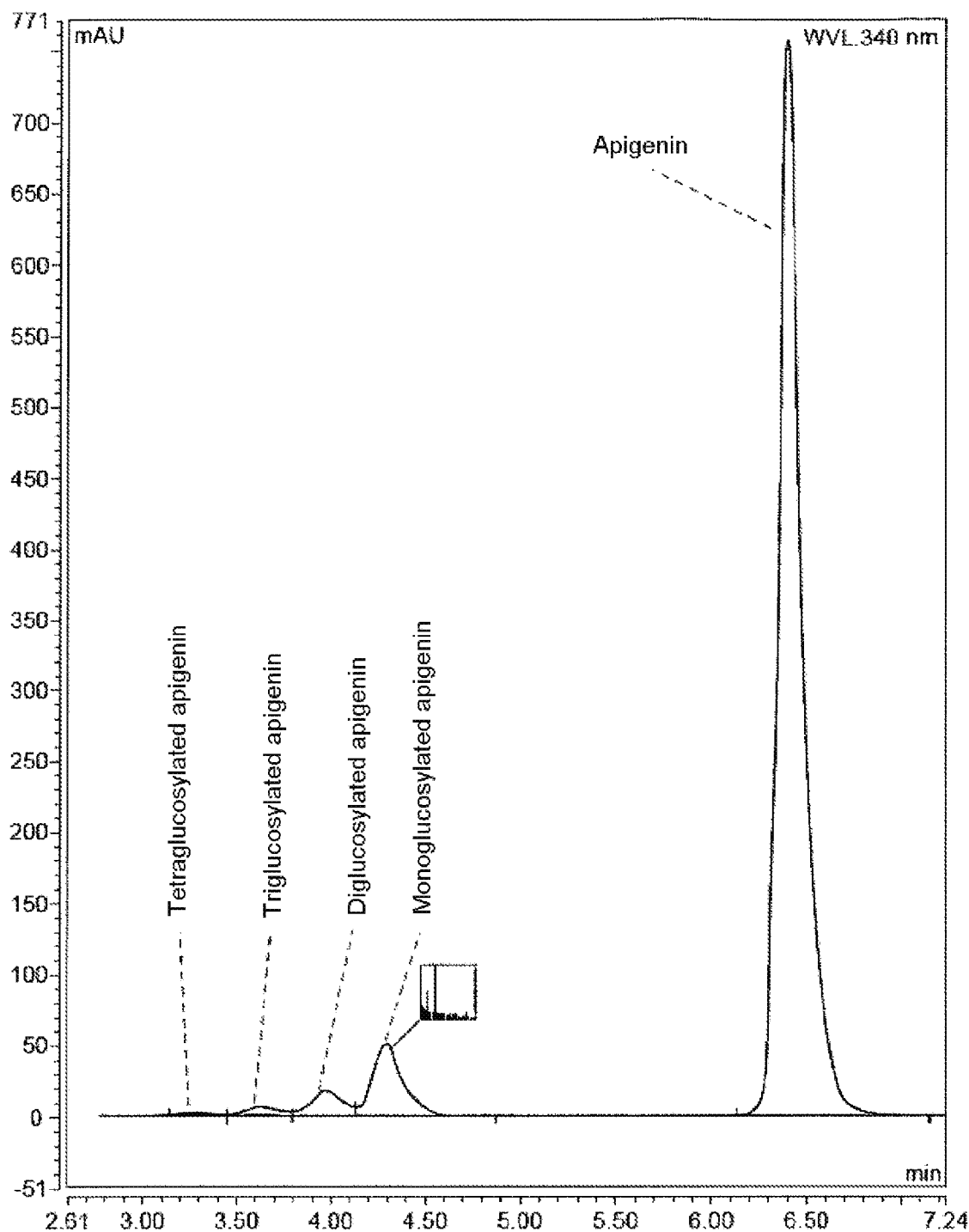
FIG. 6 illustrates the UV chromatography profile obtained after apigenin glucosylation, for the mutant enzyme ASNp I228L. Along the X-axis: Retention time in minutes; Along the Y-axis: Absorbance in mAU (milliabsorbance units).
Figure 7:
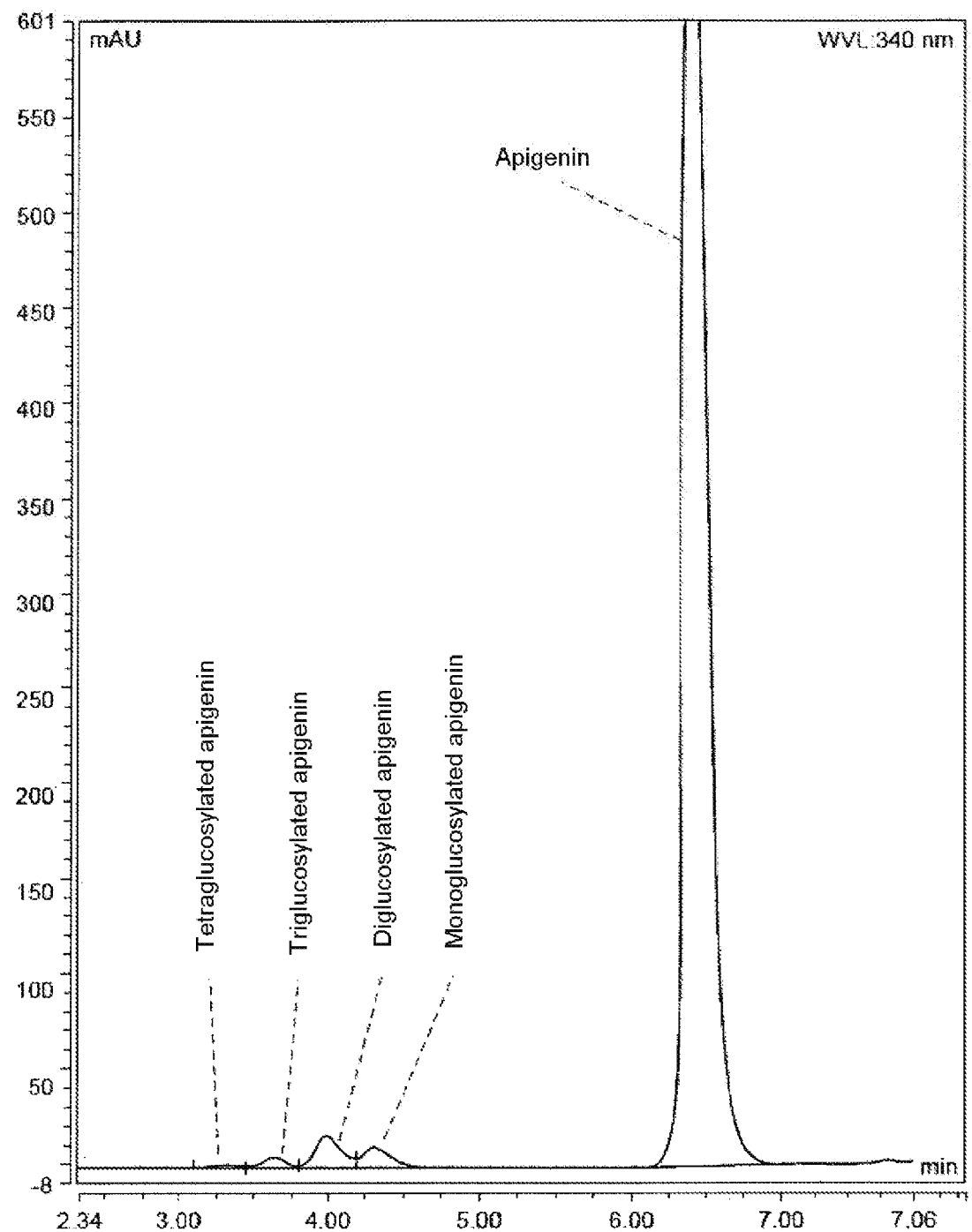
FIG. 7 illustrates the UV chromatography profile obtained after apigenin glucosylation, for the mutant enzyme ASNp I228M. Along the X-axis: Retention time in minutes; Along the Y-axis: Absorbance in mAU (milliabsorbance units). The nature of the various peaks is indicated directly on the profile.
Figure 8:
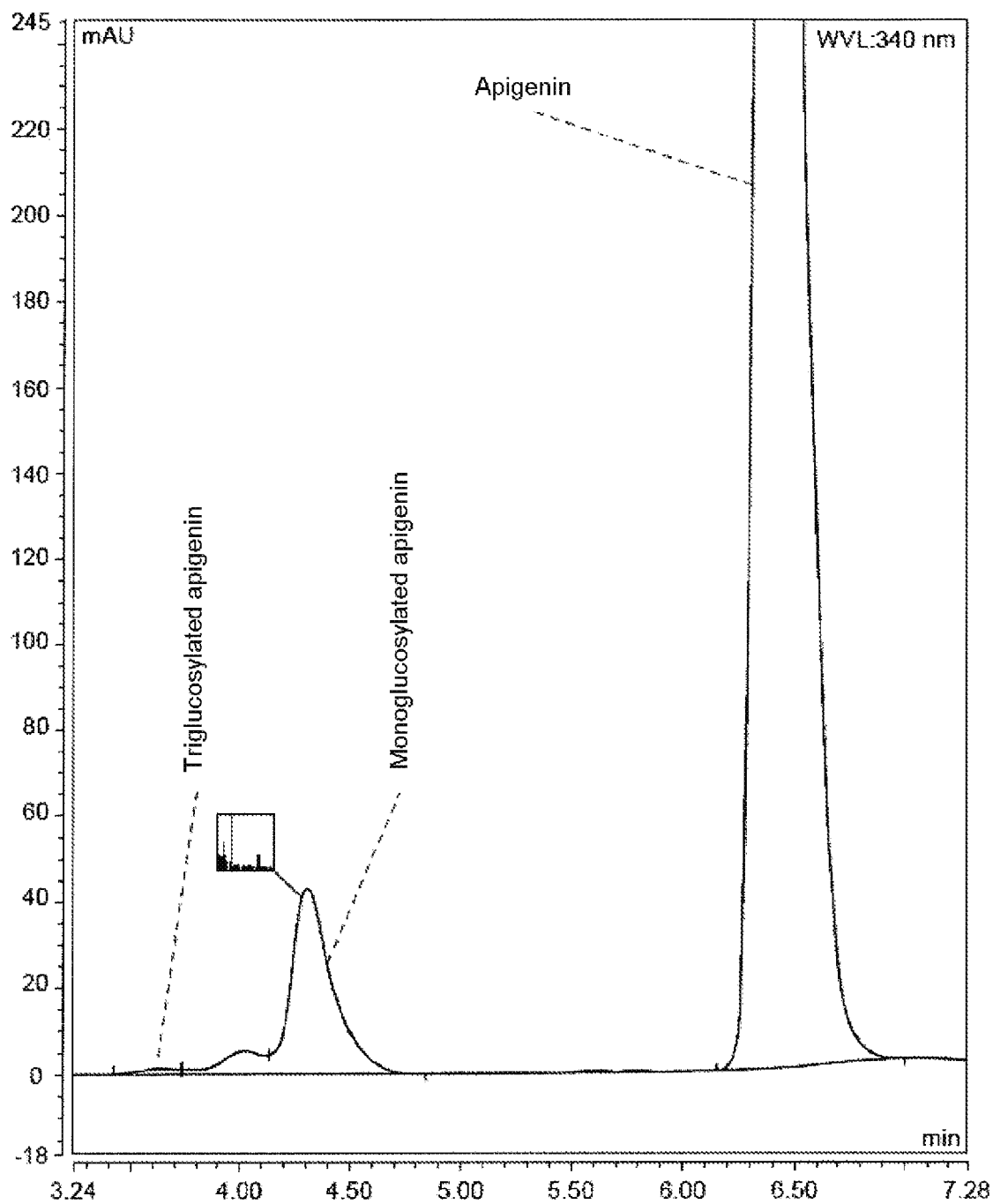
FIG. 8 illustrates the UV chromatography profile obtained after apigenin glucosylation, for the mutant enzyme ASNp F229A. Along the X-axis: Retention time in minutes; Along the Y-axis: Absorbance in mAU (milliabsorbance units). The nature of the various peaks is indicated directly on the profile.
Figure 9:
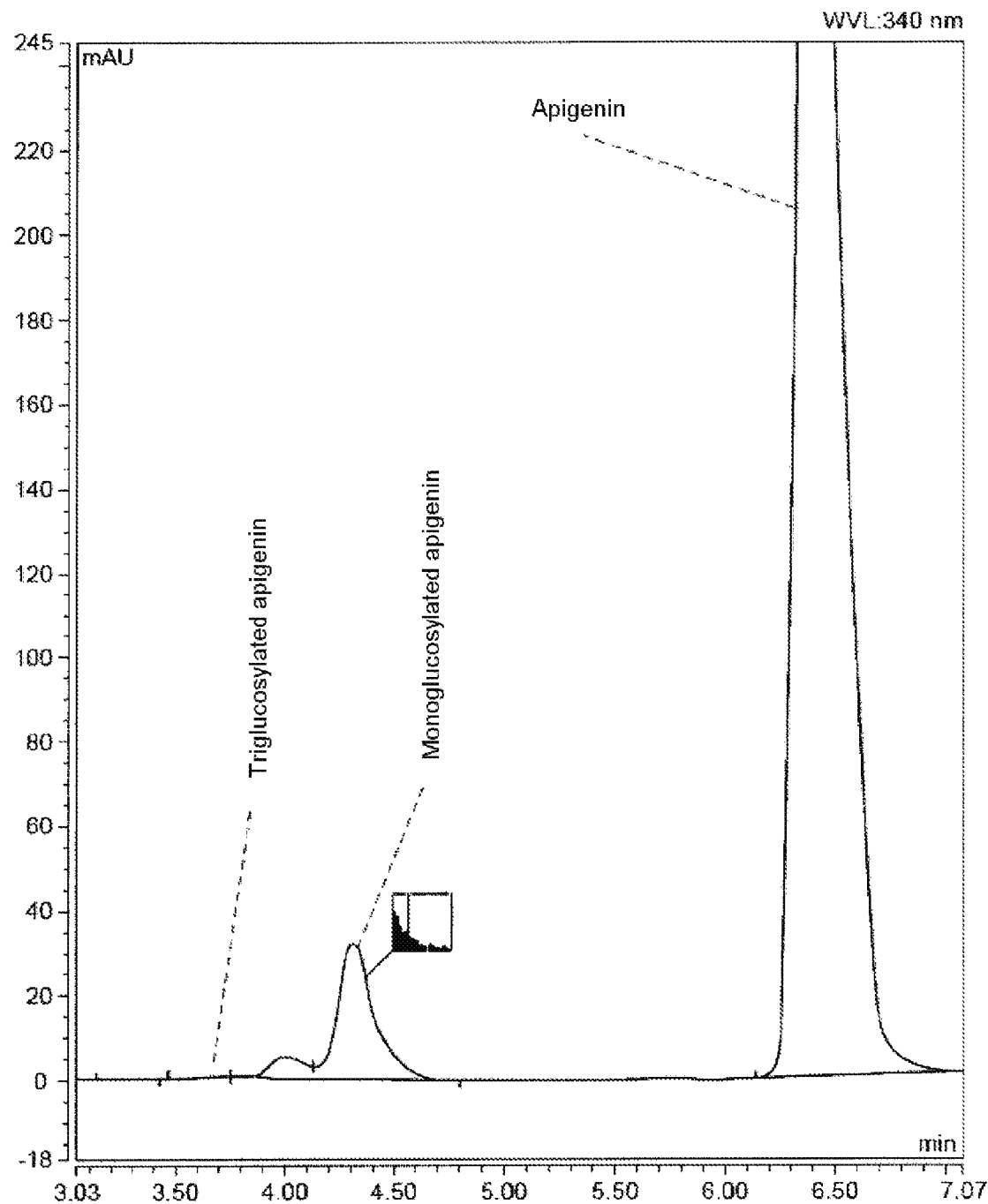
FIG. 9 illustrates the UV chromatography profile obtained after apigenin glucosylation, for the mutant enzyme ASNp F229N. Along the X-axis: Retention time in minutes; Along the Y-axis: Absorbance in mAU (milliabsorbance units). The nature of the various peaks is indicated directly on the profile.
Figure 10:
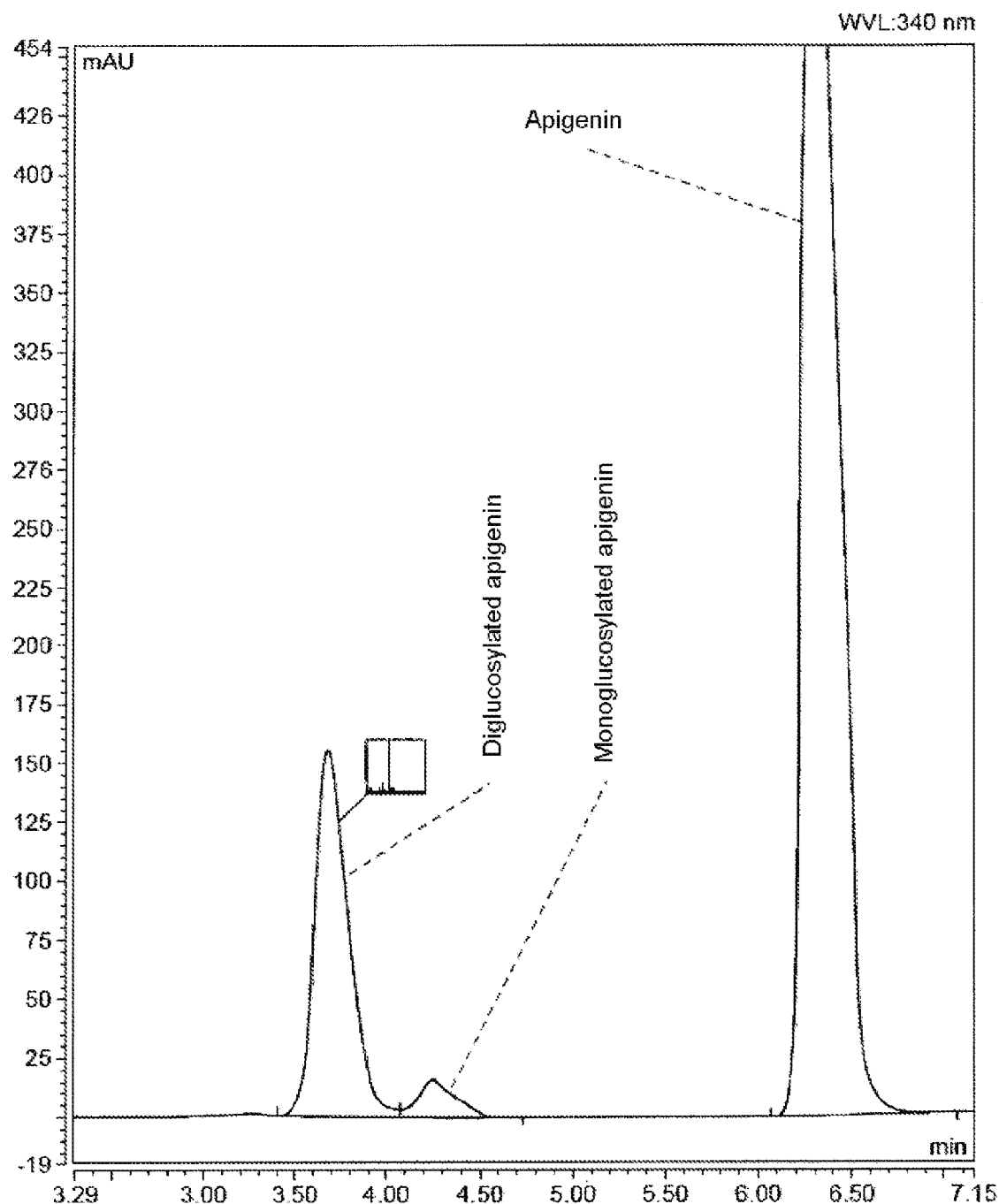
FIG. 10 illustrates the UV chromatography profile obtained after apigenin glucosylation, for the mutant enzyme ASNp A289W. Along the X-axis: Retention time in minutes; Along the Y-axis: Absorbance in mAU (milliabsorbance units). The nature of the various peaks is indicated directly on the profile.
Figure 11:
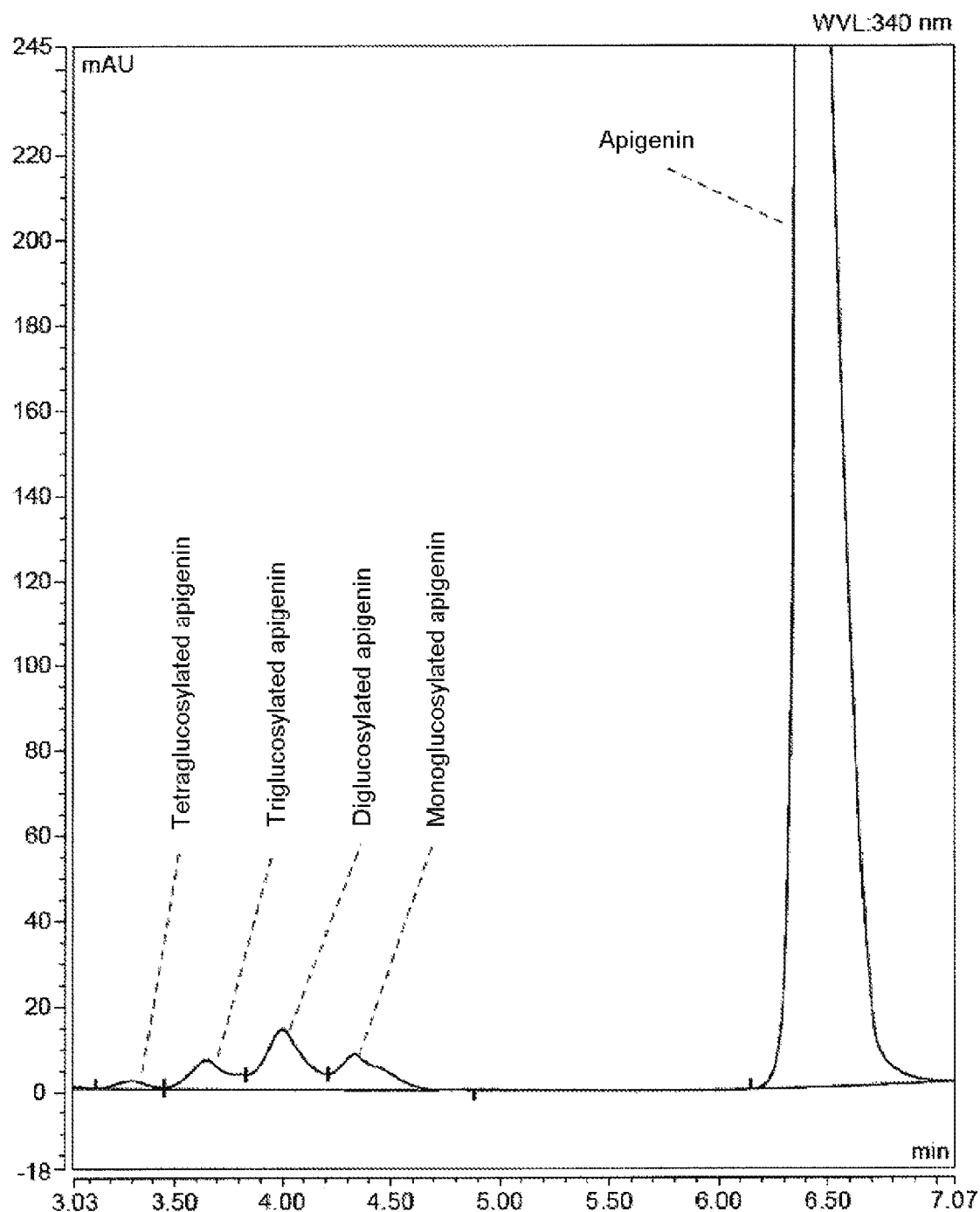
FIG. 11 illustrates the UV chromatography profile obtained after apigenin glucosylation, for the mutant enzyme ASNp F290C. Along the X-axis: Retention time in minutes; Along the Y-axis: Absorbance in mAU (milliabsorbance units). The nature of the various peaks is indicated directly on the profile.
Figure 12:
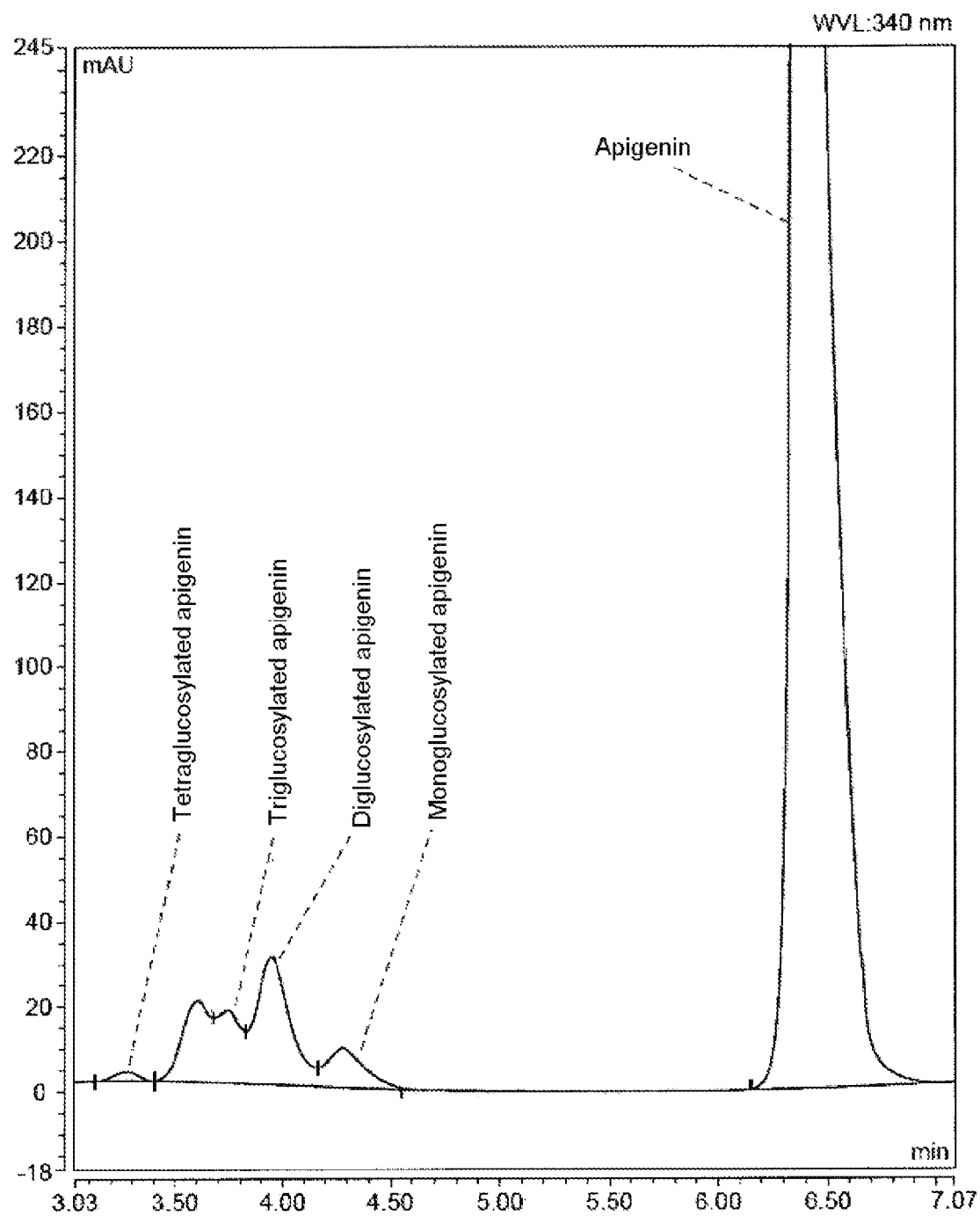
FIG. 12 illustrates the UV chromatography profile obtained after apigenin glucosylation, for the mutant enzyme ASNp F290K. Along the X-axis: Retention time in minutes; Along the Y-axis: Absorbance in mAU (milliabsorbance units). The nature of the various peaks is indicated directly on the profile.
Figure 13:
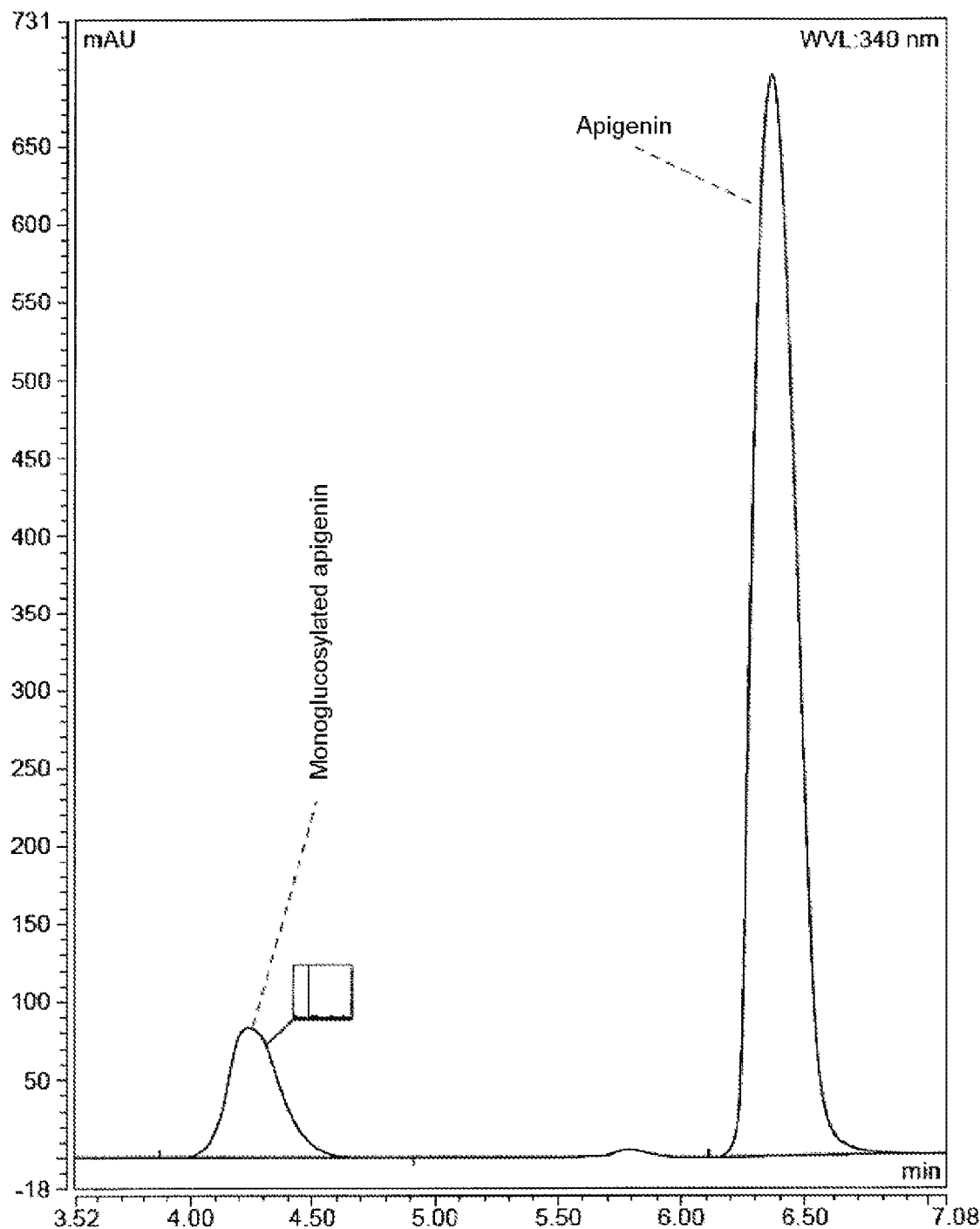
FIG. 13 illustrates the UV chromatography profile obtained after apigenin glucosylation, for the mutant enzyme DSR-S vardelΔ4N S512C. Along the X-axis: Retention time in minutes; Along the Y-axis: Absorbance in mAU (milliabsorbance units). The nature of the various peaks is indicated directly on the profile.

The molar masses, as determined by LC-MS in example 1, of the strongest glucosylated apigenin peak for each of the nine mutants are the following:

FIG. 5: 432.7 g/mol
FIG. 6: 432.7 g/mol
FIG. 7: not determined
FIG. 8: 432.8 g/mol
FIG. 9: 432.7 g/mol
FIG. 10: 594.8 g/mol
FIG. 11: data not available
FIG. 12: data not available
FIG. 13: 432.7 g/mol.

Figure 4:
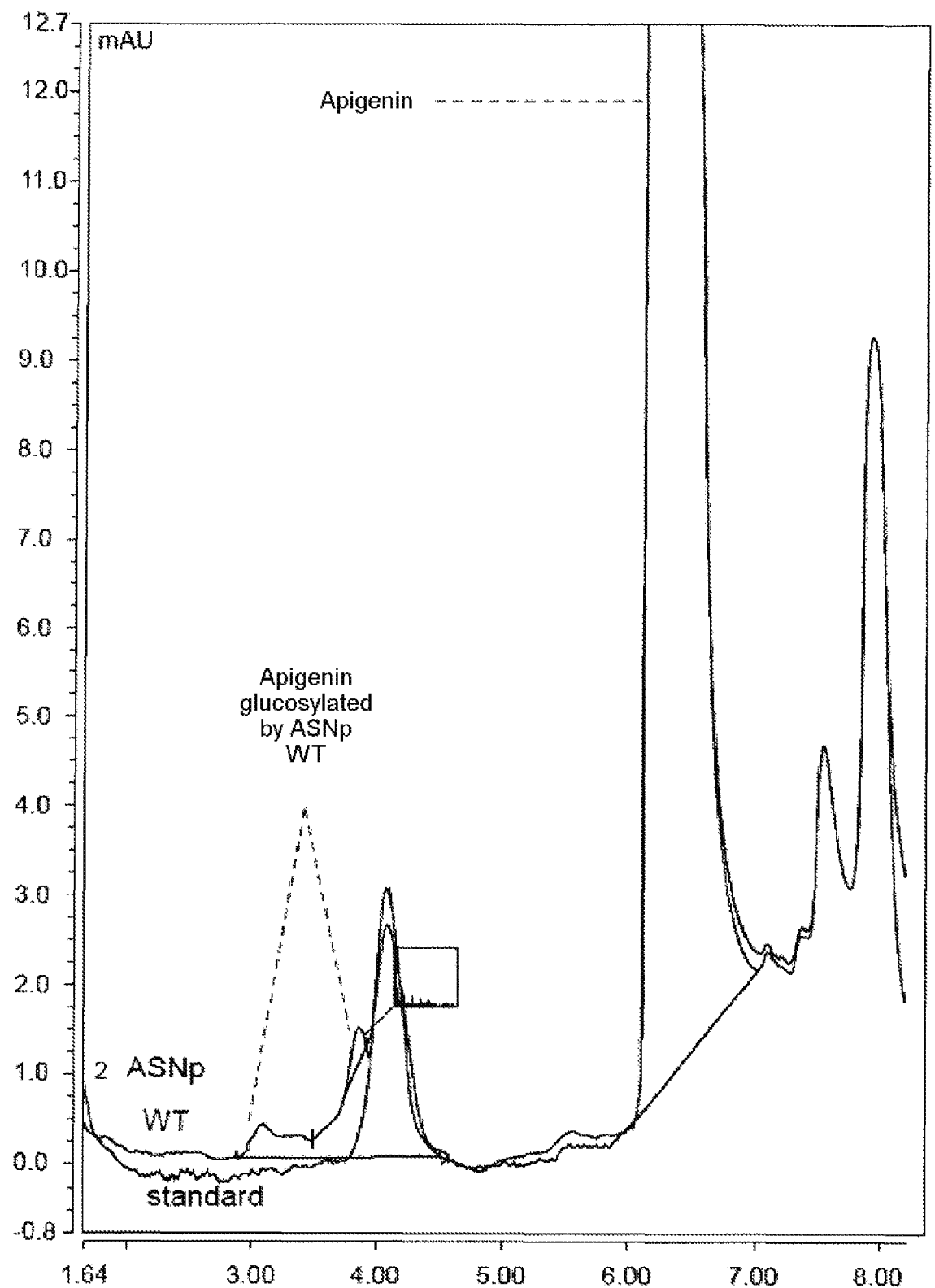
FIG. 4 illustrates the UV chromatography profile obtained after apigenin glucosylation, for the wild-type ASNp enzyme (ASNp WT), in comparison with the apigenin standard. Along the X-axis: Retention time in minutes; Along the Y-axis: Absorbance in mAU (milliabsorbance units).

The wild-type enzyme has a very low glucosylation efficiency on apigenin (0.5%). Indeed, if the apigenin standard is compared with the final products of the glucosylation reaction, the appearance, on the UV chromatogram, of several peaks, of very low strength, of glucosylated apigenin is detected (FIG. 4).

The I228F (FIG. 5), I228L (FIG. 6) and I228M (FIG. 7) mutants have product profiles which are similar to one another. However, variations between the proportions of the various forms of glucosylated apigenin are observed with the I228M mutant (FIG. 7).

The group of F229A (FIG. 8) and F229N (FIG. 9) mutants also exhibits similar product profiles.

Finally, the F290K mutant has a product profile that is more complex than that of the F290C mutant.

Example 6: High-Resolution LC-MS and LC-MS/MS Analysis of the Apigenin Glucosylation Products A study was carried out, by high-resolution LC-MS and LC-MS/MS (results obtained from Imagif), on the apigenin glucosylation products obtained with the mutant enzymes ASNp A289W and DSR-S vardelΔ4N S512C.

Figure 14:
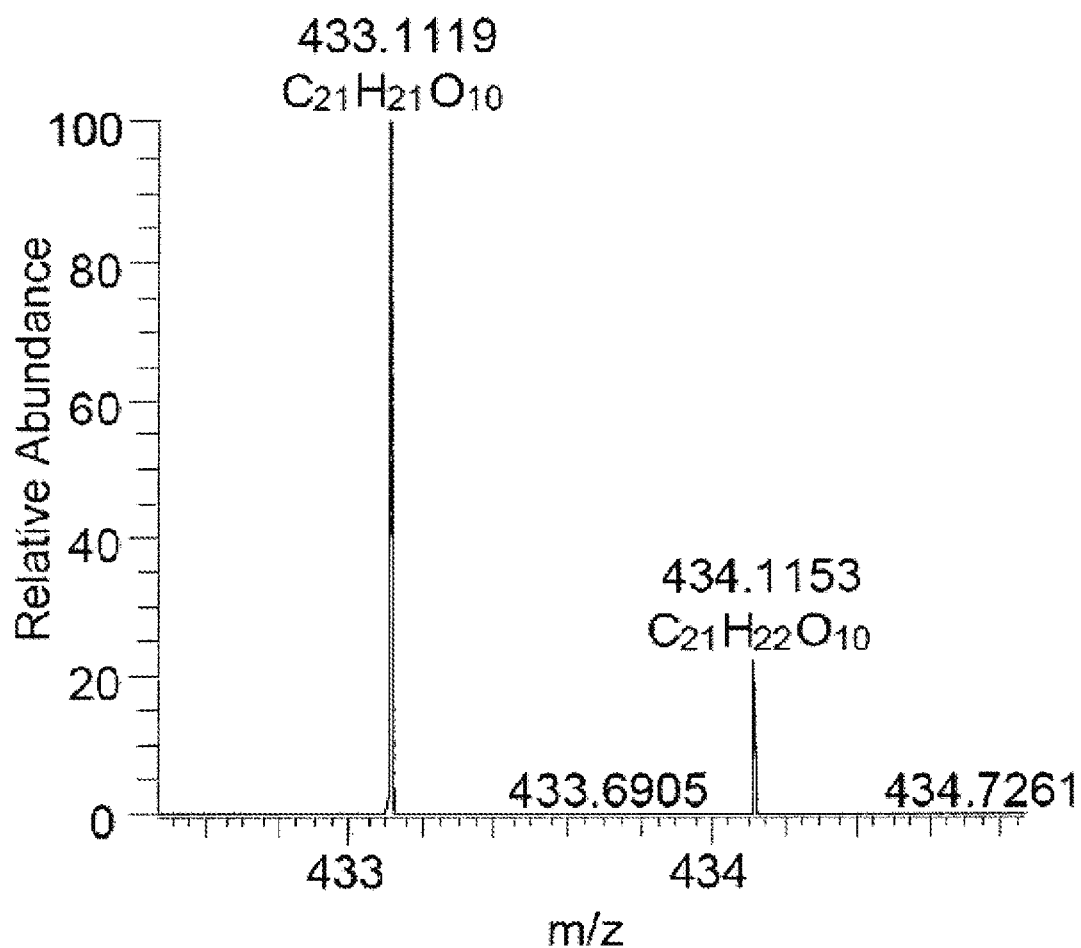
FIG. 14 illustrates the positive electrospray mode high-resolution mass spectrum for the monoglucosylated form of apigenin obtained with the mutant enzyme DSR-S vardelΔ4N S512C. Along the X-axis: m/z ratio; Along the Y-axis: relative abundance.
Figure 15:
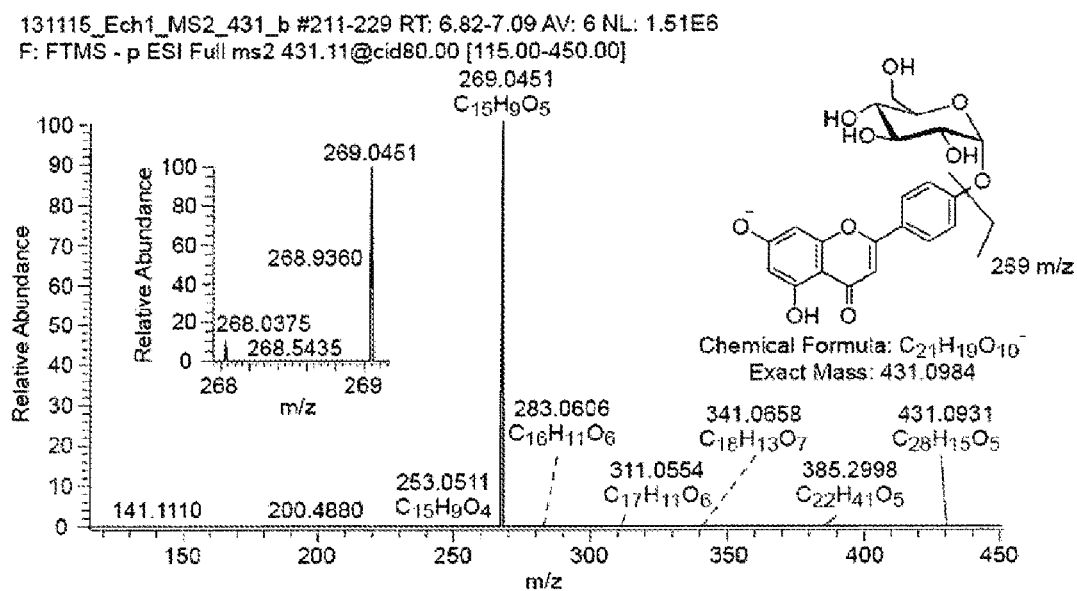
FIG. 15 illustrates the negative electrospray mode high-resolution MS/MS spectrum for the monoglucosylated form of apigenin (at m/z 431.11) obtained with the mutant enzyme DSR-S vardelΔ4N S512C. Along the X-axis: m/z ratio; Along the Y-axis: relative abundance.

The apigenin glucosylation product produced by the DSR-S vardelΔ4N S512C enzyme mutant is a monoglucosylated form (FIG. 13), the retention time of which is 4.23 min, and the m/z ratio of which in positive electrospray mode was determined at 433.1119 (FIG. 14). The negative electrospray mode LC-MS/MS analysis of this monoglucosylated form produced by DSR-S vardelΔ4N S512C resulted in the identification of two major ions, the m/z ratios of which were determined at 269.0451 and 268.9360 (FIG. 15), thus making it possible to support the obtaining of an O-glucosylation on position 4' of the B ring of apigenin.

Figure 16:
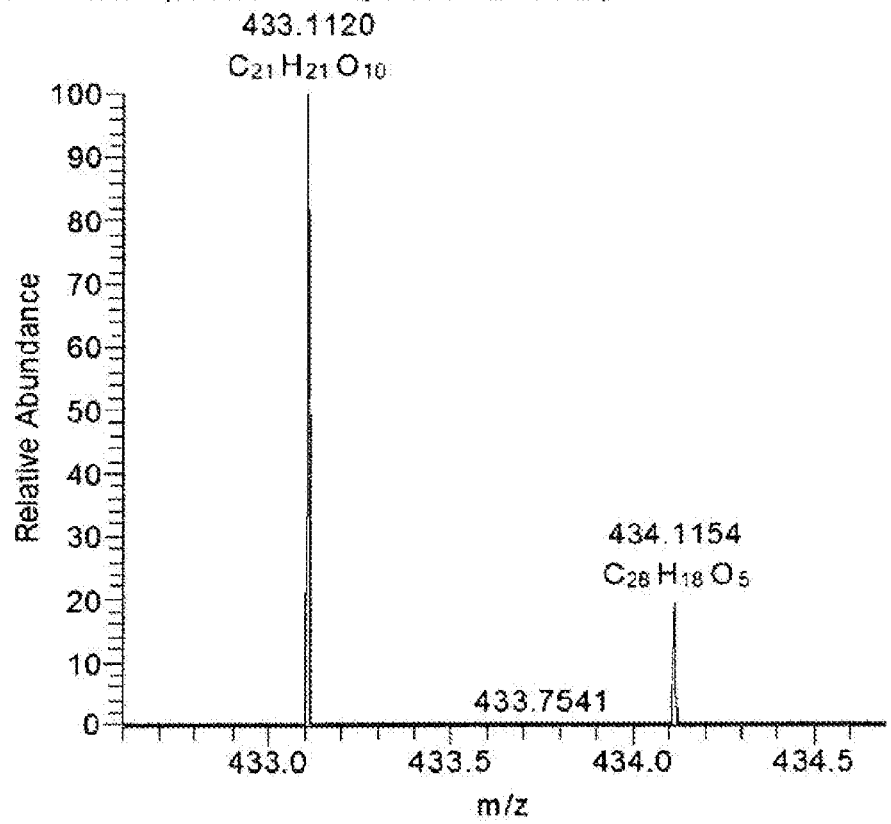
FIG. 16 illustrates the positive electrospray mode high-resolution mass spectrum for the monoglucosylated form of apigenin obtained with the mutant enzyme ASNp A289W. Along the X-axis: m/z ratio; Along the Y-axis: relative abundance.
Figure 17:
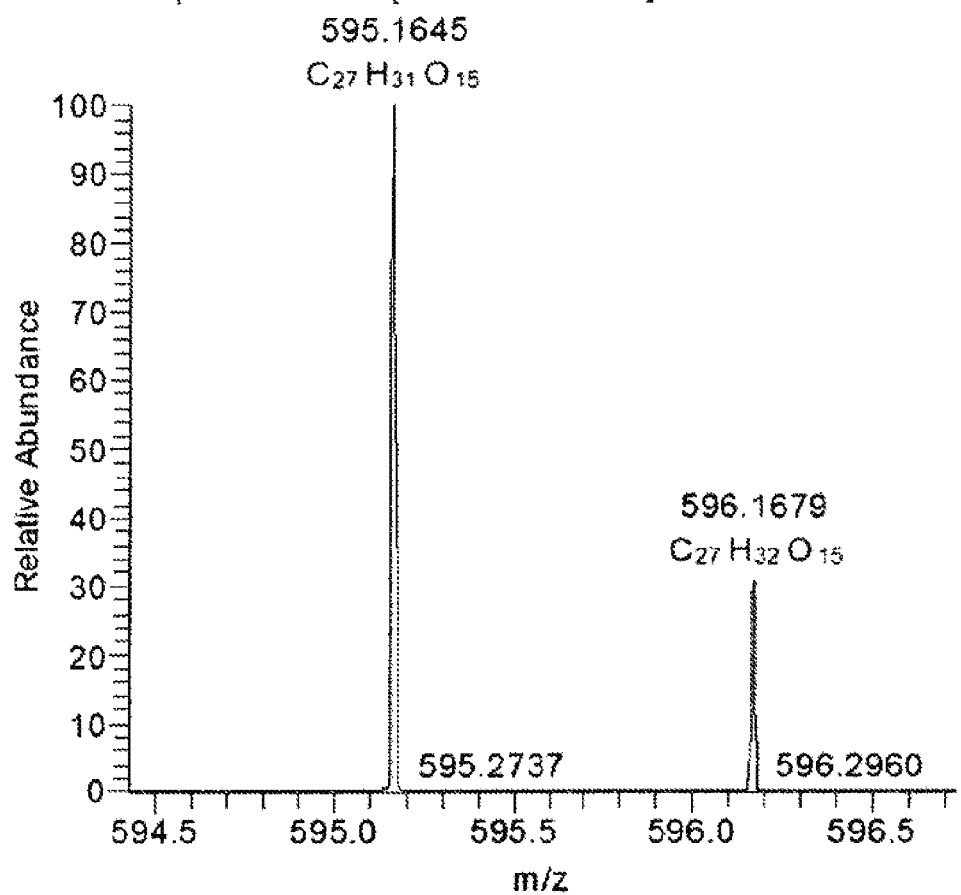
FIG. 17 illustrates the positive electrospray mode high-resolution mass spectrum for the diglucosylated forms of apigenin obtained with the mutant enzyme ASNp A289W. Along the X-axis: m/z ratio; Along the Y-axis: relative abundance.
Figure 18:
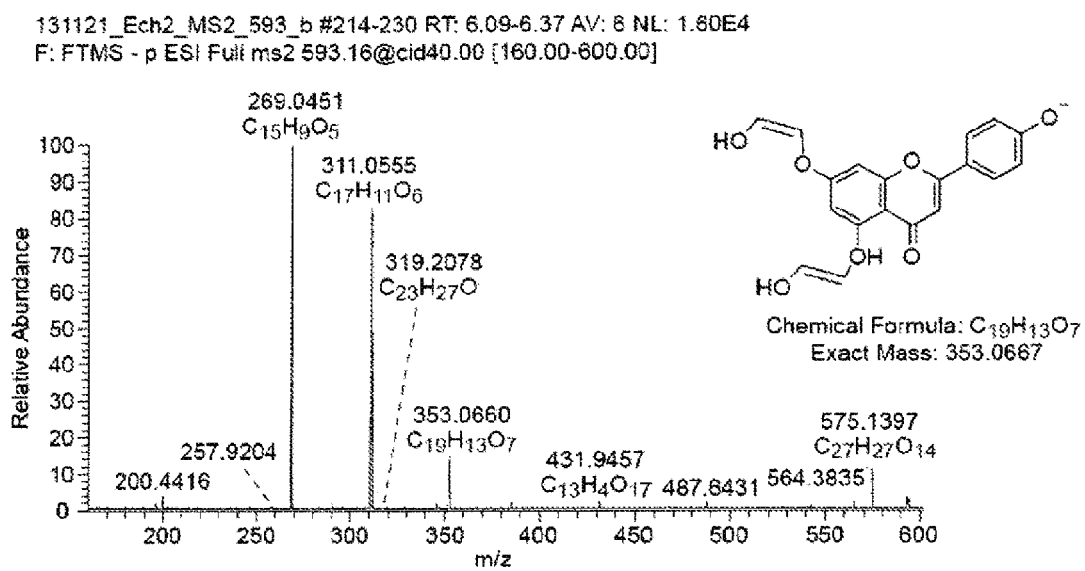
FIG. 18 illustrates the negative electrospray mode high-resolution MS/MS spectrum for one of the two diglucosylated forms of apigenin (at m/z 593.16) obtained with the mutant enzyme ASNp A289W. Along the X-axis: m/z ratio; Along the Y-axis: relative abundance.

The ASNp A289W enzyme glucosylates apigenin to give a monoglucosylated product, the retention time of which is 4.25 min (FIG. 10) and the m/z ratio of which in positive electrospray mode was determined at 433.1120 (FIG. 16). This analysis also showed that the peak of glucosylation product eluting at 3.68 min (FIG. 10) corresponds to a diglucosylation of apigenin. The m/z ratio in positive electrospray mode was determined at 595.1645 (FIG. 17). The negative electrospray mode LC-MS/MS analysis reveals that two diglucosylated forms of apigenin co-elute at 3.68 min. The negative electrospray mode LC-MS/MS analysis of the first diglucosylated form produced by ASNp A289W resulted in the identification of three major ions, the m/z ratios of which were determined at 353.0660, 311.0555 and 269.0451 (FIG. 18). This thus makes it possible to support the obtaining of a diglucosylated form for which each of positions 5 and 7 of the A ring is O-glucosylated. The negative electrospray mode LC-MS/MS analysis of the second diglucosylated form produced by ASNp A289W resulted in the identification of a single major ion, the m/z ratio of which was determined at 269.0451 (FIG. 19), thus making it possible to support the obtaining of a di-O-glucosylation on position 4' of the B ring, only, of apigenin.

Example 7: Determination of the Efficiencies of Naringenin Glucosylation by the Recombinant Amylosucrase from *N. polysaccharea* and by its Variants The reactions in the presence of acceptor were carried out by applying the conditions described in example 1.

The flavonoid glucosylation efficiency was determined from the formula set out in example 2. The flavonoid glucosylation efficiencies, expressed as a percentage, were calculated from the areas of the peaks of the various products analyzed, as described in example 1, by HPLC with a UV detector (λ340 nm), after 24 h of reaction.

The values obtained are reported in table 3.

Table 3 illustrates the naringenin glucosylation efficiency, during the screening of microplates, for the wild-type form of ASNp (recombinant amylosucrase from *N. polysaccharea*) and also for the 174 mutants of its active site. Along the Y-axis: the positions of mutation of the wild-type enzyme (ASNp WT); Along the X-axis: the amino acid substituting that present in the sequence of the wild-type enzyme.

Thus, by way of illustration, the percentage of 2.4% indicated in row 2, column 2 was obtained using an enzyme mutated in position 226 by substitution of the amino acid R (arginine) with the amino acid A (alanine).

Each case represents a single mutation on positions R226, I228, F229, A289, F290, I330, V331, D394 and R446 or a double mutation, namely two single mutations at two of these positions.

The results obtained for the wild-type enzyme are indicated at the top of table 3 and also at the intersections R226R, I228I, F229F, A289A, F290F, I330I, V331V, D394D and R446R. The results obtained for the enzymes doubly mutated on positions 289 and 290 are indicated at the bottom of table 3.

For the wild-type form of the ASNp enzyme, the glucosylation efficiency is reduced (4.7±1.7; n=16).

With a naringenin glucosylation efficiency greater than that of the wild-type enzyme (greater than 6.4%), a large number of mutant enzymes emerge from this screening.

More particularly, with a naringenin glucosylation efficiency greater than 10%, sixteen mutant enzymes emerge more particularly from the screening. Seven of these mutant enzymes have in particular a naringenin glucosylation efficiency greater than 20% and two of them have an efficiency greater than 50%.

The glucosylation efficiencies for these sixteen mutated enzymes are respectively the following: ASNp R226H: 13.5%; ASNp R226N: 16.0%; ASNp R226S: 14.1%; ASNp I228A: 70.2%; ASNp I228C: 30.9%; ASNp I228S: 16.4%; ASNp I228V: 12.3%; and ASNp A289C: 27.8%; ASNp A289I: 11.2%; ASNp A289N: 14.5%; ASNp A289P: 10.3%; ASNp A289V: 21.8%; ASNp F290R: 11.2%; ASNp F290V: 21.1%; ASNp A289P/F290C: 50.9%; ASNp A289P/F290L: 22.9%.

The naringenin glucosylation illustrates the advantage of employing enzymes resulting from site-directed engineering for the glucosylation of weakly recognized acceptors such as flavonoids.

Example 8: Determination of the Efficiencies of Naringenin Glucosylation by the Glucansucrases of the GH70 Family The glucansucrases of the GH70 family tested for their apigenin glucosylation activity are listed in table 4.

The results of naringenin glucosylation by the glucansucrases of the GH70 family are reported in table 6.

Table 6 illustrates the naringenin glucosylation efficiency for the wild-type form of the truncated variant of DSR-S (vardelΔ4N WT), for the truncated wild-type form of ASR (ASR C-APY-del WT), for the wild-type form of the α-1,2 BrS enzyme and for seven mutants of DSR-S vardelΔ4N.

The wild-type form of the truncated variant of ASR (ASR C-APY-del WT) exhibits a glucosylation efficiency of 27.1%. The wild-type enzyme α-1,2 BrS exhibits a naringenin glucosylation efficiency of 26.8%.

Example 9: LC-MS Analysis of the Naringenin Glucosylation Products

Figure 3:
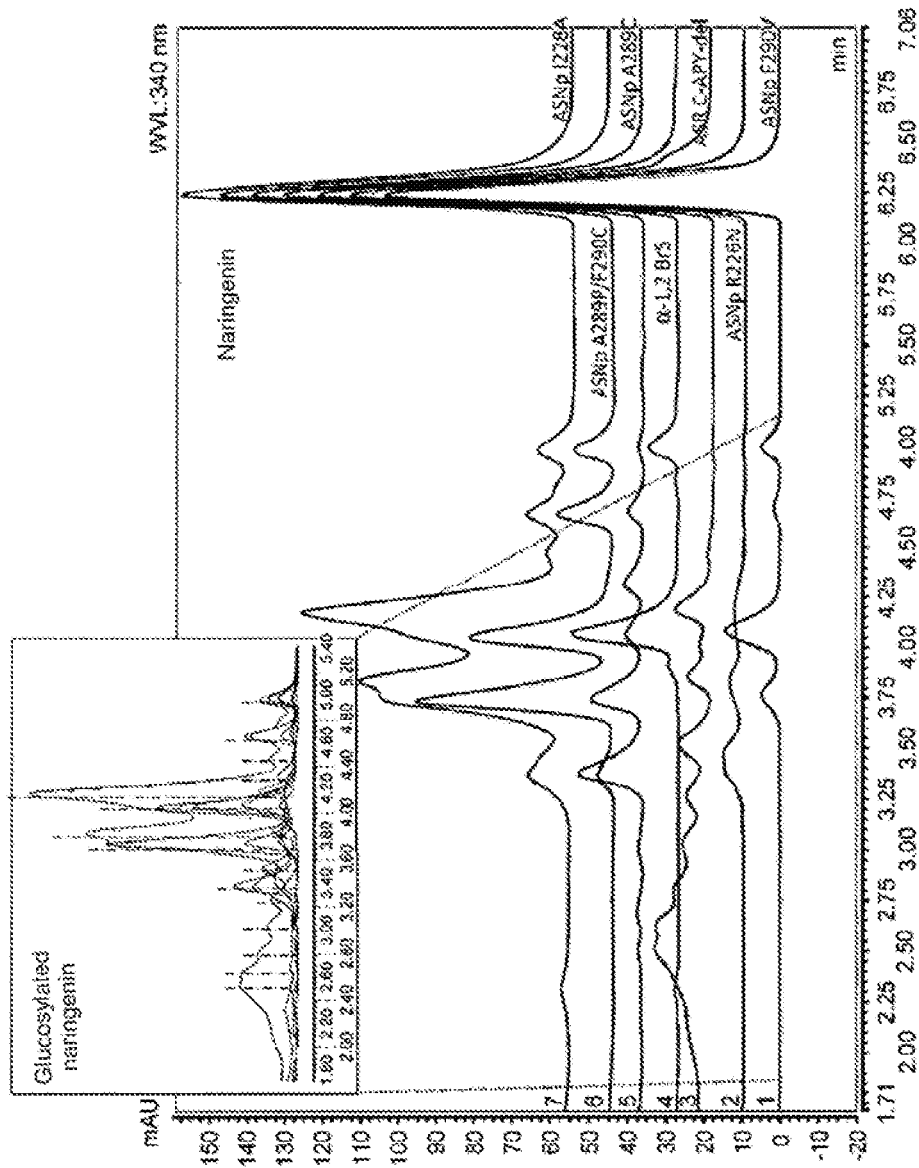
FIG. 3 illustrates the superimposition of the UV chromatograms (λ340 nm) for the seven mutants representative of the six naringenin glucosylation product profile categories. The name of the enzymes corresponding to these reactions is indicated beside each chromatogram: ASNp F290V, ASNp R226N, ASR C-APY del, α-1,2 BrS, ASNp A289C, ASNp A289P/F290C and ASNp I228A. Along the X-axis: Retention time in minutes; Along the Y-axis: Absorbance in mAU (milliabsorbance units).

The eighteen mutants having a naringenin glucosylation efficiency greater than 10%, discussed in examples 7 and 8, may be classified in seven categories according to the glucosylation product profiles obtained in LC-MS. The superimposition of the UV chromatograms (λ340 nm) for a representative of each of these seven profile categories is represented in FIG. 3.

The superimposition of these chromatograms demonstrates the diversity of glucosylated naringenin forms that it is possible to obtain.

The LC-MS profiles obtained for ASNp WT, the five mutant enzymes of ASNp and the two glucansucrases of the GH70 family which are the most efficient are represented in FIGS. 20 a 27.

The molar masses, as determined by LC-MS in example 1, of the strongest glucosylated naringenin peak for each of these profiles are the following:

FIG. 20: not determined
FIG. 21: 433.6 g/mol
FIG. 22: 595.5 g/mol
FIG. 23: 758.4 g/mol
FIG. 24: 595.5 g/mol
FIG. 25: 433.8 g/mol
FIG. 26: 433.8 g/mol
FIG. 27: 758.0 g/mol The wild-type enzyme (FIG. 20) has a reduced glucosylation efficiency on naringenin (4.7%). Indeed, if the naringenin standard is compared with the final products of the glucosylation reaction, the appearance on the UV chromatogram of several peaks, of low strengths, of glucosylated naringenin is detected (FIG. 20).

The naringenin glucosylation profiles obtained with the enzymes ASNp R226N, ASNp I228A, ASNp A289C, ASNp F290V, ASNp A289P/F290C, ASR-C-APY-del or α-1,2 BrS are all distinct (FIGS. 21 to 27).

Example 10: Production, Purification and Structural Determination by NMR of 4'-O-α-D-glucopyranosylnaringenin by the I228A Mutant of ASNp Production of 4'-O-α-D-glucopyranosylnaringenin The production of the glucosylation products is carried out with the ASNp I228A enzyme on 204 mg of naringenin. The reaction conditions are the following: final concentration of sucrose 146 mM, of naringenin 5 mM (initially dissolved in DMSO at 150 mM), PBS buffer, pH 7.2, ASNp I228A 0.5 U/ml and ultrapure water qs 145 ml. The reaction is carried out with stirring at 30° C. for 24 h. At the end of the reaction, the enzyme is heat inactivated. The reaction mixture is stored at −20° C.

Purification of 4'-O-α-D-glucopyranosylnaringenin

A prepurification step is carried out by solid phase extraction (SPE) on a cartridge containing 5 g of $C_{18}$ stationary phase. After conditioning of the column, the centrifuged reaction mixture is deposited on the column and percolates by gravity. After the steps of washing with ultrapure water, the elution is carried out with methanol. The eluate is dried under a nitrogen gas stream before being taken up in 100% DMSO at a concentration of 100 g/l.

The various glucosylated forms of naringenin are separated at ambient temperature by semi-preparative HPLC-UV on a Waters apparatus. A C18 250×10 mm column fitted with a precolumn makes it possible to separate the various glucosylated forms of naringenin with an aqueous mobile phase containing 0.05% (v/v) of formic acid with a gradient of acetonitrile (B). The various steps of the gradient are the following: 0 min, 22% B; 1 min, 22% B; 17 min, 25% B; 21 min, 29% B; 21.5 min, 95% B; 24.5 min, 95% B; 25 min, 22% B; 27.5 min, 22% B. On the basis of the UV signal, the elution fractions are collected in an automated manner. The purity of the elution fractions is evaluated by LC-UV-MS with a C18 250×4.6 mm analytical column (gradient described above).

The elution fractions containing a monoglucosylated form of naringenin which is 96% pure, eluting at a retention time of 18.4 min in semi-preparative HPLC-UV, are combined and dried using a GeneVac apparatus. The product is then dissolved in 300 μl de of deuterated methanol, dried under a nitrogen gas stream and then lyophilized for 48 h.

Structural Characterization of 4'-O-α-D-glucopyranosylnaringenin

The structural determination of this monoglucosylation product was carried out by NMR.

The 1H, COSY 1H-1H, JMod and HMBC 1H-13C spectra were recorded on a Bruker Avance 500 MHz apparatus at 298 K (500 MHz for $^1$H and 125 MHz for $^{13}$C) with a TBI z-gradient 5 mm probe. The data were acquired and processed using the TopSpin 3 software. The sample was analyzed in deuterated methanol.

The assignment of the various NMR signals is indicated on FIGS. 28, 29 and 30. The compound identified is 4'—O-α-D-glucopyranosylnaringenin. The $^3J_{H-1'',H-2}$ coupling constant of the H-1'' anomeric proton of the glucosyl residue is 3.4 Hz.

Example 11: Glucosylation of Naringenin and of Morin by the $\Delta N_{123}$-GBD-CD2 Enzyme and its Mutants Single or double variants constructed from the glucansucrose $\Delta N_{123}$-GBD-CD2 (belonging to the glycoside hydrolase family GH70) were tested for their ability to glucosylate naringenin and morin. The results of glucosylation of these two flavonoids, by variants of $\Delta N_{123}$-GBD-CD2, are reported in tables 7 and 8.

Regarding morin, the wild-type enzyme glucosylates it with a glucosylation efficiency of 20.4±3.2%.

Fourteen mutants which glucosylate this flavonol more efficiently than the wild-type enzyme, namely W403G, W403S-F404L, W403V, W403C, W403F, F431I-D432E-L434I, F431L, A430E-F43IL, W403F-F404I, W403C-F404I, W403N-F404Y, W403N-F404H, W403I-F404Y and W403L-F404L. The glucosylation efficiencies obtained for these mutants are represented in table 7.

Among them, nine mutants glucosylate morin with a glucosylation efficiency greater than or equal to 30% (mutants W403G, W403S-F404L, W403V, W403C, W403F, F431I-D432E-L434I, F431L, A430E-F431L and W403F-F404I). Two mutants even have a morin glucosylation efficiency greater than or equal to 40%, or even greater than or equal to 45% (mutants W403S-F404L and W403G). The best glucosylation efficiencies were obtained with the mutants W403S-F404L (49.5%) and W403G (66.7%). Morin glucosylation products were detected by LC-UV-MS (FIG. 31). One monoglucosylated compound, two diglucosylated compounds and one triglucosylated compound were identified. The best mutant for morin glucosylation is the variant W403G which synthesizes four times more diglucosylated morin than the wild-type enzyme.

Naringenin is glucosylated by $\Delta N_{123}$-GBD-CD2 WT with a glucosylation yield of 13.9±4.7% (table 8).

Nine variants exhibit a glucosylation efficiency greater than 20%, namely W403I-F404Y, W403V, W403G, W403F, W403S-F404L, W403C, F431I-D432E-L434I, F431L and A430E-F431L. The glucosylation efficiencies obtained are represented in table 8.

Seven of them have a glucosylation efficiency greater than or equal to 25% (W403I-F404Y, W403V, W403G, W403F, W403S-F404L, W403C, and F431I-D432E-L434I). More particularly, three variants have a glucosylation efficiency greater than or equal to 30%, or even greater than or equal to 35% (W403G, W403F, W403I-F404Y). The best degree of conversion of 59.3% was obtained with the variant W403I-F404Y. Regarding the naringenin glucosylation products, reaction products were detected by LC-UV-MS (FIG. 32). One monoglucosylated compound, two diglucosylated compounds and one triglucosylated compound were identified by mass spectrometry.

Naringenin is barely glucosylated by the wild-type enzyme (14%) and most of it is monoglucosylated (13%). In particular, a variant of the W403-F404 library exhibits an increase in production of the monoglucosylated product, up to 49% with the W403I-F404Y mutant. Finally, one variant (W403S-F404L) converts 10% of the naringenin to triglucosylated compound (compared with only 1% for the wild-type enzyme).

TABLE 1

| Organism | Glucansucrase | Major bonds in the natural polymer | References |
| --- | --- | --- | --- |
| Neisseria polysaccharea (EC 2.4.1.4) | ASNp WT and 152 single mutants and three double mutants of the active site (Positions 228, 229, 289, 290, 330, 331, 394, 446) | α-(1→4) | Albenne C. et al., *J. Biol. Chem.*, 2004 279(1) 726-734<br>Champion E., 2008. Doctoral thesis, INSA, Toulouse<br>Champion C. et al., *J. Am. Chem. Soc.*, 2009, 131, 7379-7389<br>Champion C. et al., *J. Am. Chem. Soc.*, 2012, 134, 18677-18688<br>EP08290238.8 |

TABLE 2

ASNp WT (n = 16)  0.5

| | A | C | D | E | F | G | H | I | K | L | M | N | P | Q | R | S | T | V | W | Y |
| --- | --- | --- | --- | --- | --- | --- | --- | --- | --- | --- | --- | --- | --- | --- | --- | --- | --- | --- | --- | --- |
| R226 | 1.7 | 1.4 | 0.7 | 1.4 | 2.7 | 1.4 | 1.5 | 1.7 | 1.1 | 0.9 | 1.7 | 1.3 | 2.2 | 2.4 | 0.3 | 1.6 | 1.9 | 1.6 | nd | 1.1 |
| I228 | 0.0 | 0.0 | 2.2 | 0.5 | 9.9 | 2.6 | 3.3 | 0.8 | 3.6 | 11.1 | 5.4 | 1.9 | 2.4 | 0.2 | 0.0 | 1.7 | 0.2 | 0.9 | 0.2 | 2.0 |
| F229 | 5.6 | 4.7 | 0.7 | 0.6 | 0.8 | 1.8 | 0.5 | 2.3 | 1.1 | 0.5 | 1.2 | 5.7 | 0.2 | 0.1 | 0.0 | 0.0 | 0.0 | 0.1 | 1.2 | 0.2 |
| A289 | 0.6 | 1.0 | 0.3 | 0.0 | 0.7 | 0.3 | 0.0 | 0.9 | 0.4 | 0.6 | 0.1 | 0.7 | 0.0 | 0.2 | 0.3 | 0.4 | 0.4 | 0.0 | 22.1 | 0.8 |
| F290 | 1.9 | 5.4 | 1.6 | 0.5 | 0.8 | 0.5 | 0.3 | 3.2 | 8.9 | 2.4 | 2.0 | 0.5 | 0.0 | 0.4 | 3.5 | 0.5 | 0.6 | 3.8 | 2.2 | 0.3 |
| I330 | 0.4 | 0.4 | 0.5 | 0.6 | 0.2 | 0.6 | 0.6 | 0.8 | 0.2 | 0.0 | 0.0 | 0.1 | 0.2 | 0.2 | 0.0 | 0.0 | 0.0 | 0.2 | 0.0 | 0.0 |
| V331 | 0.5 | 1.2 | 0.9 | 0.7 | 0.4 | 1.9 | 0.1 | 0.3 | 0.2 | 0.3 | 0.1 | 1.0 | 0.0 | 0.2 | 0.2 | 0.4 | 0.0 | 0.2 | 0.2 | 0.4 |
| D394 | 3.2 | 0.4 | 0.1 | 0.6 | 0.0 | 1.2 | 0.0 | 0.0 | 0.0 | 0.0 | 0.0 | 0.0 | 0.0 | 0.0 | 0.0 | 0.1 | 0.0 | 0.0 | 0.6 | 0.8 |
| R446 | 0.1 | 0.0 | 0.1 | 0.0 | 0.0 | 0.0 | 0.0 | 0.0 | 0.0 | 0.0 | 0.0 | 0.0 | 0.1 | 0.0 | 1.9 | nd | 0.3 | 0.0 | nd | 0.0 |

| A289P/F290C | A289P/F290I | A289P/F290L |
| --- | --- | --- |
| 2.1 | 3.0 | 2.9 | nd: data not available

TABLE 3

ASNp WT (n = 16)  4.7

| | A | C | D | E | F | G | H | I | K | L | M | N | P | Q | R | S | T | V | W | Y |
| --- | --- | --- | --- | --- | --- | --- | --- | --- | --- | --- | --- | --- | --- | --- | --- | --- | --- | --- | --- | --- |
| R226 | 2.4 | 3.9 | 3.9 | 1.0 | 4.6 | 4.8 | 13.5 | 4.9 | 5.1 | 3.7 | 3.5 | 16.0 | 3.1 | 4.7 | 2.5 | 14.1 | 8.7 | 5.9 | nd | 2.3 |
| I228 | 70.2 | 30.9 | 0.0 | 0.0 | 0.0 | 0.0 | 0.0 | 0.0 | 0.0 | 0.0 | 3.3 | 2.2 | 6.1 | 1.4 | 0.0 | 16.4 | 6.0 | 12.3 | 0.0 | 0.0 |
| F229 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 6.9 | 0.0 |
| A289 | 3.4 | 27.8 | 0.0 | 0.0 | 0.0 | 0.0 | 0.0 | 11.2 | 0.0 | 0.0 | 0.0 | 14.5 | 10.3 | 0.0 | 0.0 | 0.0 | 2.2 | 21.8 | 0.0 | 0.0 |
| F290 | 0.0 | 0.0 | 0.0 | 0.0 | 0.0 | 7.4 | 3.4 | 0.0 | 0.0 | 4.5 | 6.4 | 0.0 | 3.4 | 0.0 | 11.2 | 2.4 | 0.0 | 21.1 | 0.0 | 0.0 |
| I330 | 0.0 | 0.0 | 0.0 | 0.0 | 0.0 | 0.0 | 0.0 | 0.0 | 0.0 | 0.0 | 0.0 | 0.0 | 0.0 | 1.1 | 0.0 | 0.0 | 0.0 | 0.0 | 0.0 | 0.0 |
| V331 | 0.0 | 5.4 | 0.0 | 0.0 | 0.0 | 6.9 | 0.0 | 0.0 | 0.0 | 0.0 | 0.0 | 0.0 | 0.0 | 6.8 | 0.0 | 6.7 | 7.2 | 4.7 | 0.0 | 3.8 |
| D394 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| R446 | 0.0 | 0.0 | 0.0 | 0.0 | 0.0 | 0.0 | 0.0 | 0.0 | 0.0 | 0.0 | 0.0 | 0.0 | 0.0 | 0.0 | 6.0 | 0.0 | 0.0 | 0.0 | 0.0 | 0.0 |

| A289P/F290C | A289P/F290I | A289P/F290L |
| --- | --- | --- |
| 50.9 | 1.6 | 22.9 | nd: data not available

TABLE 4

| Organism | Glucansucrase | Major bonds in the natural polymer | References |
|---|---|---|---|
| Leuconostoc mesenteroides B-512F (EC 2.4.1.5) | DSR-S vardel Δ4N WT | α-(1→6) | Moulis. C., 2006. Doctoral thesis, INSA, Toulouse and Moulis C. et al., FEMS Microbiol. Lett., 2006 261 203-210 |
| Leuconostoc mesenteroides B-512F (EC 2.4.1.5) | Seven mutants of DSR-S vardel Δ4N: F353T or S512C or F353W or H463R/T464D/S512T or H463R/T464V/S512T or D460A/H463S/T464L or D460M/H463Y/T464M/S512C | α-(1→6) | Irague R. et al., Anal. Chem. 2011 83(4) 1202-1206 |
| Leuconostoc mesenteroides NRRL B-1355 (EC 2.4.1.140) | ASR C-APY-del | α-(1→3)/ α-(1→6) | Joucla. G., 2003. Doctoral thesis, INSA, Toulouse and Joucla G et al., FEBS Lett. 2006 580(3) 763-768 |
| Leuconostoc mesenteroides NRRL B-1299 | Mutant of DSR-E $\Delta N_{123}$-GBD-CD2 | α-(1→2) | Brison et al., J. Biol. Chem., 2012, 287, 7915-24 |

TABLE 5

| DSR-S vardelΔ4N WT | ASR C-APY-del WT | α-1,2 BrS | DSR-S vardelΔ4N F353T | DSR-S vardelΔ4N S512C | DSR-S vardelΔ4N F353W | DSR-S vardelΔ4N H463R/T464D/ S512T | DSR-S vardelΔ4N H463R/T464V/ S512T | DSR-S vardelΔ4N D460A/H463S/ T464L | DSR-S vardelΔ4N D460M/H463Y/ T464M/S512C |
|---|---|---|---|---|---|---|---|---|---|
| 0.5 | 0.6 | 2.5 | 0.5 | 13.9 | 0.5 | 0.5 | 0.5 | 0.5 | 0.5 |

The number indicated in each case is the percentage glucosylation efficiency.

TABLE 6

| DSR-S vardelΔ4N WT | ASR C-APY-del WT | α-1,2 BrS | DSR-S vardelΔ4N F353T | DSR-S vardelΔ4N S512C | DSR-S vardelΔ4N F353W | DSR-S vardelΔ4N H463R/T464D/ S512T | DSR-S vardelΔ4N H463R/T464V/ S512T | DSR-S vardelΔ4N D460A/H463S/ T464L | DSR-S vardelΔ4N D460M/H463Y/ T464M/S512C |
|---|---|---|---|---|---|---|---|---|---|
| 0.0 | 27.1 | 26.8 | 0.0 | 0.0 | 0.0 | 0.0 | 0.0 | 0.0 | 0.0 |

The number indicated in each case is the percentage glucosylation efficiency

TABLE 7

| Morin | |
|---|---|
| W403G | 66.7 |
| W403S-F404L | 49.5 |
| W403V | 38.6 |
| W403C | 35.4 |
| W403F | 33.4 |
| F431I-D432E-L434I | 32.5 |
| F431L | 32.4 |
| A430E-F431L | 31.2 |
| W403F-F404I | 30.4 |
| W403C-F404I | 29.1 |
| W403N-F404Y | 28.0 |
| W403N-F404H | 26.7 |
| W403I-F404Y | 25.2 |
| W403L-F404L | 24.8 |
| $\Delta N_{123}$-GBD-CD2 WT | 20.4 |

TABLE 8

| Naringenin | |
|---|---|
| W403I-F404Y | 59.3 |
| W403V | 42.3 |
| W403G | 38.5 |
| W403F | 35.5 |
| W403S-F404L | 29.4 |
| W403C | 26.7 |
| F431I-D432E-L434I | 25.0 |
| F431L | 24.8 |
| A430E-F431L | 20.9 |
| $\Delta N_{123}$-GBD-CD2 WT | 13.9 |

Efficiencies of morin glucosylation (table 7) and of naringenin glucosylation (table 8) by the wild-type glucansucrose $\Delta N_{123}$-GBD-CD2 and the best mutants resulting from the secondary screening.

SEQUENCES

Series SEQ ID NO: 1: (Proteins = mutated sequence of the glucansucrose ASNp (Amylosucrase Neisseria polysaccharea) R226X$_1$)
SPNSQYLKTRILDIYTPEQRAGIEKSEDWRQFSRRMDTHFPKLMNELDSV

YGNNEALLPMLENILLAQAWQSYSQRNSSLKDIDIARENNPDWILSNKQV

GGVCYVDLFAGDLKGLKDKIPYFQELGLTYLHLMPLFKCPEGKSDGGYAV

SSYRDVNPALGTIGDLREVIAALHEAGISAVVDFIFNHTSNEHEWAQRCA

AGDPLFDNFYYIFPDRRMPDQYDRTLRE$X_1$FPDQHPGGFSQLEDGRWVWT

TFNSFQWDLNYSNPWVFRAMAGEMLFLANLGVDILRMDAVAFIWKQMGTS

CENLPQAHALIRAFNAVMRIAAPAVFFKSEAIVHPDQVVQYIGQDECQIG

YNPLQMALLWNTLATREVNLLHQALTYRHNLPEHTAWVNYVRSHDDIGWT

FADEDAAYLGISGYDHRQFLNRFFVNRFDGSFARGVPFQYNPSTGDCRVS

GTAAALVGLAQDDPHAVDRIKLLYSIALSTGGLPLIYLGDEVGTLNDDDW

SQDSNKSDDSRWAHRPRYNEALYAQRNDPSTAAGQIYQDLRHMIAVRQSN

PRFDGGRLVTFNTNNKHIIGYIRNNALLAFGNFSEYFIQTVTAHTLQAMP

FKAHDLIGKKTVSLNQDLTLQPYQVMWLEIA

Series SEQ ID NO: 2: (Proteins = mutated sequence
of the glucansucrase ASNp (Amylosucrase Neisseria
polysaccharea) I228$X_2$)
SPNSQYLKTRILDIYTPEQRAGIEKSEDWRQFSRRMDTHFPKLMNELDSV

YGNNEALLPMLEMLLAQAWQSYSQRNSSLKDIDIARENNPDWILSNKQVG

GVCYVDLFAGDLKGLKDKIPYFQELGLTYLHLMPLFKCPEGKSDGGYAVS

SYRDVNPALGTIGDLREVIAALHEAGISAVVDFIFNHTSNEHEWAQRCAA

GDPLFDNFYYIFPDRRMPDQYDRTLRE$X_2$FPDQHPGGFSQLEDGRWVWTT

FNSFQWDLNYSNPWVFRAMAGEMLFLANLGVDILRMDAVAFIWKQMGTSC

ENLPQAHALIRAFNAVMRIAAPAVFFKSEAIVHPDQVVQYIGQDECQIGY

NPLQMALLWNTLATREVNLLHQALTYRHNLPEHTAWVNYVRSHDDIGWTF

ADEDAAYLGISGYDHRQFLNRFFVNRFDGSFARGVPFQYNPSTGDCRVSG

TAAALVGLAQDDPHAVDRIKLLYSIALSTGGLPLIYLGDEVGTLNDDDWS

QDSNKSDDSRWAHRPRYNEALYAQRNDPSTAAGQIYQDLRHMIAVRQSNP

RFDGGRLVTFNTNNKHIIGYIRNNALLAFGNFSEYPQTVTAHTLQAMPFK

AHDLIGGKTVSLNQDLTLQPYQVMWLEIA

Series SEQ ID NO: 3: (Proteins = mutated sequence
of the glucansucrase ASNp (Amylosucrase Neisseria
polysaccharea) F229$X_3$)
SPNSQYLKTRILDIYTPEQRAGIEKSEDWRQFSRRMDTHFPKLMNELDSV

YGNNEALLPMLEMLLAQAWQSYSQRNSSLKDIDIARENNPDWILSNKQVG

GVCYVDLFAGDLKGLKDKIPYFQELGLTYLHLMPLFKCPEGKSDGGYAVS

SYRDVNPALGTIGDLREVIAALHEAGISAVVDFIFNHTSNEHEWAQRCAA

GDPLFDNFYYIFPDRRMPDQYDRTLREI$X_3$PDQHPGGFSQLEDGRWVWTT

FNSFQWDLNYSNPWVFRAMAGEMLFLANLGVDILRNIDAVAFIWKQMGTS

CENLPQAHALIRAFNAVMRIAAPAVFFKSEAIVHPDQVVQYIGQDECQIG

YNPLQMALLWNTLATREVNLLHQALTYRHNLPEHTAWVNYVRSHDDIGWT

FADEDAAYLGISGYDHRQFLNRFFVNRFDGSFARGVPFQYNPSTGDCRVS

GTAAALVGLAQDDPHAVDRIKLLYSIALSTGGLPLIYLGDEVGTLNDDDW

SQDSNKSDDSRWAHRPRYNEALYAQRNDPSTAAGQIYQDLRHMIAVRQSN

PRFDGGRLVTFNTNNKHIIGYIRNNALLAFGNFSEYPQTVTAHTLQAMPF

KAHDLIGGKTVSLNQDLTLQPYQVMWLEIA

SEQ ID NO: 4: (Protein = mutated sequence of the
glucansucrase ASNp (Amylosucrase Neisseria
polysaccharea) A289$X_4$)
SPNSQYLKTRILDIYTPEQRAGIEKSEDWRQFSRRMDTHFPKLMNELDSV

YGNNEALLPMLEMLLAQAWQSYSQRNSSLKDIDIARENNPDWILSNKQVG

GVCYVDLFAGDLKGLKDKIPYFQELGLTYLHLMPLFKCPEGKSDGGYAVS

SYRDVNPALGTIGDLREVIAALHEAGISAVVDFIFNHTSNEHEWAQRCAA

GDPLFDNFYYIFPDRRMPDQYDRTLREIFPDQHPGGFSQLEDGRWVWTTF

NSFQWDLNYSNPWVFRAMAGEMLFLANLGVDILRMDAV$X_4$FIWKQMGTSC

ENLPQAHALIRAFNAVMRIAAPAVFFKSEAIVHPDQVVQYIGQDECQIGY

NPLQMALLWNTLATREVNLLHQALTYRHNLPEHTAWVNYVRSHDDIGWTF

ADEDAAYLGISGYDHRQFLNRFFVNRFDGSFARGVPFQYNPSTGDCRVSG

TAAALVGLAQDDPHAVDREKLLYSIALSTGGLPLIYLGDEVGTLNDDDWS

QDSNKSDDSRWAHRPRYNEALYAQRNDPSTAAGQIYQDLRHMIAVRQSNP

RFDGGRLVTFNTNNKHIIGYIRNNALLAFGNFSEYPQTVTAHTLQAMPFK

AHDLIGGKTVSLNQDLTLQPYQVMWLEIA

Series SEQ ID NO: 5: (Proteins = mutated sequence
of the glucansucrase ASNp (Amylosucrase Neisseria
polysaccharea) F290$X_5$)
SPNSQYLKTRILDIYTPEQRAGIEKSEDWRQFSRRMDTHFPKLMNELDSV

YGNNEALLPMLEMLLAQAWQSYSQRNSSLKDIDIARENNPDWILSNKQVG

GVCYVDLFAGDLKGLKDKIPYFQELGLTYLHLMPLFKCPEGKSDGGYAVS

SYRDVNPALGTIGDLREVIAALHEAGISAVVDFIFNHTSNEHEWAQRCAA

GDPLFDNFYYIFPDRRMPDQYDRTLREIFPDQHPGGFSQLEDGRWVWTTF

NSFQWDLNYSNPWVFRAMAGEMLFLANLGVDILRMDAVA$X_5$IWKQMGTSC

ENLPQAHALIRAFNAVMRIAAPAVFFKSEAIVHPDQVVQYIGQDECQIGY

NPLQMALLWNTLATREVNLLHQALTYRHNLPEHTAWVNYVRSHDDIGWTF

ADEDAAYLGISGYDHRQFLNRFFVNRFDGSFARGVPFQYNPSTGDCRVSG

TAAALVGLAQDDPHAVDRIKLLYSIALSTGGLPLIYLGDEVGTLNDDDWS

QDSNKSDDSRWAHRPRYNEALYAQRNDPSTAAGQIYQDLRHMIAVRQSNP

RFDGGRLVTFNTNNKHIIGYIRNNALLAFGNFSEYPQTVTAHTLQAMPFK

AHDLIGGKTVSLNQDLTLQPYQVMWLEIA

Series SEQ ID NO: 6: (Proteins = mutated sequence
of the glucansucrase ASNp (Amylosucrase Neisseria
polysaccharea) V331$X_6$)
SPNSQYLKTRILDIYTPEQRAGIEKSEDWRQFSRRMDTHFPKLMNELDSV

YGNNEALLPMLEMLLAQAWQSYSQRNSSLKDIDIARENNPDWILSNKQVG

GVCYVDLFAGDLKGLKDKIPYFQELGLTYLHLMPLFKCPEGKSDGGYAVS

SYRDVNPALGTIGDLREVIAALHEAGISAVVDFIFNHTSNEHEWAQRCAA

GDPLFDNFYYIFPDRRMPDQYDRTLREIFPDQHPGGFSQLEDGRWVWTTF

NSFQWDLNYSNPWVFRAMAGEMLFLANLGVDILRMDAVAFIWKQMGTSCE

NLPQAHALIRAFNAVMRIAAPAVFFKSEAI$X_6$HPDQVVQYIGQDECQIGY

NPLQMALLWNTLATREVNLLHQALTYRHNLPEHTAWVNYVRSHDDIGWTF

ADEDAAYLGISGYDHRQFLNRFFVNRFDGSFARGVPFQYNPSTGDCRVSG

TAAALVGLAQDDPHAVDRIKLLYSIALSTGGLPLIYLGDEVGTLNDDDWS

-continued

QDSNKSDDSRWAHRPRYNEALYAQRNDPSTAAGQIYQDLRHMIAVRQSNP

RFDGGRLVTFNTNNICHIIGYIRNNALLAFGNFSEYPQTVTAHTLQAMPF

KAHDLIGGKTVSLNQDLTLQPYQVMWLEIA

Series SEQ ID NO: 7: (Proteins = mutated sequence
of the glucansucrase ASNp (Amylosucrase Neisseria
polysaccharea) D394X$_7$)
SPNSQYLKTRILDIYTPEQRAGIEKSEDWRQFSRRMDTHFPKLMNELDSV

YGNNEALLPMLEMLLAQAWQSYSQRNSSLKDIDIARENNPDWILSNKQVG

GVCYVDLFAGDLKGLKDKIPYFQELGLTYLHLMPLFKCPEGKSDGGYAVS

SYRDVNPALGTIGDLREVIAALHEAGISAVVDFIFNHTSNEHEWAQRCAA

GDPLFDNFYYIFPDRRMPDQYDRTLREIFPDQHPGGFSQLEDGRWVWTTF

NSFQWDLNYSNPWVFRAMAGEMLFLANLGVDILRMDAVAFIWKQMGTSCE

NLPQAHALIRAFNAVMRIAAPAVFFKSEAIVHPDQVVQYIGQDECQIGYN

PLQMALLWNTLATREVNLLHQALTYRHNLPEHTAWVNYVRSHDX$_7$IGWTF

ADEDAAYLGISGYDHRQFLNRFFVNRFDGSFARGVPFQYNPSTGDCRVSG

TAAALVGLAQDDPHAVDRIKLLYSIALSTGGLPLIYLGDEVGTLNDDDWS

QDSNKSDDSRWAHRPRYNEALYAQRNDPSTAAGQIYQDLRHMIAVRQSNP

RFDGGRLVTFNTNNKHIIGYIRNNALLAFGNFSEYPQTVTAHTLQAMPFK

AHDLIGGKTVSLNQDLTLQPYQVMWLEIA

SEQ ID NO: 8: (Protein = mutated sequence of the
glucansucrase ASNp (Amylosucrase Neisseria
polysaccharea) R446Q)
SPNSQYLKTRILDIYTPEQRAGIEKSEDWRQFSRRMDTHFPKLMNELDSV

YGNNEALLPMLEMLLAQAWQSYSQRNSSLKDIDIARENNPDWILSNKQVG

GVCYVDLFAGDLKGLKDKIPYFQELGLTYLHLMPLFKCPEGKSDGGYAVS

SYRDVNPALGTIGDLREVIAALHEAGISAVVDFIFNHTSNEHEWAQRCAA

GDPLFDNFYYIFPDRRMPDQYDRTLREIFPDQHPGGFSQLEDGRWVWTTF

NSFQWDLNYSNPWVFRAMAGEMLFLANLGVDILRMDAVAFIWKQMGTSCE

NLPQAHALIRAFNAVMRIAAPAVFFKSEAIVHPDQVVQYIGQDECQIGYN

PLQMALLWNTLATREVNLLHQALTYRHNLPEHTAWVNYVRSHDDIGWTFA

DEDAAYLGISGYDHRQFLNRFFVNRFDGSFARGVPFQYNPSTGDCQVSGT

AAALVGLAQDDPHAVDRIKLLYSIALSTGGLPLIYLGDEVGTLNDDDWSQ

DSNKSDDSRWAHRPRYNEALYAQRNDPSTAAGQIYQDLRHMIAVRQSNPR

FDGGRLVTFNTNNKHIIGYIRNNALLAFGNFSEYPQTVTAHTLQAMPFKA

HDLIGGKTVSLNQDLTLQPYQVMWLEIA

Series SEQ ID NO: 9: (Proteins = doubly mutated
sequences of the glucansucrase ASNp (Amylosucrase
Neisseria polysaccharea) A289P/F290X$_8$)
SPNSQYLKTRILDIYTPEQRAGIEKSEDWRQFSRRMDTHFPKLMNELDSV

YGNNEALLPMLEMLLAQAWQSYSQRNSSLKDIDIARENNPDWILSNKQVG

GVCYV DLFAGDLKGLKDKIPYFQELGLTYLHLMPLFKCPEGKSDGGYA

VSSYRDVNPALGTIGDLREVIAALHEAGISAVVDFIFNHTSNEHEWAQRC

AAGDPLFDNFYYIFPDRRMPDQYDRTLREIFPDQHPGGFSQLEDGRWVWT

TFNSFQWDLNYSNPWVFRAMAGEMLFLANLGVDILRMDAVPX$_8$IWKQMGT

SCENLPQAHALIRAFNAVMRIAAPAVFFKSEAIVHPDQVVQYIGQDECQI

GYNPLQMALLWNTLATREVNLLHQALTYRHNLPEHTAWVNYVRSHDDIGW

TFADEDAAYLGISGYDHRQFLNRFFVNRFDGSFARGVPFQYNPSTGDCRV

SGTAAALVGLAQDDPHAVDRIKLLYSIALSTGGLPLIYLGDEVGTLNDDD

WSQDSNKSDDSRWAHRPRYNEALYAQRNDPSTAAGQIYQDLRHMIAVRQS

NPRFDGGRLVTFNTNNKHIIGYIRNNALLAFGNFSEYPQTVTAHTLQAMP

FKAHDLIGGKTVSLNQDLTLQPYQVMWLEIA

SEQ ID NO: 10: (Protein = mutated sequence of the
truncated glucansucrase DSR-S vardelΔ4N-S512C
TQQVSGKYVEKDGSWYYYFDDGKNAKGLSTIDNNIQYFYESGKQAKG

QYVTIDNQTYYFDKGSGDELTGLQSIDGNIVAFNDEGQQIFNQYYQSENG

TTYYFDDKGHAATGIKNIEGKNYYFDNLGQLKKGFSGVIDGQIMTFDQET

GQEVSNTTSEIKEGLTTQNTDYSEHNAAHGTDAEDFENIDGYLTASSWYR

PTGELRNGTDWEPSTDTDFRPILSVWWPDKNTQVNYLNYMADLGFISNAD

SFETGDSQSLLNEASNYVQKSIEMKISAQQSTEWLKDAMAAFIVAQPQWN

ETSEDMSNDHLQNGALTYVNSPLTPDANSNFRLLNRTPTNQTGEQAYNLD

NSKGGFELLLANQEDNSNVVVEAEQLNWLYYLMNFGTITANDADANFDGI

RVDAVDNVDADLLQIAADYFKLAYGVDQNDATANQHLSILEDWSHNDPLY

VTDQGSNQLTMDDYVHTQLIWSLTKSSDIRGTMQRFVDYYMVDRSNDSTE

NEAIPNYSFVRAHDCEVQTVIAQIVSDLYPDVENSLAPTTEQLAAAFKVY

NEDEKLADKKYTQYNMASAYAMLLTNKDTVPRVYYGDLYTDDGQYMATKS

PYYDAINTLLKARVQYVAGGQSMSVDSNDVLTSVRYGKDAMTASDTGTSE

TRTEGIGVIVSNNAELQLEDGHTVTLHMGAARKNQAYRALLSTTADGLAY

YDTDENAPVAYTDANGDLIFTNESIYGVQNPQVSGYLAVWVPVGAQQDQD

ARTASDTTTNTSDKVFHSNAALDSQVIYEGFSNFQAFATDSSEYTNVVIA

QNADQFKQWGVTSFQLAPQYRSSTDTSFLDSIIQNGYAFTDRYDLGYGTP

TKYGTADQLRDAIKALHASGIQAIADWVPDQIYNLPEQELATVTRTNSFG

DDDTDSDIDNALYVVQSRGGGQYQEMYGGAFLEELQALYPSLFKVNQIST

GVPIDGSVKITEWAAKYFNGSNIQGKGAGYVLKDMGSNKYFKVVSNTEDG

DYLPKQLTNDLSETGFTHDDKGIIYYTLSGYRAQNAFIQDDDNNYYYFDK

TGHLVTGLQKINNHTYFFLPNGIELVKSFLQNEDGTIVYFDKKGHQVFDQ

YITDQNGNAYYFDDAGVNILKSGLATIDGHQQYFDQNGVQVKDKFVIGTD

GYKYYFEPGSGNLAILRYVQNSKNQWFYFDGNGHAVTGFQTINGKKQYFY

NDGHQSKGEFIDADGDTFYTSATDGRLVTGVQKINGITYAFDNTGNLITN

QYYQLADGKYMLLDDSGRAKTGFVLQDGVLRYFDQNGEQVKDAIIVDPDT

NLS.

SEQ ID NO: 11: (Protein = sequence of the
glucansucrase α-1,2 BrS)
MRQKETITRKKLYKSGKSWVAAATAFAVMGVSAVTTVSADTQTPVGT

TQSQQDLTGQRGQDKPTTKEVIDKKEPVPQVSAQNAGDLSADAKTTKADD

KQDTQPTNAQLPDQGNKQTNSNSDKGVKESTTAPVKTTDVPSKSVTPETN

TSINGGQYVEKDGQFVYIDQSGKQVSGLQNIEGHTQYFDPKTGYQTKGEL

KNIDDNAYYFDKNSGNGRTFTKISNGSYSEKDGMWQYVDSHDKQPVKGLY

DVEGNLQYFDLSTGNQAKHQIRSVDGVTYYFDADSGNATAFKAVTNGRYA

EQTTKDKDGNETSYWAYLDNQGNAIKGLNDVNGEIQYFDEHTGEQLKGHT

ATLDGTTYYFEGNKGNLVSVVNTAPTGQYKINGDNVYYLDNNNEAIKGLY

GINGNLNYFDLATGIQLKGQAKNIDGIGYYFDKDTGNGSYQYTLMAPSNK

NDYTQHNVVNNLSESNFKNLVDGFLTAETWYRPAQILSHGTDWVASTDKD

FRPLITVWWPNKDIQVNYLRLMQNEGVLNQSAVYDLNTDQLLLNEAAQQA

QIGIEKKISQTGNTDWLNNVLFTTHDGQPSFIKQQYLWNSDSEYHTGPFQ

GGYLKYQNSDLTPNVNSKYRNADNSLDFLLANDVDNSNPIVQAEDLNWLY

YLLNFGSITTQGKENNSNFDSIRIDAVDFVSNDLIQRTYDYLRAAYGVDK

NDKEANAHLSLVEAGLDAGTTTIHQDALIESDIREAMKKSLTNGPGSNIS

LSNLIQDKEGDKLIADRANNSTENVAIPNYSIIHAHDKDIQDKVGAAITD

ATGADWTNFTPEQLQKGLSLYYEDQRKIEKKYNQYNIPSAYALLLTNKDT

VPRVYYGDMYQDDGQYMQKQSLYFDTITALMEARKQFVAGGQTINVDDNG

VLTSVRFGKGANITANDIGTNETRTQGIGVVIANDPSLKLSKDSKVTLHM

GAAHRNQNYRALLLTTDNGIDSYSSSKNAPVIKTDDNGDLVFSNQDINDQ

LNTKVHGFLNSEVSGYLSAWVPLDATEQQDARTLPSEKSVNDGKVLHSNA

ALDSNLIYEAFSNFQPMPTNRNEYTNVVIADKADTFKSWGITSFEMAPQY

RSSQDKTFLDSTIDNGYAFTDRYDLGFEKPTKYGNDEDLRQAIKQLHSSG

MQVMADVVANQIYNLPGKEVASTNRVDWNGNNLSTPFGTQMYVVNTVGGG

KYQNKYGGEFLDKLKAAYPDIFRSKNYEYDVKNYGGNGTGSVYYTVDSKT

RAELDTDTKIKEWSAKYMNGTNVLGLGMGYVLKDWQTGQYFNVSNQNMKF

LLPSDLISNDITVQLGVPVTDKKIIFDPASAYNMYSNLPEDMQVMDYQDD

KKSTPSIKPLSSYNNKQVQVTRQYTDSKGVSWNLITFAGGDLQGQKLWVD

SRALTMTPFKTMNQISFISYANRNDGLFLNAPYQVKGYQLAGMSNQYKGQ

QVTIAGVANVSGKDWSLISFNGTQYWIDSQALNTNFTHDMNQKVFVNTTS

NLDGLFLNAPYRQPGYKLAGLAKNYNNQTVTVSQQYFDDQGTVWSQVVLG

GQTVWVDNHALAQMQVRDTNQQLYVNSNGRNDGLFLNAPYRGQGSQLIGM

TADYNGQHVQVTKQGQDAYGAQWRLITLNNQQVWVDSRALSTTIMQAMND

DMYVNSSQRTDGLLNAPYTMSGAKWAGDTRSANGRYVHISKAYSNEVGNT

YYLTNLNGQSTWIDKRAFTATFDQVVALNATIVARQRPDGMFKTAPYGEA

GAQFVDYVTNYNQQTVPVTKQHSDAQGNQWYLATVNGTQYWIDQRSFSPV

VTKVVDYQAKIVPRTTRDGVFSGAPYGEVNAKLVNMATAYQNQVVHATGE

YTNASGITWSQFALSGQEDKLWIDKRALQA

Series SEQ ID NO: 12: (Protein = mutated sequence
of the glucansucrase ΔN$_{123}$-GBD-CD2) (W403X$_9$;
F404X$_{10}$; A430X$_{11}$; F431X$_{12}$; and L434X$_{13}$)
MAHHHHHHVTSLYKKAGSAAAPFTMAQAGHYITKNGNDWQYDTNGE

LAKGLRQDSNGKLRYFDLTTGIQAKGQFVTIGQETYYFSKDHGDAQLLPM

VTEGHYGTITLKQGQDTKTAWVYRDQNNTILKGLQNINGTLQFFDPYTGE

QLKGGVAKYDDKLFYFESGKGNLVSTVAGDYQDGHYISQDGQTRYADKQN

QLVKGLVTVNGALQYFDNATGNQIKNQQVIVDGKTYYFDDKGNGEYLFTN

TLDMSTNAFSTKNVAFNHDSSSFDHTVDGFLTADTWYRPKSILANGTTWR

DSTDKDMRPLITVWWPNKNVQVNYLNFMKANGLLTTAAQYTLHSDQYDLN

QAAQDVQVATFRRIASEHGTDWLQKLLFESQNNNPSFVKQQFIWNKDSEY

HGGGDAX$_9$X$_{10}$QGGYLKYGNNPLTPTTNSDYRQPGNX$_{11}$X$_{12}$DFX$_{13}$LAN

DVDNSNPVVQAENLNWLHYLMNFGTITAGQDDANFDSIRIDAVDFIHNDT

IQRTYDYLRDAYQVQQSEAKANQHISLVEAGLDAGTSTIHNDALIESNLR

EAATLSLTNEPGKNKPLTNMLQDVDGGTLITDHTQNSTENQATPNYSIIH

AHDKGVQEKVGAAITDATGADWTNFTDEQLKAGLELFYKDQRATNKKYNS

YNIPSIYALMLTNKDTVPRMYYGDMYQDDGQYMANKSIYYDALVSLMTAR

KSYVSGGQTMSVDNHGLLKSVRFGKDAMTANDLGTSATRTEGLGVIIGND

PKLQLNDSDKVTLDMGAAHKNQKYRAVILTTRDGLATFNSDQAPTAWTND

QGTLTFSNQEINGQDNTQIRGVANPQVSGYLAVWVPVGASDNQDARTAAT

TTENHDGKVLHSNAALDSNLIYEGFSNFQPKATTHDELTNVVIAKNADVF

NNWGITSFEMAPQYRSSGDHTFLDSTIDNGYAFTDRYDLGFNTPTKYGTD

GDLRATIQALHHANMQVMADVVDNQVYNLPGKEVVSATRAGVYGNDDATG

FGTQLYVTNSVGGGQYQEKYAGQYLEALKAKYPDLFEGKAYDYWKNYAN

DGSNPYYTLSHGDRESIPADVAIKQWSAKYMNGTNVLGNGMGYVLKDWHN

GQYFKLDGDKSTLPKGGRADPAFLYKVVSAWSHPQFEK

Series SEQ ID NO: 13: (Protein = mutated sequence
of the glucansucrase ΔN$_{123}$-GBD-CD2) (F431I; D432E
and L434I)
MAHHHHHHVTSLYKKAGSAAAPFTMAQAGHYITKNGNDWQYDTNGE

LAKGLRQDSNGKLRYFDLTTGIQAKGQFVTIGQETYYFSKDHGDAQLLPM

VTEGHYGTITLKQGQDTKTAWVYRDQNNTILKGLQNINGTLQFFDPYTGE

QLKGGVAKYDDKLFYFESGKGNLVSTVAGDYQDGHYISQDGQTRYADKQN

QLVKGLVTVNGALQYFDNATGNQIKNQQVIVDGKTYYFDDKGNGEYLFTN

TLDMSTNAFSTKNVAFNHDSSSFDHTVDGFLTADTWYRPKSILANGTTWR

DSTDKDMRPLITVWWPNKNVQVNYLNFMKANGLLTTAAQYTLHSDQYDLN

QAAQDVQVATFRRIASEHGTDWLQKLLFESQNNNPSFVKQQFIWNKDSEY

HGGGDAWFQGGYLKYGNNPLTPTTNSDYRQPGNAIEFILANDVDNSNPVV

QAENLNWLHYLMNFGTITAGQDDANFDSIRIDAVDFIHNDTIQRTYDYLR

DAYQVQQSEAKANQHISLVEAGLDAGTSTIHNDALIESNLREAATLSLTN

EPGKNKPLTNMLQDVDGGTLITDHTQNSTENQATPNYSIIHAHDKGVQEK

VGAAITDATGADWTNFTDEQLKAGLELFYKDQRATNKKYNSYNIPSIYAL

MLTNKDTVPRMYYGDMYQDDGQYMANKSIYYDALVSLMTARKSYVSGGQT

MSVDNHGLLKSVRFGKDAMTANDLGTSATRTEGLGVIIGNDPKLQLNDSD

KVTLDMGAAFIKNQKYRAVILTTRDGLATFNSDQAPTAWTNDQGTLTFSN

QEINGQDNTQIRGVANPQVSGYLAVWVPVGASDNQDARTAATTTENHDGK

VLHSNAALDSNLIYEGFSNFQPKATTHDELTNVVIAKNADVFNNWGITSF

EMAPQYRSSGDHTFLDSTIDNGYAFTDRYDLGFNTPTKYGTDGDLRATIQ

ALHHANMQVMADVVDNQVYNLPGKEVVSATRAGVYGNDDATGFGTQLYVT

NSVGGGQYQEKYAGQYLEALKAKYPDLFEGKAYDYWKNYANDGSNPYYT

LSHGDRESIPADVAIKQWSAKYMNGTNVLGNGMGYVLKDWHNGQYFKLDG

DKSTLPKGGRADPAFLYKVVSAWSHPQFEK

The invention claimed is:

1. A process for producing O-α-glucosylated flavonoid derivatives, comprising at least one step of incubating a glucansucrase with a flavonoid and at least one sucrose, wherein:

(A) said flavonoid comprises formula (I) below:

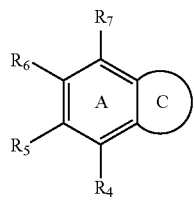

(I)

wherein the C ring represents a ring chosen from the group consisting of the rings of formula (II) and formula (IV) below:

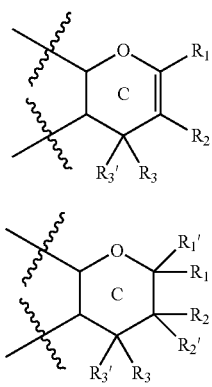

(II)

(IV)

wherein: the $R_1$ group represents a B ring of formula (VI) below:

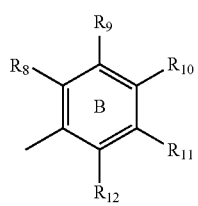

(VI)

wherein:
(a) just one of the groups chosen from $R_8$, $R_9$, $R_{10}$, $R_{11}$ and $R_{12}$ represents a hydroxyl group, the other groups among $R_8$, $R_9$, $R_{10}$, $R_{11}$ and $R_{12}$, which may be identical or different, being chosen from the group consisting of a hydrogen atom; a $C_1$ alkoxy group; a —C(W) group; and an —O(W) group, wherein W represents a chain consisting of 1 to 6 glycoside(s); or
(b) $R_8$ and just one of the groups chosen from $R_{10}$, $R_{11}$ and $R_{12}$ represents a hydroxyl group, $R_9$ and the other groups among $R_{10}$, $R_{11}$ and $R_{12}$, which may be identical or different being chosen from the group consisting of a hydrogen atom; a $C_1$ alkoxy group; a —C(W) group; and an —O(W) group, wherein W represents a chain consisting of 1 to 6 glycoside(s);

the $R_2$ and $R_3$ groups, which may be identical or different, being chosen from the group consisting of a hydrogen atom and an —OH group; $R_1'$, $R_2'$ and $R_3'$ is a hydrogen atom or $R_3$ and $R_3'$ groups together form an =O group; $R_4$, $R_5$, $R_6$ and $R_7$, which may be identical or different, being chosen from the group consisting of a hydrogen atom; a $C_1$ alkoxy group; an —OH; a —C(W) group; and an —O(W) group, wherein W represents a chain consisting of 1 to 6 glycoside(s); and (B) said glucansucrase comprises an amino acid sequence having at least 95% identity with the amino acid sequence of SEQ ID NO: 11.

2. The process in of claim 1, wherein $R_{10}$ represents a hydroxyl group, the other groups among $R_8$, $R_9$, $R_{11}$ and $R_{12}$, which may be identical or different, being chosen from the group consisting of a hydrogen atom; a $C_1$ alkoxy group; a —C(W) group; and an —O(W) group, wherein W represents a chain consisting of 1 to 6 glycoside(s).

3. The process of claim 2, wherein $R_{10}$ represents a hydroxyl group and $R_8$, $R_9$, $R_{11}$ and $R_{12}$ represent hydrogen atoms.

4. The process of claim 1, wherein
$R_8$ and just one of the groups chosen from $R_{10}$, $R_{11}$ and $R_{12}$ represent a hydroxyl group,
$R_9$ and the other groups among $R_{10}$, $R_{11}$ and $R_{12}$, which may be identical or different, being chosen from the group consisting of a hydrogen atom; a $C_1$ alkoxy group; a —C(W) group; and an —O(W) group, wherein W represents a chain consisting of 1 to 6 glycoside(s).

5. The process of claim 4, wherein $R_{10}$ represents a hydroxyl group and $R_9$, $R_{11}$ and $R_{12}$ represent hydrogen atoms.

6. The process of claim 1, wherein $R_1'$ and $R_2'$ represent hydrogen atoms, $R_2$ represents a hydrogen atom or an —OH group, and $R_3$ and $R_3'$ together form an =O group.

7. The process of claim 1, wherein two of the $R_4$, $R_5$, $R_6$ and $R_7$ groups represent a hydroxyl group, the other two groups are as defined in claim 1.

8. The process of claim 7, wherein $R_5$ and $R_7$ represent hydrogen atoms.

9. The process of claim 1, wherein said flavonoid is of formula (VII), (VII) or (IX) below:

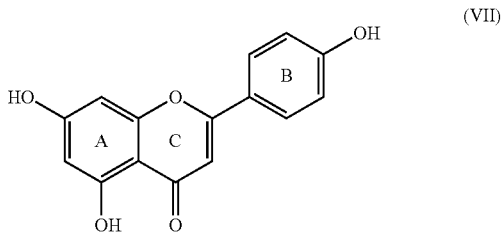

(VII)

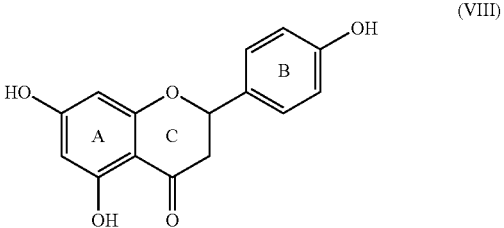

(VIII)

-continued

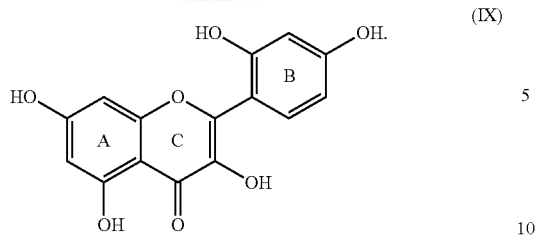
(IX)

10. The process of claim 1, wherein said glucansucrase comprises an amino acid sequence having at least 98% identity with the amino acid sequence of SEQ ID NO: 11.

11. The process of claim 1, wherein said glucansucrase comprises an amino acid sequence having at least 99% identity with the amino acid sequence of SEQ ID NO: 11.

12. The process of claim 1, wherein said glucansucrase comprises the amino acid sequence of SEQ ID NO: 11.

* * * * *